United States Patent
Hui et al.

(10) Patent No.: US 9,623,048 B2
(45) Date of Patent: Apr. 18, 2017

(54) HUMAN HEPATOCYTE-LIKE CELLS AND USES THEREOF

(71) Applicant: SHANGHAI INSTITUTES FOR BIOLOGICAL SCIENCES, CHINESE ACADEMY OF SCIENCES, Shanghai (CN)

(72) Inventors: Lijian Hui, Shanghai (CN); Pengyu Huang, Shanghai (CN); Ludi Zhang, Shanghai (CN); Yimeng Gao, Shanghai (CN)

(73) Assignee: SHANGHAI INSTITUTES FOR BIOLOGICAL SCIENCES, CHINESE ACADEMY OF SCIENCES (CN)

( * ) Notice: Subject to any disclaimer, the term of this patent is extended or adjusted under 35 U.S.C. 154(b) by 39 days.

(21) Appl. No.: 14/422,307

(22) PCT Filed: Feb. 8, 2014

(86) PCT No.: PCT/CN2014/071898
§ 371 (c)(1),
(2) Date: Feb. 18, 2015

(87) PCT Pub. No.: WO2014/121758
PCT Pub. Date: Aug. 14, 2014

(65) Prior Publication Data
US 2015/0190427 A1    Jul. 9, 2015

(30) Foreign Application Priority Data
Feb. 8, 2013  (CN) .......................... 2013 1 0050796

(51) Int. Cl.
| A61K 35/12 | (2015.01) |
| A61K 35/407 | (2015.01) |
| C12N 5/071 | (2010.01) |
| A61K 38/17 | (2006.01) |
| G01N 33/50 | (2006.01) |

(52) U.S. Cl.
CPC ............ *A61K 35/12* (2013.01); *A61K 35/407* (2013.01); *A61K 38/1709* (2013.01); *C12N 5/0602* (2013.01); *C12N 5/067* (2013.01); *G01N 33/5014* (2013.01); *G01N 33/5017* (2013.01); *C12N 2501/60* (2013.01); *C12N 2506/1307* (2013.01); *C12N 2510/00* (2013.01)

(58) Field of Classification Search
CPC ............................. C12N 2501/60; C12N 5/67
See application file for complete search history.

(56) References Cited

U.S. PATENT DOCUMENTS

| 4,789,733 A | 12/1988 | Winkelman |
| 5,486,359 A | 1/1996 | Caplan et al. |
| 5,624,840 A | 4/1997 | Naughton et al. |
| 5,759,830 A | 6/1998 | Vacanti et al. |
| 5,863,531 A | 1/1999 | Naughton et al. |
| 6,576,469 B1 | 6/2003 | Struhl et al. |
| 7,026,137 B2 | 4/2006 | Yeh |
| 7,282,366 B2 | 10/2007 | Rambhatla et al. |
| 8,481,317 B2 * | 7/2013 | Yu .......................... C12N 5/067 424/93.21 |
| 8,486,699 B2 | 7/2013 | Talbot et al. |
| 2002/0022018 A1 | 2/2002 | Curiel et al. |
| 2003/0022375 A1 | 1/2003 | Itoh et al. |
| 2003/0027335 A1 | 2/2003 | Ruley et al. |
| 2004/0216178 A1 | 10/2004 | Jones et al. |
| 2005/0130919 A1 | 6/2005 | Xu et al. |
| 2005/0148073 A1 | 7/2005 | Hansen et al. |
| 2005/0249816 A1 | 11/2005 | Atala et al. |
| 2007/0249045 A1 | 10/2007 | Gimble et al. |
| 2008/0060099 A1 | 3/2008 | Gordon-Kamm et al. |
| 2008/0124379 A1 | 5/2008 | Kaemmerer et al. |
| 2008/0241116 A1 | 10/2008 | Calos |
| 2009/0099066 A1 | 4/2009 | Moulton et al. |
| 2009/0156503 A1 | 6/2009 | Divita et al. |
| 2009/0311765 A1 | 12/2009 | Maguire et al. |
| 2010/0279918 A1 | 11/2010 | Langel et al. |
| 2010/0284990 A1 | 11/2010 | Kaemmerer et al. |
| 2011/0125286 A1 | 5/2011 | Selden et al. |
| 2011/0195056 A1 | 8/2011 | Pryor et al. |
| 2012/0009086 A1 | 1/2012 | Nyberg et al. |
| 2012/0111795 A1 | 5/2012 | Chamuleau et al. |
| 2013/0095077 A1 | 4/2013 | Wang |
| 2013/0130297 A1 * | 5/2013 | Ott .......................... C12N 5/067 435/29 |
| 2013/0344154 A1 | 12/2013 | Talbot et al. |

FOREIGN PATENT DOCUMENTS

| CN | 102465115 A | 5/2012 |
| CN | WO 2012058868 A1 * | 5/2012 ............. C12N 5/067 |
| CN | 104781393 A | 7/2015 |

(Continued)

OTHER PUBLICATIONS

Jonckheere et al. 2007; The human mucin MUC4 is transcriptionall regulated by caudal-related homeobox hepatocyte nuclear factors, forkhead box A, and GATA endodermal transcription factors in epithelial cancer cells. Journal of Biological Chemistry. 282(31)22638-22650.*
Giuliani et al. 2008; Detection of oncogenic DNA viruses in colorectal cancer. Anticancer Research 28: 1405-1410.*
Strand et al. 2002; Alginate-polylysine-alginate microcapsules: effect of size reduction on capsule properties. J. Microcapsulation. 19 (5): 615-630.*
Pan et al. published online Aug. 29, 2012; Establishment and characterization of immortalized human hepatocyte cell line for applications in bioartificial livers. Biotechnol. Lett. 34: 2183-2190.*
Mali, P., et al., "RNA-Guided Human Genome Engineering via Cas9", Science, vol. 339, Feb. 15, 2013, pp. 823-826.

(Continued)

*Primary Examiner* — Karen Cochrane Carlson
(74) *Attorney, Agent, or Firm* — Banner & Witcoff, Ltd.

(57) ABSTRACT

The present invention relates to hepatocyte-like cells. Also disclosed are methods of making the cells and using the cells.

29 Claims, 17 Drawing Sheets

(56) References Cited

FOREIGN PATENT DOCUMENTS

| DE | WO 2011141405 A1 * | 11/2011 | ............ C12N 5/067 |
|----|-----|-----|-----|
| EP | 2 248 889 A1 | 11/2010 | |
| JP | 2001-505917 A | 5/2001 | |
| JP | 2007-508019 A | 4/2007 | |
| JP | 2007-518426 A | 7/2007 | |
| JP | 2009-535035 A | 10/2009 | |
| JP | 2011-128 A | 1/2011 | |
| JP | 2012-525825 A | 10/2012 | |
| JP | 2013-252081 A | 12/2013 | |
| WO | 96/39487 A1 | 12/1996 | |
| WO | 98/25637 A1 | 6/1998 | |
| WO | 03/076564 A2 | 9/2003 | |
| WO | 2005/034876 A2 | 4/2005 | |
| WO | 2005/039643 A3 | 5/2005 | |
| WO | 2005/112620 A2 | 12/2005 | |
| WO | 2011/052504 A1 | 5/2011 | |
| WO | 2011/141405 A1 | 11/2011 | |
| WO | 2012/058868 A1 | 5/2012 | |
| WO | 2013/176772 A1 | 11/2013 | |

OTHER PUBLICATIONS

Stetsenko, D.A., et al., "Chemical Methods for Peptide-Oligonucleotide Conjugate Synthesis", Methods in Molecular Biology, vol. 288, pp. 205-224.
Itahana, K., et al., "A Role for p53 in Maintaining and Establishing the Quiescence Growth Arrest in Human Cells", The Journal of Biological Chemistry, vol. 277, No. 20, May 18, 2002, pp. 18206-18214.
International Search dated May 19, 2014 for Application No. PCT/CN2014/071898.
Land, H., et al., "Tumorigenic conversion of primary embryo fibroblasts requires at least two cooperating oncogenes", Nature, vol. 304, Aug. 18, 1983, pp. 596-602.
Carpentier, B., et al., "Artificial and bioartificial liver devices: present and future", Gut 58, 2009, pp. 1690-1702.
Azuma, H., et al., "Robust expansion of human hepatocytes in Fah-/-/Rag2-/-/Il2rg-/-mice", Nat Biotechnol, vol. 25, No. 8, pp. 903-910.
Gomez-Lechon, M.J., et al., "Human Hepatocytes in Primary Culture: The Choice to Investigate Drug Metabolism in Man", Current Drug Metabolism 5, 2004, pp. 443-462.
Lazaro, C., et al., Hepatitis C Virus Replication in Transfected and Serum-Infected Cultured Human Fetal Hepatocytes, 2007), Am J Pathol, vol. 170, No. 2, Feb. 2007, pp. 478-489.
Nam, Youmg-Jae, et al., "Reprogramming of human fibroblasts toward a cardiac fate", 2013, Proc Natl Acad Sci, vol. 110, No. 14, Apr. 2, 2013, pp. 5588-5593, pp. 1-8.
Pang, Z, et al.,"Induction of human neuronal cells by defined transcription factors", 2011, Nature, vol. 476, Aug. 11, 2011, pp. 220-223.
Qiang, L, et al., "Directed Conversion of Alzheimer's Disease Patient Skin Fibroblasts into Functional Neurons", Cell 146, Aug. 5, 2011, pp. 359-371.
Huang, P., et el., "Induction of functional hepatocyte-like cells from mouse fibroblasts by defined factors", Nature, vol. 475, Jul. 21, 2011, pp. 386-389.
Sekiya, S., et al., "Direct conversion of mouse fibroblasts to hepatocyte-like cells by defined factors", Nature, vol. 475, Jul. 21, 2011, pp. 390-393.
Cherry, A, et al., "Reprogramming cellular identity for regenerative medicine", Cell, 148(6), Mar. 16, 2012, pp. 1-22.
Tiscornia, G., et al., "Diseases in a dish: modeling human genetic disorders using induced pluripotent cells", Nat Med, vol. 17, No. 12, Dec. 2011, pp. 1570-1576.
Vierbuchen, T., et al., "Direct lineage conversions: unnatural but useful?", Nat Biotechnol, vol. 29, No. 10, Oct. 2011, pp. 892-907.
Tachikawa, K., et al.,"Regulation of the endogenous VEGF-A gene by exogenous designed regulatory proteins", PNAS, vol. 101, No. 42, Oct. 19, 2004, pp. 15225-15230.

Cristiano, R.J., et al., "Molecular conjugates: a targeted gene delivery vector for molecular medicine", J. Mol. Med. 73, 1995, pp. 479-486.
Miyoshi, H., et al., "Hepatocyte culture utilizing porous polyvinyl formal resin maintains long-term stable albumin secretion activity", J Biomater Sci. Polym. Ed., vol. 9, No. 3, pp. 227-237.
Gebhardt, R., et al., "Biliary Secretion of Sodium Fluorescein in Primary Monolayer Cultures of Adult Rat Hepatocytes and its Stimulation by Nicotinamide", . Cell Sci. , 56, 1982, pp. 233-244.
Passonneau, J.V., et al., "A Comparison of Three Methods of Glycogen Measurement in Tissues", Anal. Biochem. 60, 1974, pp. 405-412.
Cong, L., et al., "Multiplex Genome Engineering Using CRISPR/Cas Systems", Science, vol. 339, Feb. 15, 2013, pp. 819-823.
Jinek, M., et al., "A Programmable Dual-RNA-Guided DNA Endonuclease in Adaptive Bacterial Immunity", Science, vol. 337, Aug. 17, 2012, pp. 816-821.
Gasiunas, G., et al., "Cas9-crRNA ribonucleoprotein complex mediates specific DNA cleavage for adaptive immunity in bacteria", Proc Natl Acad Sci, Sep. 4, 2012, pp. E2579-E2586.
Cho, S. W., et al., "Targeted genome engineering in human cells with the Cas9 RNARNARNA-guided endonuclease", Nature Biotechnology, vol. 31, No. 3, Mar. 2013, pp. 230-232.
Hou, Z., et al., "Efficient genome engineering in human pluripotent stem cells using Cas9 from *Neisseria meningitides*", Proc Natl Acad Sci, vol. 110, No. 39, Sep. 24, 2013, pp. 15644-15649.
Mojica, F.J.M., et al., "Short motif sequences determine the targets of the prokaryotic CRISPR defence system", Microbiology, 155, 2009, pp. 733-740.
Dhawan, A., et al., "Human hepatocyte transplantation: current experience and future challenges", ), Nature reviews Gastroenterology & Hepatology, vol. 7, May 2010, pp. 288-298.
Pan, G., et al.,"Assessment of Biliary Clearance in Early Drug Discovery Using Sandwich-Cultured Hepatocyte Model", J Pharm Sci, vol. 101, No. 5, May 5, 2012, pp. 1898-1908.
He, Z, et al., "Liver Xeno-Repopulation with Human Hepatocytes in Fah-/-Rag2-/- Mice after Pharmacological Immunosuppression", Am J Pathol, vol. 177, No. 3, Sep. 2010, pp. 1311-1319.
Palakkan, A., et al., "Liver tissue engineering and cell sources: issues and challenges", Liver International, 2013, pp. 666-676.
Kane, W., et al., "Purification and Characterization of Human Coagulation Factor V*", J. Biol. Chem., vol. 256, No. 2, Jan. 25, 1981, pp. 1002-1007.
Hengstler, J., et al., "Cryopreserved Primary Hepatocytes as a Constantly Available in vitro Model for the evaluation of Human and Animal Drug Metabolism and Enzyme Induction*", Drug Metabolism Reviews, 32(1), 2000, pp. 81-118.
Li, A., "Human hepatocytes: Isolation, cryopreservation and applications in drug development", Chemico-Biological Interactions, 168, 2007, pp. 16-29.
Li, A., et al., "Cryopreserved human hepatocytes: characterization of drug-metabolizing enzyme activities and applications in higher throughput screening assays for hepatotoxicity, metabolic stability, and drug-drug interaction potential", Chemico-Biological Interactions, 121, 1999, pp. 17-35.
Hewitt, N., et al., "Primary Hepatocytes: Current Understanding of the Regulation of Metabolic Enzymes and Transporter Proteins, and Pharmaceutical Practice for the Use of Hepatocytes in Metabolism, Enzyme Induction, Transporter, Clearance, and Hepatotoxicity Studies", Drug Metabolism Reviews 39, 2007, pp. 159-234.
Monostory, K., et al., "The effect of synthetic glucocorticoid, dexamethasone on CYP1A1 inducibility in adult rat and human hepatocytes", FEBS Letters, 579, 2005, pp. 229-235.
Roymans, D., et al., "Determination of cytochrome P450 1A2 and cytochrome P450 3A4 induction in cryopreserved human hepatocytes", Biochemical Pharmacology 67, 2004, pp. 427-437.
Hartman, J., et al., "Evaluation of the endothelin receptor antagonists ambrisentan, darusentan, bosentan, and sitaxsentan as substrates and inhibitors of hepatobiliary transporters in sandwich-cultured human hepatocytes", Canadian Journal of Physiology and Pharmacology, 88, 2010, pp. 682-691.

(56) References Cited

OTHER PUBLICATIONS

Marion, T., et al., "Endogenous bile acid disposition in rat and human sandwich-cultured hepatocytes", Toxicology and Applied Pharmacology, 261, 2012, pp. 1-9.

Takebe, T., et al., "Vascularized and functional human liver from an iPSC-derived organ bud transplant", Nature, vol. 499, Jul. 25, 2013, pp. 481-484.

Sridharan, R., et al., "Role of the murine reprogramming factors in the induction of pluripotency", Cell, 136(2), Jan. 23, 2009, pp. 364-377.

Mei, J., et al., "Improved Survival of Fulminant Liver Failure by Transplantation of Microencapsulated Cryopreserved Porcine Hepatocytes in Mice", Cell Transplant, vol. 18, 2009, pp. 101-110.

Orive, G., et al., "History, challenges and perspectives of cell microencapsulation", Trends Biotechnol, vol. 22, No. 2, Feb. 2004, pp. 87-92.

Wang, Q., et al., "Cytoskeletal reorganization and repolarization of hepatocarcinoma cells in APA microcapsule to mimic native tumor characteristics", Hepatol Res, 35, 2006, pp. 96-103.

Xie, H., et al., "Basic properties of alginate/chitosan microcapsule surfaces and their interaction with proteins", J Control Release, 152, 2011, pp. e246-e248.

Liu, X., et al., "Correlation of Biliary Excretion in Sandwich-Cultured Rat Hepatocytes and in vivo in Rats", Drug Metab Dispos, vol. 27, No. 6, 1999, pp. 637-644.

Ames, B., et al., "Methods for Detecting Carcinogens and Mutagens with the *Salmonella*/Mammalian-Microsome Mutagenicity Test*", Mut. Res., 31, 1975. pp. 347-363.

Liu, T., "Effect of the Lentivirus-mediated Constitutive Expression of Foxa2 and Hnf4a upon the Hepatic Differentiation of Embryonic Stem Cells", Medicine and Health Science, vol. 2011, No. 5, May 2011, 125 pages.

Ding, Y., et al., "Research progress and prospects of bioartificial liver system", World Chinese Journal of Digestology, vol. 16, No. 26, May 15, 2011, pp. 2907-2915.

Karim, S., et al., "Highly Efficient Generation of Human Hepatocyte-Like Cells from Induced Pluripotent Stem Cells", Hepatology, vol. 51, No. 31, Jan. 2010, pp. 297-305.

Espacenet English abstract of CN 104781393 A.

Espacenet English abstract of WO 2011/052504 A1.

Espacenet English abstract of JP 2011-128 A.

Espacenet English abstract of JP 2013-252081 A.

Espacenet English abstract of.

Jonckheere, N., et al., "The Human Mucin MUC4 is Transcriptionally Regulated by Caudal-related Homeobox, Hepatocyte Nuclear Factors, Forkhead Box A, and GATA Endodermal Transcription Factors in Epithelial Cancer Cells", Journal of Biological Chemistry, vol. 282, No. 31, Aug. 3, 2007, 26 pages.

Giuliani, L , et al., "Detection of Oncogenic DNA Viruses in Colorectal Cancer", Anticancer Research, 28, 2008, pp. 1405-1410.

\* cited by examiner

Morphology

HFF+T+FOXA3+HNF4A

SEQUENCE LISTING

```
<160> NUMBER OF SEQ ID NOS: 162

<210> SEQ ID NO 1
<211> LENGTH: 350
<212> TYPE: PRT
<213> ORGANISM: Homo sapiens

<400> SEQUENCE: 1

Met Leu Gly Ser Val Lys Met Glu Ala His Asp Leu Ala Glu Trp Ser
1               5                   10                  15

Tyr Tyr Pro Glu Ala Gly Glu Val Tyr Ser Pro Val Thr Pro Val Pro
                20                  25                  30

Thr Met Ala Pro Leu Asn Ser Tyr Met Thr Leu Asn Pro Leu Ser Ser
            35                  40                  45

Pro Tyr Pro Pro Gly Gly Leu Pro Ala Ser Pro Leu Pro Ser Gly Pro
    50                  55                  60

Leu Ala Pro Pro Ala Pro Ala Ala Pro Leu Gly Pro Thr Phe Pro Gly
65                  70                  75                  80

Leu Gly Val Ser Gly Ser Ser Ser Gly Tyr Gly Ala Pro Gly
                85                  90                  95

Pro Gly Leu Val His Gly Lys Glu Met Pro Lys Gly Tyr Arg Arg Pro
                100                 105                 110

Leu Ala His Ala Lys Pro Pro Tyr Ser Tyr Ile Ser Leu Ile Thr Met
            115                 120                 125

Ala Ile Gln Gln Ala Pro Gly Lys Met Leu Thr Leu Ser Glu Ile Tyr
    130                 135                 140

Gln Trp Ile Met Asp Leu Phe Pro Tyr Tyr Arg Glu Asn Gln Gln Arg
145                 150                 155                 160

Trp Gln Asn Ser Ile Arg His Ser Leu Ser Phe Asn Asp Cys Phe Val
                165                 170                 175

Lys Val Ala Arg Ser Pro Asp Lys Pro Gly Lys Gly Ser Tyr Trp Ala
                180                 185                 190

Leu His Pro Ser Ser Gly Asn Met Phe Glu Asn Gly Cys Tyr Leu Arg
            195                 200                 205

Arg Gln Lys Arg Phe Lys Leu Glu Glu Lys Val Lys Lys Gly Gly Ser
    210                 215                 220

Gly Ala Ala Thr Thr Thr Arg Asn Gly Thr Gly Ser Ala Ala Ser Thr
225                 230                 235                 240

Thr Thr Pro Ala Ala Thr Val Thr Ser Pro Pro Gln Pro Pro Pro Pro
                245                 250                 255

Ala Pro Glu Pro Glu Ala Gln Gly Gly Glu Asp Val Gly Ala Leu Asp
                260                 265                 270

Cys Gly Ser Pro Ala Ser Ser Thr Pro Tyr Phe Thr Gly Leu Glu Leu
            275                 280                 285

Pro Gly Glu Leu Lys Leu Asp Ala Pro Tyr Asn Phe Asn His Pro Phe
    290                 295                 300

Ser Ile Asn Asn Leu Met Ser Glu Gln Thr Pro Ala Pro Pro Lys Leu
```

```
                305                 310                 315                 320
Asp Val Gly Phe Gly Gly Tyr Gly Ala Glu Gly Gly Glu Pro Gly Val
                    325                 330                 335
Tyr Tyr Gln Gly Leu Tyr Ser Arg Ser Leu Leu Asn Ala Ser
                340                 345                 350

<210> SEQ ID NO 2
<211> LENGTH: 557
<212> TYPE: PRT
<213> ORGANISM: Homo sapiens

<400> SEQUENCE: 2

Met Val Ser Lys Leu Thr Ser Leu Gln Gln Glu Leu Leu Ser Ala Leu
1               5                   10                  15

Leu Ser Ser Gly Val Thr Lys Glu Val Leu Val Gln Ala Leu Glu Glu
                20                  25                  30

Leu Leu Pro Ser Pro Asn Phe Gly Val Lys Leu Glu Thr Leu Pro Leu
            35                  40                  45

Ser Pro Gly Ser Gly Ala Glu Pro Asp Thr Lys Pro Val Phe His Thr
        50                  55                  60

Leu Thr Asn Gly His Ala Lys Gly Arg Leu Ser Gly Asp Glu Gly Ser
65                  70                  75                  80

Glu Asp Gly Asp Asp Tyr Asp Thr Pro Pro Ile Leu Lys Glu Leu Gln
                85                  90                  95

Ala Leu Asn Thr Glu Glu Ala Ala Glu Gln Arg Ala Glu Val Asp Arg
                100                 105                 110

Met Leu Ser Glu Asp Pro Trp Arg Ala Ala Lys Met Ile Lys Gly Tyr
            115                 120                 125

Met Gln Gln His Asn Ile Pro Gln Arg Glu Val Val Asp Val Thr Gly
        130                 135                 140

Leu Asn Gln Ser His Leu Ser Gln His Leu Asn Lys Gly Thr Pro Met
145                 150                 155                 160

Lys Thr Gln Lys Arg Ala Ala Leu Tyr Thr Trp Tyr Val Arg Lys Gln
                165                 170                 175

Arg Glu Ile Leu Arg Gln Phe Asn Gln Thr Val Gln Ser Ser Gly Asn
            180                 185                 190

Met Thr Asp Lys Ser Ser Gln Asp Gln Leu Leu Phe Leu Phe Pro Glu
        195                 200                 205

Phe Ser Gln Gln Ser His Gly Pro Gly Gln Ser Asp Asp Ala Cys Ser
210                 215                 220

Glu Pro Thr Asn Lys Lys Met Arg Arg Asn Arg Phe Lys Trp Gly Pro
225                 230                 235                 240

Ala Ser Gln Gln Ile Leu Tyr Gln Ala Tyr Asp Arg Gln Lys Asn Pro
                245                 250                 255

Ser Lys Glu Glu Arg Glu Ala Leu Val Glu Glu Cys Asn Arg Ala Glu
            260                 265                 270

Cys Leu Gln Arg Gly Val Ser Pro Ser Lys Ala His Gly Leu Gly Ser
        275                 280                 285

Asn Leu Val Thr Glu Val Arg Val Tyr Asn Trp Phe Ala Asn Arg Arg
        290                 295                 300

Lys Glu Glu Ala Phe Arg Gln Lys Leu Ala Met Asp Ala Tyr Ser Ser
305                 310                 315                 320

Asn Gln Thr His Ser Leu Asn Pro Leu Leu Ser His Gly Ser Pro His
                325                 330                 335
```

-continued

His Gln Pro Ser Ser Pro Pro Asn Lys Leu Ser Gly Val Arg Tyr
                340                 345                 350

Ser Gln Gln Gly Asn Asn Glu Ile Thr Ser Ser Thr Ile Ser His
            355                 360                 365

His Gly Asn Ser Ala Met Val Thr Ser Gln Ser Val Leu Gln Gln Val
370                 375                 380

Ser Pro Ala Ser Leu Asp Pro Gly His Asn Leu Leu Ser Pro Asp Gly
385                 390                 395                 400

Lys Met Ile Ser Val Ser Gly Gly Leu Pro Pro Val Ser Thr Leu
                405                 410                 415

Thr Asn Ile His Ser Leu Ser His His Asn Pro Gln Gln Ser Gln Asn
            420                 425                 430

Leu Ile Met Thr Pro Leu Ser Gly Val Met Ala Ile Ala Gln Ser Leu
            435                 440                 445

Asn Thr Ser Gln Ala Gln Ser Val Pro Val Ile Asn Ser Val Ala Gly
            450                 455                 460

Ser Leu Ala Ala Leu Gln Pro Val Gln Phe Ser Gln Gln Leu His Ser
465                 470                 475                 480

Pro His Gln Gln Pro Leu Met Gln Gln Ser Pro Gly Ser His Met Ala
                485                 490                 495

Gln Gln Pro Phe Met Ala Ala Val Thr Gln Leu Gln Asn Ser His Met
            500                 505                 510

Tyr Ala His Lys Gln Glu Pro Pro Gln Tyr Ser His Thr Ser Arg Phe
            515                 520                 525

Pro Ser Ala Met Val Val Thr Asp Thr Ser Ser Ile Ser Thr Leu Thr
530                 535                 540

Asn Met Ser Ser Lys Gln Cys Pro Leu Gln Ala Trp
545                 550                 555

<210> SEQ ID NO 3
<211> LENGTH: 442
<212> TYPE: PRT
<213> ORGANISM: Homo sapiens

<400> SEQUENCE: 3

Met Tyr Gln Ser Leu Ala Met Ala Ala Asn His Gly Pro Pro Pro Gly
1               5                   10                  15

Ala Tyr Glu Ala Gly Gly Pro Gly Ala Phe Met His Gly Ala Gly Ala
                20                  25                  30

Ala Ser Ser Pro Val Tyr Val Pro Thr Pro Arg Val Pro Ser Ser Val
            35                  40                  45

Leu Gly Leu Ser Tyr Leu Gln Gly Gly Gly Ala Gly Ser Ala Ser Gly
        50                  55                  60

Gly Ala Ser Gly Gly Ser Gly Gly Ala Ser Gly Ala Gly Pro
65                  70                  75                  80

Gly Thr Gln Gln Gly Ser Pro Gly Trp Ser Gln Ala Gly Ala Asp Gly
                85                  90                  95

Ala Ala Tyr Thr Pro Pro Pro Val Ser Pro Arg Phe Ser Phe Pro Gly
            100                 105                 110

Thr Thr Gly Ser Leu Ala Ala Ala Ala Ala Ala Ala Ala Arg Glu
        115                 120                 125

Ala Ala Ala Tyr Ser Ser Gly Gly Gly Ala Ala Gly Ala Gly Leu Ala
    130                 135                 140

Gly Arg Glu Gln Tyr Gly Arg Ala Gly Phe Ala Gly Ser Tyr Ser Ser
145                 150                 155                 160

-continued

```
Pro Tyr Pro Ala Tyr Met Ala Asp Val Gly Ala Ser Trp Ala Ala Ala
            165                 170                 175

Ala Ala Ala Ser Ala Gly Pro Phe Asp Ser Pro Val Leu His Ser Leu
            180                 185                 190

Pro Gly Arg Ala Asn Pro Ala Ala Arg His Pro Asn Leu Asp Met Phe
            195                 200                 205

Asp Asp Phe Ser Glu Gly Arg Glu Cys Val Asn Cys Gly Ala Met Ser
210                 215                 220

Thr Pro Leu Trp Arg Arg Asp Gly Thr Gly His Tyr Leu Cys Asn Ala
225                 230                 235                 240

Cys Gly Leu Tyr His Lys Met Asn Gly Ile Asn Arg Pro Leu Ile Lys
            245                 250                 255

Pro Gln Arg Arg Leu Ser Ala Ser Arg Arg Val Gly Leu Ser Cys Ala
            260                 265                 270

Asn Cys Gln Thr Thr Thr Thr Thr Leu Trp Arg Arg Asn Ala Glu Gly
            275                 280                 285

Glu Pro Val Cys Asn Ala Cys Gly Leu Tyr Met Lys Leu His Gly Val
            290                 295                 300

Pro Arg Pro Leu Ala Met Arg Lys Glu Gly Ile Gln Thr Arg Lys Arg
305                 310                 315                 320

Lys Pro Lys Asn Leu Asn Lys Ser Lys Thr Pro Ala Ala Pro Ser Gly
            325                 330                 335

Ser Glu Ser Leu Pro Pro Ala Ser Gly Ala Ser Ser Asn Ser Ser Asn
            340                 345                 350

Ala Thr Thr Ser Ser Ser Glu Glu Met Arg Pro Ile Lys Thr Glu Pro
            355                 360                 365

Gly Leu Ser Ser His Tyr Gly His Ser Ser Val Ser Gln Thr Phe
            370                 375                 380

Ser Val Ser Ala Met Ser Gly His Gly Pro Ser Ile His Pro Val Leu
385                 390                 395                 400

Ser Ala Leu Lys Leu Ser Pro Gln Gly Tyr Ala Ser Pro Val Ser Gln
            405                 410                 415

Ser Pro Gln Thr Ser Ser Lys Gln Asp Ser Trp Asn Ser Leu Val Leu
            420                 425                 430

Ala Asp Ser His Gly Asp Ile Ile Thr Ala
            435                 440

<210> SEQ ID NO 4
<211> LENGTH: 474
<212> TYPE: PRT
<213> ORGANISM: Homo sapiens

<400> SEQUENCE: 4

Met Arg Leu Ser Lys Thr Leu Val Asp Met Asp Met Ala Asp Tyr Ser
1               5                   10                  15

Ala Ala Leu Asp Pro Ala Tyr Thr Thr Leu Glu Phe Glu Asn Val Gln
            20                  25                  30

Val Leu Thr Met Gly Asn Asp Thr Ser Pro Ser Glu Gly Thr Asn Leu
        35                  40                  45

Asn Ala Pro Asn Ser Leu Gly Val Ser Ala Leu Cys Ala Ile Cys Gly
    50                  55                  60

Asp Arg Ala Thr Gly Lys His Tyr Gly Ala Ser Ser Cys Asp Gly Cys
65                  70                  75                  80

Lys Gly Phe Phe Arg Arg Ser Val Arg Lys Asn His Met Tyr Ser Cys
```

```
                        85                  90                  95
Arg Phe Ser Arg Gln Cys Val Val Asp Lys Asp Lys Arg Asn Gln Cys
                100                 105                 110
Arg Tyr Cys Arg Leu Lys Lys Cys Phe Arg Ala Gly Met Lys Lys Glu
                115                 120                 125
Ala Val Gln Asn Glu Arg Asp Arg Ile Ser Thr Arg Ser Ser Tyr
    130                 135                 140
Glu Asp Ser Ser Leu Pro Ser Ile Asn Ala Leu Leu Gln Ala Glu Val
145                 150                 155                 160
Leu Ser Arg Gln Ile Thr Ser Pro Val Ser Gly Ile Asn Gly Asp Ile
                165                 170                 175
Arg Ala Lys Lys Ile Ala Ser Ile Ala Asp Val Cys Glu Ser Met Lys
                180                 185                 190
Glu Gln Leu Leu Val Leu Val Glu Trp Ala Lys Tyr Ile Pro Ala Phe
                195                 200                 205
Cys Glu Leu Pro Leu Asp Asp Gln Val Ala Leu Leu Arg Ala His Ala
                210                 215                 220
Gly Glu His Leu Leu Leu Gly Ala Thr Lys Arg Ser Met Val Phe Lys
225                 230                 235                 240
Asp Val Leu Leu Leu Gly Asn Asp Tyr Ile Val Pro Arg His Cys Pro
                245                 250                 255
Glu Leu Ala Glu Met Ser Arg Val Ser Ile Arg Ile Leu Asp Glu Leu
                260                 265                 270
Val Leu Pro Phe Gln Glu Leu Gln Ile Asp Asp Asn Glu Tyr Ala Tyr
                275                 280                 285
Leu Lys Ala Ile Ile Phe Phe Asp Pro Asp Ala Lys Gly Leu Ser Asp
                290                 295                 300
Pro Gly Lys Ile Lys Arg Leu Arg Ser Gln Val Gln Val Ser Leu Glu
305                 310                 315                 320
Asp Tyr Ile Asn Asp Arg Gln Tyr Asp Ser Arg Gly Arg Phe Gly Glu
                325                 330                 335
Leu Leu Leu Leu Leu Pro Thr Leu Gln Ser Ile Thr Trp Gln Met Ile
                340                 345                 350
Glu Gln Ile Gln Phe Ile Lys Leu Phe Gly Met Ala Lys Ile Asp Asn
                355                 360                 365
Leu Leu Gln Glu Met Leu Leu Gly Gly Ser Pro Ser Asp Ala Pro His
                370                 375                 380
Ala His His Pro Leu His Pro His Leu Met Gln Glu His Met Gly Thr
385                 390                 395                 400
Asn Val Ile Val Ala Asn Thr Met Pro Thr His Leu Ser Asn Gly Gln
                405                 410                 415
Met Cys Glu Trp Pro Arg Pro Arg Gly Gln Ala Ala Thr Pro Glu Thr
                420                 425                 430
Pro Gln Pro Ser Pro Pro Gly Gly Ser Gly Ser Glu Pro Tyr Lys Leu
                435                 440                 445
Leu Pro Gly Ala Val Ala Thr Ile Val Lys Pro Leu Ser Ala Ile Pro
                450                 455                 460
Gln Pro Thr Ile Thr Lys Gln Glu Val Ile
465                 470
```

<210> SEQ ID NO 5
<211> LENGTH: 345
<212> TYPE: PRT
<213> ORGANISM: Homo sapiens

<400> SEQUENCE: 5

```
Met Gln Arg Leu Val Ala Trp Asp Pro Ala Cys Leu Pro Leu Pro Pro
1               5                   10                  15

Pro Pro Pro Ala Phe Lys Ser Met Glu Val Ala Asn Phe Tyr Tyr Glu
            20                  25                  30

Ala Asp Cys Leu Ala Ala Ala Tyr Gly Gly Lys Ala Ala Pro Ala Ala
        35                  40                  45

Pro Pro Ala Ala Arg Pro Gly Pro Arg Pro Pro Ala Gly Glu Leu Gly
    50                  55                  60

Ser Ile Gly Asp His Glu Arg Ala Ile Asp Phe Ser Pro Tyr Leu Glu
65                  70                  75                  80

Pro Leu Gly Ala Pro Gln Ala Pro Ala Pro Thr Ala Thr Asp Thr
                85                  90                  95

Phe Glu Ala Ala Pro Pro Ala Pro Ala Pro Ala Ser Ser Gly
                100                 105                 110

Gln His His Asp Phe Leu Ser Asp Leu Phe Ser Asp Tyr Gly Gly
            115                 120                 125

Lys Asn Cys Lys Lys Pro Ala Glu Tyr Gly Tyr Val Ser Leu Gly Arg
    130                 135                 140

Leu Gly Ala Ala Lys Gly Ala Leu His Pro Gly Cys Phe Ala Pro Leu
145                 150                 155                 160

His Pro Pro Pro Pro Pro Pro Pro Ala Glu Leu Lys Ala Glu
                165                 170                 175

Pro Gly Phe Glu Pro Ala Asp Cys Lys Arg Lys Glu Glu Ala Gly Ala
                180                 185                 190

Pro Gly Gly Gly Ala Gly Met Ala Ala Gly Phe Pro Tyr Ala Leu Arg
            195                 200                 205

Ala Tyr Leu Gly Tyr Gln Ala Val Pro Ser Gly Ser Ser Gly Ser Leu
        210                 215                 220

Ser Thr Ser Ser Ser Ser Ser Pro Pro Gly Thr Pro Ser Pro Ala Asp
225                 230                 235                 240

Ala Lys Ala Pro Pro Thr Ala Cys Tyr Ala Gly Ala Ala Pro Ala Pro
                245                 250                 255

Ser Gln Val Lys Ser Lys Ala Lys Lys Thr Val Asp Lys His Ser Asp
            260                 265                 270

Glu Tyr Lys Ile Arg Arg Glu Arg Asn Asn Ile Ala Val Arg Lys Ser
            275                 280                 285

Arg Asp Lys Ala Lys Met Arg Asn Leu Glu Thr Gln His Lys Val Leu
    290                 295                 300

Glu Leu Thr Ala Glu Asn Glu Arg Leu Gln Lys Lys Val Glu Gln Leu
305                 310                 315                 320

Ser Arg Glu Leu Ser Thr Leu Arg Asn Leu Phe Lys Gln Leu Pro Glu
                325                 330                 335

Pro Leu Leu Ala Ser Ser Gly His Cys
            340                 345
```

<210> SEQ ID NO 6
<211> LENGTH: 270
<212> TYPE: PRT
<213> ORGANISM: Homo sapiens

<400> SEQUENCE: 6

```
Met Gln Tyr Pro His Pro Gly Pro Ala Ala Gly Ala Val Gly Val Pro
1               5                   10                  15
```

```
Leu Tyr Ala Pro Thr Pro Leu Leu Gln Pro Ala His Pro Thr Pro Phe
            20                  25                  30

Tyr Ile Glu Asp Ile Leu Gly Arg Gly Pro Ala Ala Pro Thr Pro Ala
        35                  40                  45

Pro Thr Leu Pro Ser Pro Asn Ser Ser Phe Thr Ser Leu Val Ser Pro
 50                  55                  60

Tyr Arg Thr Pro Val Tyr Glu Pro Thr Pro Ile His Pro Ala Phe Ser
 65                  70                  75                  80

His His Ser Ala Ala Ala Leu Ala Ala Ala Tyr Gly Pro Gly Gly Phe
                85                  90                  95

Gly Gly Pro Leu Tyr Pro Phe Pro Arg Thr Val Asn Asp Tyr Thr His
            100                 105                 110

Ala Leu Leu Arg His Asp Pro Leu Gly Lys Pro Leu Leu Trp Ser Pro
        115                 120                 125

Phe Leu Gln Arg Pro Leu His Lys Arg Lys Gly Gly Gln Val Arg Phe
130                 135                 140

Ser Asn Asp Gln Thr Ile Glu Leu Glu Lys Lys Phe Glu Thr Gln Lys
145                 150                 155                 160

Tyr Leu Ser Pro Pro Glu Arg Lys Arg Leu Ala Lys Met Leu Gln Leu
                165                 170                 175

Ser Glu Arg Gln Val Lys Thr Trp Phe Gln Asn Arg Arg Ala Lys Trp
            180                 185                 190

Arg Arg Leu Lys Gln Glu Asn Pro Gln Ser Asn Lys Lys Glu Glu Leu
        195                 200                 205

Glu Ser Leu Asp Ser Ser Cys Asp Gln Arg Gln Asp Leu Pro Ser Glu
    210                 215                 220

Gln Asn Lys Gly Ala Ser Leu Asp Ser Ser Gln Cys Ser Pro Ser Pro
225                 230                 235                 240

Ala Ser Gln Glu Asp Leu Glu Ser Glu Ile Ser Glu Asp Ser Asp Gln
                245                 250                 255

Glu Val Asp Ile Glu Gly Asp Lys Ser Tyr Phe Asn Ala Gly
            260                 265                 270

<210> SEQ ID NO 7
<211> LENGTH: 737
<212> TYPE: PRT
<213> ORGANISM: Homo sapiens

<400> SEQUENCE: 7

Met Pro Asp His Asp Ser Thr Ala Leu Leu Ser Arg Gln Thr Lys Arg
1               5                   10                  15

Arg Arg Val Asp Ile Gly Val Lys Arg Thr Val Gly Thr Ala Ser Ala
            20                  25                  30

Phe Phe Ala Lys Ala Arg Ala Thr Phe Phe Ser Ala Met Asn Pro Gln
        35                  40                  45

Gly Ser Glu Gln Asp Val Glu Tyr Ser Val Val Gln His Ala Asp Gly
 50                  55                  60

Glu Lys Ser Asn Val Leu Arg Lys Leu Leu Lys Arg Ala Asn Ser Tyr
65                  70                  75                  80

Glu Asp Ala Met Met Pro Phe Pro Gly Ala Thr Ile Ile Ser Gln Leu
                85                  90                  95

Leu Lys Asn Asn Met Asn Lys Asn Gly Gly Thr Glu Pro Ser Phe Gln
            100                 105                 110

Ala Ser Gly Leu Ser Ser Thr Gly Ser Glu Val His Gln Glu Asp Ile
```

```
            115                 120                 125
Cys Ser Asn Ser Ser Arg Asp Ser Pro Pro Glu Cys Leu Ser Pro Phe
            130                 135                 140

Gly Arg Pro Thr Met Ser Gln Phe Asp Met Asp Arg Leu Cys Asp Glu
145                 150                 155                 160

His Leu Arg Ala Lys Arg Ala Arg Val Glu Asn Ile Ile Arg Gly Met
                165                 170                 175

Ser His Ser Pro Ser Val Ala Leu Arg Gly Asn Glu Asn Glu Arg Glu
            180                 185                 190

Met Ala Pro Gln Ser Val Ser Pro Arg Glu Ser Tyr Arg Glu Asn Lys
            195                 200                 205

Arg Lys Gln Lys Leu Pro Gln Gln Gln Gln Ser Phe Gln Gln Leu
        210                 215                 220

Val Ser Ala Arg Lys Glu Gln Lys Arg Glu Glu Arg Gln Leu Lys
225                 230                 235                 240

Gln Gln Leu Glu Asp Met Gln Lys Gln Leu Arg Gln Leu Gln Glu Lys
                245                 250                 255

Phe Tyr Gln Ile Tyr Asp Ser Thr Asp Ser Glu Asn Asp Glu Asp Gly
            260                 265                 270

Asn Leu Ser Glu Asp Ser Met Arg Ser Glu Ile Leu Asp Ala Arg Ala
            275                 280                 285

Gln Asp Ser Val Gly Arg Ser Asp Asn Glu Met Cys Glu Leu Asp Pro
            290                 295                 300

Gly Gln Phe Ile Asp Arg Ala Arg Ala Leu Ile Arg Glu Gln Glu Met
305                 310                 315                 320

Ala Glu Asn Lys Pro Lys Arg Glu Gly Asn Asn Lys Glu Arg Asp His
                325                 330                 335

Gly Pro Asn Ser Leu Gln Pro Glu Gly Lys His Leu Ala Glu Thr Leu
            340                 345                 350

Lys Gln Glu Leu Asn Thr Ala Met Ser Gln Val Val Asp Thr Val Val
            355                 360                 365

Lys Val Phe Ser Ala Lys Pro Ser Arg Gln Val Pro Gln Val Phe Pro
370                 375                 380

Pro Leu Gln Ile Pro Gln Ala Arg Phe Ala Val Asn Gly Glu Asn His
385                 390                 395                 400

Asn Phe His Thr Ala Asn Gln Arg Leu Gln Cys Phe Gly Asp Val Ile
                405                 410                 415

Ile Pro Asn Pro Leu Asp Thr Phe Gly Asn Val Gln Met Ala Ser Ser
            420                 425                 430

Thr Asp Gln Thr Glu Ala Leu Pro Leu Val Val Arg Lys Asn Ser Ser
            435                 440                 445

Asp Gln Ser Ala Ser Gly Pro Ala Ala Gly Gly His His Gln Pro Leu
            450                 455                 460

His Gln Ser Pro Leu Ser Ala Thr Thr Gly Phe Thr Thr Ser Thr Phe
465                 470                 475                 480

Arg His Pro Phe Pro Leu Pro Leu Met Ala Tyr Pro Phe Gln Ser Pro
                485                 490                 495

Leu Gly Ala Pro Ser Gly Ser Phe Ser Gly Lys Asp Arg Ala Ser Pro
            500                 505                 510

Glu Ser Leu Asp Leu Thr Arg Asp Thr Thr Ser Leu Arg Thr Lys Met
            515                 520                 525

Ser Ser His His Leu Ser His Pro Cys Ser Pro Ala His Pro Pro
            530                 535                 540
```

```
Ser Thr Ala Glu Gly Leu Ser Leu Ser Leu Ile Lys Ser Glu Cys Gly
545                 550                 555                 560

Asp Leu Gln Asp Met Ser Glu Ile Ser Pro Tyr Ser Gly Ser Ala Met
                565                 570                 575

Gln Glu Gly Leu Ser Pro Asn His Leu Lys Lys Ala Lys Leu Met Phe
            580                 585                 590

Phe Tyr Thr Arg Tyr Pro Ser Ser Asn Met Leu Lys Thr Tyr Phe Ser
        595                 600                 605

Asp Val Lys Phe Asn Arg Cys Ile Thr Ser Gln Leu Ile Lys Trp Phe
    610                 615                 620

Ser Asn Phe Arg Glu Phe Tyr Tyr Ile Gln Met Glu Lys Tyr Ala Arg
625                 630                 635                 640

Gln Ala Ile Asn Asp Gly Val Thr Ser Thr Glu Glu Leu Ser Ile Thr
                645                 650                 655

Arg Asp Cys Glu Leu Tyr Arg Ala Leu Asn Met His Tyr Asn Lys Ala
                660                 665                 670

Asn Asp Phe Glu Val Pro Glu Arg Phe Leu Glu Val Ala Gln Ile Thr
            675                 680                 685

Leu Arg Glu Phe Phe Asn Ala Ile Ile Ala Gly Lys Asp Val Asp Pro
        690                 695                 700

Ser Trp Lys Lys Ala Ile Tyr Lys Val Ile Cys Lys Leu Asp Ser Glu
705                 710                 715                 720

Val Pro Glu Ile Phe Lys Ser Pro Asn Cys Leu Gln Glu Leu Leu His
                725                 730                 735

Glu

<210> SEQ ID NO 8
<211> LENGTH: 479
<212> TYPE: PRT
<213> ORGANISM: Homo sapiens

<400> SEQUENCE: 8

Met Arg Gln Pro Pro Gly Glu Ser Asp Met Ala Val Ser Asp Ala Leu
1               5                   10                  15

Leu Pro Ser Phe Ser Thr Phe Ala Ser Gly Pro Ala Gly Arg Glu Lys
            20                  25                  30

Thr Leu Arg Gln Ala Gly Ala Pro Asn Asn Arg Trp Arg Glu Glu Leu
        35                  40                  45

Ser His Met Lys Arg Leu Pro Pro Val Leu Pro Gly Arg Pro Tyr Asp
    50                  55                  60

Leu Ala Ala Ala Thr Val Ala Thr Asp Leu Glu Ser Gly Gly Ala Gly
65                  70                  75                  80

Ala Ala Cys Gly Gly Ser Asn Leu Ala Pro Leu Pro Arg Arg Glu Thr
                85                  90                  95

Glu Glu Phe Asn Asp Leu Leu Asp Leu Asp Phe Ile Leu Ser Asn Ser
                100                 105                 110

Leu Thr His Pro Pro Glu Ser Val Ala Ala Thr Val Ser Ser Ser Ala
        115                 120                 125

Ser Ala Ser Ser Ser Ser Ser Pro Ser Ser Gly Pro Ala Ser Ala
    130                 135                 140

Pro Ser Thr Cys Ser Phe Thr Tyr Pro Ile Arg Ala Gly Asn Asp Pro
145                 150                 155                 160

Gly Val Ala Pro Gly Gly Thr Gly Gly Gly Leu Leu Tyr Gly Arg Glu
                165                 170                 175
```

```
Ser Ala Pro Pro Pro Thr Ala Pro Phe Asn Leu Ala Asp Ile Asn Asp
            180                 185                 190

Val Ser Pro Ser Gly Gly Phe Val Ala Glu Leu Leu Arg Pro Glu Leu
        195                 200                 205

Asp Pro Val Tyr Ile Pro Pro Gln Gln Pro Gln Pro Pro Gly Gly Gly
210                 215                 220

Leu Met Gly Lys Phe Val Leu Lys Ala Ser Leu Ser Ala Pro Gly Ser
225                 230                 235                 240

Glu Tyr Gly Ser Pro Ser Val Ile Ser Val Ser Lys Gly Ser Pro Asp
                245                 250                 255

Gly Ser His Pro Val Val Val Ala Pro Tyr Asn Gly Gly Pro Pro Arg
            260                 265                 270

Thr Cys Pro Lys Ile Lys Gln Glu Ala Val Ser Ser Cys Thr His Leu
        275                 280                 285

Gly Ala Gly Pro Pro Leu Ser Asn Gly His Arg Pro Ala Ala His Asp
290                 295                 300

Phe Pro Leu Gly Arg Gln Leu Pro Ser Arg Thr Thr Pro Thr Leu Gly
305                 310                 315                 320

Leu Glu Glu Val Leu Ser Ser Arg Asp Cys His Pro Ala Leu Pro Leu
                325                 330                 335

Pro Pro Gly Phe His Pro His Pro Gly Pro Asn Tyr Pro Ser Phe Leu
            340                 345                 350

Pro Asp Gln Met Gln Pro Gln Val Pro Pro Leu His Tyr Gln Glu Leu
        355                 360                 365

Met Pro Pro Gly Ser Cys Met Pro Glu Glu Pro Lys Pro Lys Arg Gly
370                 375                 380

Arg Arg Ser Trp Pro Arg Lys Arg Thr Ala Thr His Thr Cys Asp Tyr
385                 390                 395                 400

Ala Gly Cys Gly Lys Thr Tyr Thr Lys Ser Ser His Leu Lys Ala His
                405                 410                 415

Leu Arg Thr His Thr Gly Glu Lys Pro Tyr His Cys Asp Trp Asp Gly
            420                 425                 430

Cys Gly Trp Lys Phe Ala Arg Ser Asp Glu Leu Thr Arg His Tyr Arg
        435                 440                 445

Lys His Thr Gly His Arg Pro Phe Gln Cys Gln Lys Cys Asp Arg Ala
450                 455                 460

Phe Ser Arg Ser Asp His Leu Ala Leu His Met Lys Arg His Phe
465                 470                 475

<210> SEQ ID NO 9
<211> LENGTH: 631
<212> TYPE: PRT
<213> ORGANISM: Homo sapiens

<400> SEQUENCE: 9

Met Val Ser Lys Leu Ser Gln Leu Gln Thr Glu Leu Leu Ala Ala Leu
1               5                   10                  15

Leu Glu Ser Gly Leu Ser Lys Glu Ala Leu Ile Gln Ala Leu Gly Glu
            20                  25                  30

Pro Gly Pro Tyr Leu Leu Ala Gly Glu Gly Pro Leu Asp Lys Gly Glu
        35                  40                  45

Ser Cys Gly Gly Gly Arg Gly Glu Leu Ala Glu Leu Pro Asn Gly Leu
    50                  55                  60

Gly Glu Thr Arg Gly Ser Glu Asp Glu Thr Asp Asp Asp Gly Glu Asp
```

```
            65                  70                  75                  80

Phe Thr Pro Pro Ile Leu Lys Glu Leu Glu Asn Leu Ser Pro Glu Glu
                        85                  90                  95

Ala Ala His Gln Lys Ala Val Val Glu Thr Leu Leu Gln Glu Asp Pro
                        100                 105                 110

Trp Arg Val Ala Lys Met Val Lys Ser Tyr Leu Gln Gln His Asn Ile
                        115                 120                 125

Pro Gln Arg Glu Val Val Asp Thr Thr Gly Leu Asn Gln Ser His Leu
                        130                 135                 140

Ser Gln His Leu Asn Lys Gly Thr Pro Met Lys Thr Gln Lys Arg Ala
        145                 150                 155                 160

Ala Leu Tyr Thr Trp Tyr Val Arg Lys Gln Arg Glu Val Ala Gln Gln
                        165                 170                 175

Phe Thr His Ala Gly Gln Gly Gly Leu Ile Glu Glu Pro Thr Gly Asp
                        180                 185                 190

Glu Leu Pro Thr Lys Lys Gly Arg Arg Asn Arg Phe Lys Trp Gly Pro
                        195                 200                 205

Ala Ser Gln Gln Ile Leu Phe Gln Ala Tyr Glu Arg Gln Lys Asn Pro
        210                 215                 220

Ser Lys Glu Glu Arg Glu Thr Leu Val Glu Glu Cys Asn Arg Ala Glu
        225                 230                 235                 240

Cys Ile Gln Arg Gly Val Ser Pro Ser Gln Ala Gln Gly Leu Gly Ser
                        245                 250                 255

Asn Leu Val Thr Glu Val Arg Val Tyr Asn Trp Phe Ala Asn Arg Arg
                        260                 265                 270

Lys Glu Glu Ala Phe Arg His Lys Leu Ala Met Asp Thr Tyr Ser Gly
                        275                 280                 285

Pro Pro Pro Gly Pro Gly Pro Gly Pro Ala Leu Pro Ala His Ser Ser
                        290                 295                 300

Pro Gly Leu Pro Pro Ala Leu Ser Pro Ser Lys Val His Gly Val
        305                 310                 315                 320

Arg Tyr Gly Gln Pro Ala Thr Ser Glu Thr Ala Glu Val Pro Ser Ser
                        325                 330                 335

Ser Gly Gly Pro Leu Val Thr Val Ser Thr Pro Leu His Gln Val Ser
                        340                 345                 350

Pro Thr Gly Leu Glu Pro Ser His Ser Leu Leu Ser Thr Glu Ala Lys
                        355                 360                 365

Leu Val Ser Ala Ala Gly Gly Pro Leu Pro Pro Val Ser Thr Leu Thr
                        370                 375                 380

Ala Leu His Ser Leu Glu Gln Thr Ser Pro Gly Leu Asn Gln Gln Pro
        385                 390                 395                 400

Gln Asn Leu Ile Met Ala Ser Leu Pro Gly Val Met Thr Ile Gly Pro
                        405                 410                 415

Gly Glu Pro Ala Ser Leu Gly Pro Thr Phe Thr Asn Thr Gly Ala Ser
                        420                 425                 430

Thr Leu Val Ile Gly Leu Ala Ser Thr Gln Ala Gln Ser Val Pro Val
                        435                 440                 445

Ile Asn Ser Met Gly Ser Ser Leu Thr Thr Leu Gln Pro Val Gln Phe
                        450                 455                 460

Ser Gln Pro Leu His Pro Ser Tyr Gln Gln Pro Leu Met Pro Pro Val
        465                 470                 475                 480

Gln Ser His Val Thr Gln Ser Pro Phe Met Ala Thr Met Ala Gln Leu
                        485                 490                 495
```

```
Gln Ser Pro His Ala Leu Tyr Ser His Lys Pro Glu Val Ala Gln Tyr
            500                 505                 510

Thr His Thr Gly Leu Leu Pro Gln Thr Met Leu Ile Thr Asp Thr Thr
            515                 520                 525

Asn Leu Ser Ala Leu Ala Ser Leu Thr Pro Thr Lys Gln Val Phe Thr
            530                 535                 540

Ser Asp Thr Glu Ala Ser Ser Glu Ser Gly Leu His Thr Pro Ala Ser
545                 550                 555                 560

Gln Ala Thr Thr Leu His Val Pro Ser Gln Asp Pro Ala Gly Ile Gln
            565                 570                 575

His Leu Gln Pro Ala His Arg Leu Ser Ala Ser Pro Thr Val Ser Ser
            580                 585                 590

Ser Ser Leu Val Leu Tyr Gln Ser Ser Asp Ser Ser Asn Gly Gln Ser
            595                 600                 605

His Leu Leu Pro Ser Asn His Ser Val Ile Glu Thr Phe Ile Ser Thr
            610                 615                 620

Gln Met Ala Ser Ser Ser Gln
625                 630

<210> SEQ ID NO 10
<211> LENGTH: 708
<212> TYPE: PRT
<213> ORGANISM: Homo sapiens

<400> SEQUENCE: 10

Met Asp Lys Val Leu Asn Arg Glu Glu Ser Leu Gln Leu Met Asp Leu
1               5                   10                  15

Leu Gly Leu Glu Arg Ser Ala Trp Gly Asn Ile Pro Leu Met Arg Lys
            20                  25                  30

Ala Tyr Leu Lys Lys Cys Lys Glu Phe His Pro Asp Lys Gly Gly Asp
            35                  40                  45

Glu Glu Lys Met Lys Lys Met Asn Thr Leu Tyr Lys Lys Met Glu Asp
        50                  55                  60

Gly Val Lys Tyr Ala His Gln Pro Asp Phe Gly Gly Phe Trp Asp Ala
65              70                  75                  80

Thr Glu Ile Pro Thr Tyr Gly Thr Asp Glu Trp Glu Gln Trp Trp Asn
            85                  90                  95

Ala Phe Asn Glu Glu Asn Leu Phe Cys Ser Glu Met Pro Ser Ser
            100                 105                 110

Asp Asp Glu Ala Thr Ala Asp Ser Gln His Ser Thr Pro Pro Lys Lys
            115                 120                 125

Lys Arg Lys Val Glu Asp Pro Lys Asp Phe Pro Ser Glu Leu Leu Ser
        130                 135                 140

Phe Leu Ser His Ala Val Phe Ser Asn Arg Thr Leu Ala Cys Phe Ala
145                 150                 155                 160

Ile Tyr Thr Thr Lys Glu Lys Ala Ala Leu Leu Tyr Lys Lys Ile Met
            165                 170                 175

Glu Lys Tyr Ser Val Thr Phe Ile Ser Arg His Asn Ser Tyr Asn His
            180                 185                 190

Asn Ile Leu Phe Phe Leu Thr Pro His Arg His Arg Val Ser Ala Ile
            195                 200                 205

Asn Asn Tyr Ala Gln Lys Leu Cys Thr Phe Ser Phe Leu Ile Cys Lys
        210                 215                 220

Gly Val Asn Lys Glu Tyr Leu Met Tyr Ser Ala Leu Thr Arg Asp Pro
```

```
            225                 230                 235                 240
        Phe Ser Val Ile Glu Glu Ser Leu Pro Gly Gly Leu Lys Glu His Asp
                            245                 250                 255
        Phe Asn Pro Glu Glu Ala Glu Glu Thr Lys Gln Val Ser Trp Lys Leu
                            260                 265                 270
        Val Thr Glu Tyr Ala Met Glu Thr Lys Cys Asp Val Leu Leu Leu
                            275                 280                 285
        Leu Gly Met Tyr Leu Glu Phe Gln Tyr Ser Phe Glu Met Cys Leu Lys
                    290                 295                 300
        Cys Ile Lys Lys Glu Gln Pro Ser His Tyr Lys Tyr His Glu Lys His
        305                 310                 315                 320
        Tyr Ala Asn Ala Ala Ile Phe Ala Asp Ser Lys Asn Gln Lys Thr Ile
                            325                 330                 335
        Cys Gln Gln Ala Val Asp Thr Val Leu Ala Lys Lys Arg Val Asp Ser
                            340                 345                 350
        Leu Gln Leu Thr Arg Glu Gln Met Leu Thr Asn Arg Phe Asn Asp Leu
                    355                 360                 365
        Leu Asp Arg Met Asp Ile Met Phe Gly Ser Thr Gly Ser Ala Asp Ile
                370                 375                 380
        Glu Glu Trp Met Ala Gly Val Ala Trp Leu His Cys Leu Leu Pro Lys
        385                 390                 395                 400
        Met Asp Ser Val Val Tyr Asp Phe Leu Lys Cys Met Val Tyr Asn Ile
                            405                 410                 415
        Pro Lys Lys Arg Tyr Trp Leu Phe Lys Gly Pro Ile Asp Ser Gly Lys
                            420                 425                 430
        Thr Thr Leu Ala Ala Ala Leu Leu Glu Leu Cys Gly Gly Lys Ala Leu
                    435                 440                 445
        Asn Val Asn Leu Pro Leu Asp Arg Leu Asn Phe Glu Leu Gly Val Ala
                450                 455                 460
        Ile Asp Gln Phe Leu Val Val Phe Glu Asp Val Lys Gly Thr Gly Gly
        465                 470                 475                 480
        Glu Ser Arg Asp Leu Pro Ser Gly Gln Gly Ile Asn Asn Leu Asp Asn
                            485                 490                 495
        Leu Arg Asp Tyr Leu Asp Gly Ser Val Lys Val Asn Leu Glu Lys Lys
                            500                 505                 510
        His Leu Asn Lys Arg Thr Gln Ile Phe Pro Pro Gly Ile Val Thr Met
                    515                 520                 525
        Asn Glu Tyr Ser Val Pro Lys Thr Leu Gln Ala Arg Phe Val Lys Gln
                530                 535                 540
        Ile Asp Phe Arg Pro Lys Asp Tyr Leu Lys His Cys Leu Glu Arg Ser
        545                 550                 555                 560
        Glu Phe Leu Leu Glu Lys Arg Ile Ile Gln Ser Gly Ile Ala Leu Leu
                            565                 570                 575
        Leu Met Leu Ile Trp Tyr Arg Pro Val Ala Glu Phe Ala Gln Ser Ile
                            580                 585                 590
        Gln Ser Arg Ile Val Glu Trp Lys Glu Arg Leu Asp Lys Glu Phe Ser
                    595                 600                 605
        Leu Ser Val Tyr Gln Lys Met Lys Phe Asn Val Ala Met Gly Ile Gly
                610                 615                 620
        Val Leu Asp Trp Leu Arg Asn Ser Asp Asp Asp Glu Asp Ser Gln
        625                 630                 635                 640
        Glu Asn Ala Asp Lys Asn Glu Asp Gly Gly Glu Lys Asn Met Glu Asp
                            645                 650                 655
```

Ser Gly His Glu Thr Gly Ile Asp Ser Gln Ser Gln Gly Ser Phe Gln
            660                 665                 670

Ala Pro Gln Ser Ser Gln Ser Val His Asp His Asn Gln Pro Tyr His
            675                 680                 685

Ile Cys Arg Gly Phe Thr Cys Phe Lys Lys Pro Pro Thr Pro Pro Pro
690                 695                 700

Glu Pro Glu Thr
705

<210> SEQ ID NO 11
<211> LENGTH: 1139
<212> TYPE: PRT
<213> ORGANISM: Homo sapiens

<400> SEQUENCE: 11

Met Pro Ser Gly Gly Asp Gln Ser Pro Pro Pro Pro Pro Pro Pro Pro
1               5                   10                  15

Ala Ala Ala Ala Ser Asp Glu Glu Glu Asp Asp Gly Glu Ala Glu
            20                  25                  30

Asp Ala Ala Pro Pro Ala Glu Ser Pro Thr Pro Gln Ile Gln Gln Arg
            35                  40                  45

Phe Asp Glu Leu Cys Ser Arg Leu Asn Met Asp Glu Ala Ala Arg Ala
50                  55                  60

Glu Ala Trp Asp Ser Tyr Arg Ser Met Ser Glu Ser Tyr Thr Leu Glu
65                  70                  75                  80

Gly Asn Asp Leu His Trp Leu Ala Cys Ala Leu Tyr Val Ala Cys Arg
            85                  90                  95

Lys Ser Val Pro Thr Val Ser Lys Gly Thr Val Glu Gly Asn Tyr Val
            100                 105                 110

Ser Leu Thr Arg Ile Leu Lys Cys Ser Glu Gln Ser Leu Ile Glu Phe
            115                 120                 125

Phe Asn Lys Met Lys Lys Trp Glu Asp Met Ala Asn Leu Pro Pro His
            130                 135                 140

Phe Arg Glu Arg Thr Glu Arg Leu Glu Arg Asn Phe Thr Val Ser Ala
145                 150                 155                 160

Val Ile Phe Lys Lys Tyr Glu Pro Ile Phe Gln Asp Ile Phe Lys Tyr
            165                 170                 175

Pro Gln Glu Glu Gln Pro Arg Gln Gln Arg Gly Arg Lys Gln Arg Arg
            180                 185                 190

Gln Pro Cys Thr Val Ser Glu Ile Phe His Phe Cys Trp Val Leu Phe
            195                 200                 205

Ile Tyr Ala Lys Gly Asn Phe Pro Met Ile Ser Asp Asp Leu Val Asn
            210                 215                 220

Ser Tyr His Leu Leu Leu Cys Ala Leu Asp Leu Val Tyr Gly Asn Ala
225                 230                 235                 240

Leu Gln Cys Ser Asn Arg Lys Glu Leu Val Asn Pro Asn Phe Lys Gly
            245                 250                 255

Leu Ser Glu Asp Phe His Ala Lys Asp Ser Lys Pro Ser Ser Asp Pro
            260                 265                 270

Pro Cys Ile Ile Glu Lys Leu Cys Ser Leu His Asp Gly Leu Val Leu
            275                 280                 285

Glu Ala Lys Gly Ile Lys Glu His Phe Trp Lys Pro Tyr Ile Arg Lys
            290                 295                 300

Leu Tyr Glu Lys Lys Leu Leu Lys Gly Lys Glu Glu Asn Leu Thr Gly

```
305                 310                 315                 320
Phe Leu Glu Pro Gly Asn Phe Gly Ser Phe Lys Ala Ile Asn Lys
                325                 330                 335

Ala Tyr Glu Glu Tyr Val Leu Ser Val Gly Asn Leu Asp Glu Arg Ile
                340                 345                 350

Phe Leu Gly Glu Asp Ala Glu Glu Ile Gly Thr Leu Ser Arg Cys
                355                 360                 365

Leu Asn Ala Gly Ser Gly Thr Glu Thr Ala Glu Arg Val Gln Met Lys
370                 375                 380

Asn Ile Leu Gln Gln His Phe Asp Lys Ser Lys Ala Leu Arg Ile Ser
385                 390                 395                 400

Thr Pro Leu Thr Gly Val Arg Tyr Ile Lys Glu Asn Ser Pro Cys Val
                405                 410                 415

Thr Pro Val Ser Thr Ala Thr His Ser Leu Ser Arg Leu His Thr Met
                420                 425                 430

Leu Thr Gly Leu Arg Asn Ala Pro Ser Glu Lys Leu Glu Gln Ile Leu
                435                 440                 445

Arg Thr Cys Ser Arg Asp Pro Thr Gln Ala Ile Ala Asn Arg Leu Lys
450                 455                 460

Glu Met Phe Glu Ile Tyr Ser Gln His Phe Gln Pro Asp Glu Asp Phe
465                 470                 475                 480

Ser Asn Cys Ala Lys Glu Ile Ala Ser Lys His Phe Arg Phe Ala Glu
                485                 490                 495

Met Leu Tyr Tyr Lys Val Leu Glu Ser Val Ile Glu Gln Glu Gln Lys
                500                 505                 510

Arg Leu Gly Asp Met Asp Leu Ser Gly Ile Leu Glu Gln Asp Ala Phe
                515                 520                 525

His Arg Ser Leu Leu Ala Cys Cys Leu Glu Val Val Thr Phe Ser Tyr
                530                 535                 540

Lys Pro Pro Gly Asn Phe Pro Phe Ile Thr Glu Ile Phe Asp Val Pro
545                 550                 555                 560

Leu Tyr His Phe Tyr Lys Val Ile Glu Val Phe Ile Arg Ala Glu Asp
                565                 570                 575

Gly Leu Cys Arg Glu Val Val Lys His Leu Asn Gln Ile Glu Glu Gln
                580                 585                 590

Ile Leu Asp His Leu Ala Trp Lys Pro Glu Ser Pro Leu Trp Glu Lys
                595                 600                 605

Ile Arg Asp Asn Glu Asn Arg Val Pro Thr Cys Glu Glu Val Met Pro
610                 615                 620

Pro Gln Asn Leu Glu Arg Ala Asp Glu Ile Cys Ile Ala Gly Ser Pro
625                 630                 635                 640

Leu Thr Pro Arg Arg Val Thr Glu Val Arg Ala Asp Thr Gly Gly Leu
                645                 650                 655

Gly Arg Ser Ile Thr Ser Pro Thr Thr Leu Tyr Asp Arg Tyr Ser Ser
                660                 665                 670

Pro Pro Ala Ser Thr Thr Arg Arg Leu Phe Val Glu Asn Asp Ser
                675                 680                 685

Pro Ser Asp Gly Gly Thr Pro Gly Arg Met Pro Gln Pro Leu Val
                690                 695                 700

Asn Ala Val Pro Val Gln Asn Val Ser Gly Glu Thr Val Ser Val Thr
705                 710                 715                 720

Pro Val Pro Gly Gln Thr Leu Val Thr Met Ala Thr Ala Thr Val Thr
                725                 730                 735
```

-continued

```
Ala Asn Asn Gly Gln Thr Val Thr Ile Pro Val Gln Gly Ile Ala Asn
            740                 745                 750

Glu Asn Gly Gly Ile Thr Phe Phe Pro Val Gln Val Asn Val Gly Gly
            755                 760                 765

Gln Ala Gln Ala Val Thr Gly Ser Ile Gln Pro Leu Ser Ala Gln Ala
            770                 775                 780

Leu Ala Gly Ser Leu Ser Ser Gln Gln Val Thr Gly Thr Thr Leu Gln
785                 790                 795                 800

Val Pro Gly Gln Val Ala Ile Gln Gln Ile Ser Pro Gly Gln Gln
            805                 810                 815

Gln Lys Gln Gly Gln Ser Val Thr Ser Ser Asn Arg Pro Arg Lys
            820                 825                 830

Thr Ser Ser Leu Ser Leu Phe Phe Arg Lys Val Tyr His Leu Ala Ala
            835                 840                 845

Val Arg Leu Arg Asp Leu Cys Ala Lys Leu Asp Ile Ser Asp Glu Leu
850                 855                 860

Arg Lys Lys Ile Trp Thr Cys Phe Glu Phe Ser Ile Ile Gln Cys Pro
865                 870                 875                 880

Glu Leu Met Met Asp Arg His Leu Asp Gln Leu Leu Met Cys Ala Ile
            885                 890                 895

Tyr Val Met Ala Lys Val Thr Lys Glu Asp Lys Ser Phe Gln Asn Ile
            900                 905                 910

Met Arg Cys Tyr Arg Thr Gln Pro Gln Ala Arg Ser Gln Val Tyr Arg
            915                 920                 925

Ser Val Leu Ile Lys Gly Lys Arg Lys Arg Arg Asn Ser Gly Ser Ser
            930                 935                 940

Asp Ser Arg Ser His Gln Asn Ser Pro Thr Glu Leu Asn Lys Asp Arg
945                 950                 955                 960

Thr Ser Arg Asp Ser Ser Pro Val Met Arg Ser Ser Ser Thr Leu Pro
                965                 970                 975

Val Pro Gln Pro Ser Ser Ala Pro Pro Thr Pro Thr Arg Leu Thr Gly
            980                 985                 990

Ala Asn Ser Asp Met Glu Glu Glu Glu Arg Gly Asp Leu Ile Gln Phe
            995                 1000                1005

Tyr Asn Asn Ile Tyr Ile Lys Gln Ile Lys Thr Phe Ala Met Lys
        1010                1015                1020

Tyr Ser Gln Ala Asn Met Asp Ala Pro Pro Leu Ser Pro Tyr Pro
        1025                1030                1035

Phe Val Arg Thr Gly Ser Pro Arg Arg Ile Gln Leu Ser Gln Asn
        1040                1045                1050

His Pro Val Tyr Ile Ser Pro His Lys Asn Glu Thr Met Leu Ser
        1055                1060                1065

Pro Arg Glu Lys Ile Phe Tyr Tyr Phe Ser Asn Ser Pro Ser Lys
        1070                1075                1080

Arg Leu Arg Glu Ile Asn Ser Met Ile Arg Thr Gly Glu Thr Pro
        1085                1090                1095

Thr Lys Lys Arg Gly Ile Leu Leu Glu Asp Gly Ser Glu Ser Pro
        1100                1105                1110

Ala Lys Arg Ile Cys Pro Glu Asn His Ser Ala Leu Leu Arg Arg
        1115                1120                1125

Leu Gln Asp Val Ala Asn Asp Arg Gly Ser His
        1130                1135
```

<210> SEQ ID NO 12
<211> LENGTH: 928
<212> TYPE: PRT
<213> ORGANISM: Homo sapiens

<400> SEQUENCE: 12

Met Pro Pro Lys Thr Pro Arg Lys Thr Ala Thr Ala Ala Ala Ala Ala
1               5                   10                  15

Ala Ala Glu Pro Pro Ala Pro Pro Pro Pro Pro Pro Glu Glu Asp
            20                  25                  30

Pro Glu Gln Asp Ser Gly Pro Glu Asp Leu Pro Leu Val Arg Leu Glu
        35                  40                  45

Phe Glu Glu Thr Glu Glu Pro Asp Phe Thr Ala Leu Cys Gln Lys Leu
    50                  55                  60

Lys Ile Pro Asp His Val Arg Glu Arg Ala Trp Leu Thr Trp Glu Lys
65                  70                  75                  80

Val Ser Ser Val Asp Gly Val Leu Gly Gly Tyr Ile Gln Lys Lys Lys
                85                  90                  95

Glu Leu Trp Gly Ile Cys Ile Phe Ile Ala Ala Val Asp Leu Asp Glu
            100                 105                 110

Met Ser Phe Thr Phe Thr Glu Leu Gln Lys Asn Ile Glu Ile Ser Val
        115                 120                 125

His Lys Phe Phe Asn Leu Leu Lys Glu Ile Asp Thr Ser Thr Lys Val
    130                 135                 140

Asp Asn Ala Met Ser Arg Leu Leu Lys Lys Tyr Asp Val Leu Phe Ala
145                 150                 155                 160

Leu Phe Ser Lys Leu Glu Arg Thr Cys Glu Leu Ile Tyr Leu Thr Gln
                165                 170                 175

Pro Ser Ser Ser Ile Ser Thr Glu Ile Asn Ser Ala Leu Val Leu Lys
            180                 185                 190

Val Ser Trp Ile Thr Phe Leu Leu Ala Lys Gly Glu Val Leu Gln Met
        195                 200                 205

Glu Asp Asp Leu Val Ile Ser Phe Gln Leu Met Leu Cys Val Leu Asp
    210                 215                 220

Tyr Phe Ile Lys Leu Ser Pro Pro Met Leu Leu Lys Glu Pro Tyr Lys
225                 230                 235                 240

Thr Ala Val Ile Pro Ile Asn Gly Ser Pro Arg Thr Pro Arg Arg Gly
                245                 250                 255

Gln Asn Arg Ser Ala Arg Ile Ala Lys Gln Leu Glu Asn Asp Thr Arg
            260                 265                 270

Ile Ile Glu Val Leu Cys Lys Glu His Glu Cys Asn Ile Asp Glu Val
    275                 280                 285

Lys Asn Val Tyr Phe Lys Asn Phe Ile Pro Phe Met Asn Ser Leu Gly
290                 295                 300

Leu Val Thr Ser Asn Gly Leu Pro Glu Val Glu Asn Leu Ser Lys Arg
305                 310                 315                 320

Tyr Glu Glu Ile Tyr Leu Lys Asn Lys Asp Leu Asp Ala Arg Leu Phe
                325                 330                 335

Leu Asp His Asp Lys Thr Leu Gln Thr Asp Ser Ile Asp Ser Phe Glu
            340                 345                 350

Thr Gln Arg Thr Pro Arg Lys Ser Asn Leu Asp Glu Glu Val Asn Val
        355                 360                 365

Ile Pro Pro His Thr Pro Val Arg Thr Val Met Asn Thr Ile Gln Gln
    370                 375                 380

```
Leu Met Met Ile Leu Asn Ser Ala Ser Asp Gln Pro Ser Glu Asn Leu
385                 390                 395                 400

Ile Ser Tyr Phe Asn Asn Cys Thr Val Asn Pro Lys Glu Ser Ile Leu
                405                 410                 415

Lys Arg Val Lys Asp Ile Gly Tyr Ile Phe Lys Glu Lys Phe Ala Lys
                420                 425                 430

Ala Val Gly Gln Gly Cys Val Glu Ile Gly Ser Gln Arg Tyr Lys Leu
            435                 440                 445

Gly Val Arg Leu Tyr Tyr Arg Val Met Glu Ser Met Leu Lys Ser Glu
        450                 455                 460

Glu Glu Arg Leu Ser Ile Gln Asn Phe Ser Lys Leu Leu Asn Asp Asn
465                 470                 475                 480

Ile Phe His Met Ser Leu Leu Ala Cys Ala Leu Glu Val Val Met Ala
                485                 490                 495

Thr Tyr Ser Arg Ser Thr Ser Gln Asn Leu Asp Ser Gly Thr Asp Leu
                500                 505                 510

Ser Phe Pro Trp Ile Leu Asn Val Leu Asn Leu Lys Ala Phe Asp Phe
            515                 520                 525

Tyr Lys Val Ile Glu Ser Phe Ile Lys Ala Gly Asn Leu Thr Arg
530                 535                 540

Glu Met Ile Lys His Leu Glu Arg Cys Glu His Arg Ile Met Glu Ser
545                 550                 555                 560

Leu Ala Trp Leu Ser Asp Ser Pro Leu Phe Asp Leu Ile Lys Gln Ser
                565                 570                 575

Lys Asp Arg Glu Gly Pro Thr Asp His Leu Glu Ser Ala Cys Pro Leu
                580                 585                 590

Asn Leu Pro Leu Gln Asn Asn His Thr Ala Ala Asp Met Tyr Leu Ser
            595                 600                 605

Pro Val Arg Ser Pro Lys Lys Lys Gly Ser Thr Thr Arg Val Asn Ser
        610                 615                 620

Thr Ala Asn Ala Glu Thr Gln Ala Thr Ser Ala Phe Gln Thr Gln Lys
625                 630                 635                 640

Pro Leu Lys Ser Thr Ser Leu Ser Leu Phe Tyr Lys Lys Val Tyr Arg
                645                 650                 655

Leu Ala Tyr Leu Arg Leu Asn Thr Leu Cys Glu Arg Leu Leu Ser Glu
                660                 665                 670

His Pro Glu Leu Glu His Ile Ile Trp Thr Leu Phe Gln His Thr Leu
            675                 680                 685

Gln Asn Glu Tyr Glu Leu Met Arg Asp Arg His Leu Asp Gln Ile Met
        690                 695                 700

Met Cys Ser Met Tyr Gly Ile Cys Lys Val Lys Asn Ile Asp Leu Lys
705                 710                 715                 720

Phe Lys Ile Ile Val Thr Ala Tyr Lys Asp Leu Pro His Ala Val Gln
                725                 730                 735

Glu Thr Phe Lys Arg Val Leu Ile Lys Glu Glu Tyr Asp Ser Ile
                740                 745                 750

Ile Val Phe Tyr Asn Ser Val Phe Met Gln Arg Leu Lys Thr Asn Ile
            755                 760                 765

Leu Gln Tyr Ala Ser Thr Arg Pro Pro Thr Leu Ser Pro Ile Pro His
        770                 775                 780

Ile Pro Arg Ser Pro Tyr Lys Phe Pro Ser Ser Pro Leu Arg Ile Pro
785                 790                 795                 800
```

```
Gly Gly Asn Ile Tyr Ile Ser Pro Leu Lys Ser Pro Tyr Lys Ile Ser
                805                 810                 815

Glu Gly Leu Pro Thr Pro Thr Lys Met Thr Pro Arg Ser Arg Ile Leu
            820                 825                 830

Val Ser Ile Gly Glu Ser Phe Gly Thr Ser Glu Lys Phe Gln Lys Ile
        835                 840                 845

Asn Gln Met Val Cys Asn Ser Asp Arg Val Leu Lys Arg Ser Ala Glu
    850                 855                 860

Gly Ser Asn Pro Pro Lys Pro Leu Lys Lys Leu Arg Phe Asp Ile Glu
865                 870                 875                 880

Gly Ser Asp Glu Ala Asp Gly Ser Lys His Leu Pro Gly Glu Ser Lys
                885                 890                 895

Phe Gln Gln Lys Leu Ala Glu Met Thr Ser Thr Arg Thr Arg Met Gln
            900                 905                 910

Lys Gln Lys Met Asn Asp Ser Met Asp Thr Ser Asn Lys Glu Glu Lys
        915                 920                 925

<210> SEQ ID NO 13
<211> LENGTH: 1068
<212> TYPE: PRT
<213> ORGANISM: Homo sapiens

<400> SEQUENCE: 13

Met Phe Glu Asp Lys Pro His Ala Glu Gly Ala Ala Val Val Ala Ala
1               5                   10                  15

Ala Gly Glu Ala Leu Gln Ala Leu Cys Gln Glu Leu Asn Leu Asp Glu
            20                  25                  30

Gly Ser Ala Ala Glu Ala Leu Asp Asp Phe Thr Ala Ile Arg Gly Asn
        35                  40                  45

Tyr Ser Leu Glu Gly Glu Val Thr His Trp Leu Ala Cys Ser Leu Tyr
    50                  55                  60

Val Ala Cys Arg Lys Ser Ile Ile Pro Thr Val Gly Lys Gly Ile Met
65                  70                  75                  80

Glu Gly Asn Cys Val Ser Leu Thr Arg Ile Leu Arg Ser Ala Lys Leu
                85                  90                  95

Ser Leu Ile Gln Phe Phe Ser Lys Met Lys Lys Trp Met Asp Met Ser
            100                 105                 110

Asn Leu Pro Gln Glu Phe Arg Glu Arg Ile Glu Arg Leu Glu Arg Asn
        115                 120                 125

Phe Glu Val Ser Thr Val Ile Phe Lys Lys Tyr Glu Pro Ile Phe Leu
    130                 135                 140

Asp Ile Phe Gln Asn Pro Tyr Glu Glu Pro Pro Lys Leu Pro Arg Ser
145                 150                 155                 160

Arg Lys Gln Arg Arg Ile Pro Cys Ser Val Lys Asp Leu Phe Asn Phe
                165                 170                 175

Cys Trp Thr Leu Phe Val Tyr Thr Lys Gly Asn Phe Arg Met Ile Gly
            180                 185                 190

Asp Asp Leu Val Asn Ser Tyr His Leu Leu Leu Cys Cys Leu Asp Leu
        195                 200                 205

Ile Phe Ala Asn Ala Ile Met Cys Pro Asn Arg Gln Asp Leu Leu Asn
    210                 215                 220

Pro Ser Phe Lys Gly Leu Pro Ser Asp Phe His Thr Ala Asp Phe Thr
225                 230                 235                 240

Ala Ser Glu Glu Pro Pro Cys Ile Ile Ala Val Leu Cys Glu Leu His
                245                 250                 255
```

-continued

Asp Gly Leu Leu Val Glu Ala Lys Gly Ile Lys Glu His Tyr Phe Lys
            260                 265                 270

Pro Tyr Ile Ser Lys Leu Phe Asp Arg Lys Ile Leu Lys Gly Glu Cys
            275                 280                 285

Leu Leu Asp Leu Ser Ser Phe Thr Asp Asn Ser Lys Ala Val Asn Lys
            290                 295                 300

Glu Tyr Glu Glu Tyr Val Leu Thr Val Gly Asp Phe Asp Glu Arg Ile
305                 310                 315                 320

Phe Leu Gly Ala Asp Ala Glu Glu Ile Gly Thr Pro Arg Lys Phe
                325                 330                 335

Thr Arg Asp Thr Pro Leu Gly Lys Leu Thr Ala Gln Ala Asn Val Glu
            340                 345                 350

Tyr Asn Leu Gln Gln His Phe Glu Lys Lys Arg Ser Phe Ala Pro Ser
            355                 360                 365

Thr Pro Leu Thr Gly Arg Arg Tyr Leu Arg Glu Lys Glu Ala Val Ile
            370                 375                 380

Thr Pro Val Ala Ser Ala Thr Gln Ser Val Ser Arg Leu Gln Ser Ile
385                 390                 395                 400

Val Ala Gly Leu Lys Asn Ala Pro Ser Asp Gln Leu Ile Asn Ile Phe
                405                 410                 415

Glu Ser Cys Val Arg Asn Pro Val Glu Asn Ile Met Lys Ile Leu Lys
            420                 425                 430

Gly Ile Gly Glu Thr Phe Cys Gln His Tyr Thr Gln Ser Thr Asp Glu
            435                 440                 445

Gln Pro Gly Ser His Ile Asp Phe Ala Val Asn Arg Leu Lys Leu Ala
            450                 455                 460

Glu Ile Leu Tyr Tyr Lys Ile Leu Glu Thr Val Met Val Gln Glu Thr
465                 470                 475                 480

Arg Arg Leu His Gly Met Asp Met Ser Val Leu Leu Glu Gln Asp Ile
                485                 490                 495

Phe His Arg Ser Leu Met Ala Cys Cys Leu Glu Ile Val Leu Phe Ala
            500                 505                 510

Tyr Ser Ser Pro Arg Thr Phe Pro Trp Ile Ile Glu Val Leu Asn Leu
            515                 520                 525

Gln Pro Phe Tyr Phe Tyr Lys Val Ile Glu Val Ile Arg Ser Glu
            530                 535                 540

Glu Gly Leu Ser Arg Asp Met Val Lys His Leu Asn Ser Ile Glu Glu
545                 550                 555                 560

Gln Ile Leu Glu Ser Leu Ala Trp Ser His Asp Ser Ala Leu Trp Glu
                565                 570                 575

Ala Leu Gln Val Ser Ala Asn Lys Val Pro Thr Cys Glu Glu Val Ile
            580                 585                 590

Phe Pro Asn Asn Phe Glu Thr Gly Asn Gly Asn Val Gln Gly His
            595                 600                 605

Leu Pro Leu Met Pro Met Ser Pro Leu Met His Pro Arg Val Lys Glu
            610                 615                 620

Val Arg Thr Asp Ser Gly Ser Leu Arg Arg Asp Met Gln Pro Leu Ser
625                 630                 635                 640

Pro Ile Ser Val His Glu Arg Tyr Ser Ser Pro Thr Ala Gly Ser Ala
                645                 650                 655

Lys Arg Arg Leu Phe Gly Glu Asp Pro Pro Lys Glu Met Leu Met Asp
            660                 665                 670

```
Lys Ile Ile Thr Glu Gly Thr Lys Leu Lys Ile Ala Pro Ser Ser Ser
            675                 680                 685
Ile Thr Ala Glu Asn Val Ser Ile Leu Pro Gly Gln Thr Leu Leu Thr
690                 695                 700
Met Ala Thr Ala Pro Val Thr Gly Thr Thr Gly His Lys Val Thr Ile
705                 710                 715                 720
Pro Leu His Gly Val Ala Asn Asp Ala Gly Glu Ile Thr Leu Ile Pro
                725                 730                 735
Leu Ser Met Asn Thr Asn Gln Glu Ser Lys Val Lys Ser Pro Val Ser
            740                 745                 750
Leu Thr Ala His Ser Leu Ile Gly Ala Ser Pro Lys Gln Thr Asn Leu
            755                 760                 765
Thr Lys Ala Gln Glu Val His Ser Thr Gly Ile Asn Arg Pro Lys Arg
770                 775                 780
Thr Gly Ser Leu Ala Leu Phe Tyr Arg Lys Val Tyr His Leu Ala Ser
785                 790                 795                 800
Val Arg Leu Arg Asp Leu Cys Leu Lys Leu Asp Val Ser Asn Glu Leu
                805                 810                 815
Arg Arg Lys Ile Trp Thr Cys Phe Glu Phe Thr Leu Val His Cys Pro
                820                 825                 830
Asp Leu Met Lys Asp Arg His Leu Asp Gln Leu Leu Leu Cys Ala Phe
            835                 840                 845
Tyr Ile Met Ala Lys Val Thr Lys Glu Glu Arg Thr Phe Gln Glu Ile
            850                 855                 860
Met Lys Ser Tyr Arg Asn Gln Pro Gln Ala Asn Ser His Val Tyr Arg
865                 870                 875                 880
Ser Val Leu Leu Lys Ser Ile Pro Arg Glu Val Val Ala Tyr Asn Lys
                885                 890                 895
Asn Ile Asn Asp Asp Phe Glu Met Ile Asp Cys Asp Leu Glu Asp Ala
                900                 905                 910
Thr Lys Thr Pro Asp Cys Ser Ser Gly Pro Val Lys Glu Glu Arg Gly
            915                 920                 925
Asp Leu Ile Lys Phe Tyr Asn Thr Ile Tyr Val Gly Arg Val Lys Ser
930                 935                 940
Phe Ala Leu Lys Tyr Asp Leu Ala Asn Gln Asp His Met Met Asp Ala
945                 950                 955                 960
Pro Pro Leu Ser Pro Phe Pro His Ile Lys Gln Gln Pro Gly Ser Pro
                965                 970                 975
Arg Arg Ile Ser Gln Gln His Ser Ile Tyr Ile Ser Pro His Lys Asn
            980                 985                 990
Gly Ser Gly Leu Thr Pro Arg Ser Ala Leu Leu Tyr Lys Phe Asn Gly
            995                 1000                1005
Ser Pro Ser Lys Ser Leu Lys Asp Ile Asn Asn Met Ile Arg Gln
    1010                1015                1020
Gly Glu Gln Arg Thr Lys Lys Arg Val Ile Ala Ile Asp Ser Asp
    1025                1030                1035
Ala Glu Ser Pro Ala Lys Arg Val Cys Gln Glu Asn Asp Asp Val
    1040                1045                1050
Leu Leu Lys Arg Leu Gln Asp Val Val Ser Glu Arg Ala Asn His
    1055                1060                1065

<210> SEQ ID NO 14
<211> LENGTH: 19
<212> TYPE: DNA
```

```
<213> ORGANISM: Artificial Sequence
<220> FEATURE:
<223> OTHER INFORMATION: Synthetic p53 shRNA

<400> SEQUENCE: 14
gactccagtg gtaatctac                                          19

<210> SEQ ID NO 15
<211> LENGTH: 21
<212> TYPE: DNA
<213> ORGANISM: Artificial Sequence
<220> FEATURE:
<223> OTHER INFORMATION: Synthetic RB1 shRNA

<400> SEQUENCE: 15
cagagatcgt gtattgagat t                                       21

<210> SEQ ID NO 16
<211> LENGTH: 21
<212> TYPE: DNA
<213> ORGANISM: Artificial Sequence
<220> FEATURE:
<223> OTHER INFORMATION: Synthetic p21 shRNA

<400> SEQUENCE: 16
cgctctacat cttctgcctt a                                       21

<210> SEQ ID NO 17
<211> LENGTH: 18
<212> TYPE: DNA
<213> ORGANISM: Artificial Sequence
<220> FEATURE:
<223> OTHER INFORMATION: Synthetic primer

<400> SEQUENCE: 17
gcctttgctc agtatctt                                           18

<210> SEQ ID NO 18
<211> LENGTH: 18
<212> TYPE: DNA
<213> ORGANISM: Artificial Sequence
<220> FEATURE:
<223> OTHER INFORMATION: Synthetic primer

<400> SEQUENCE: 18
aggtttgggt tgtcatct                                           18

<210> SEQ ID NO 19
<211> LENGTH: 19
<212> TYPE: DNA
<213> ORGANISM: Artificial Sequence
<220> FEATURE:
<223> OTHER INFORMATION: Synthetic primer

<400> SEQUENCE: 19
tatgatgaag cgtttaggc                                          19

<210> SEQ ID NO 20
<211> LENGTH: 20
<212> TYPE: DNA
<213> ORGANISM: Artificial Sequence
<220> FEATURE:
<223> OTHER INFORMATION: Synthetic primer

<400> SEQUENCE: 20
cagtaatgga cagtttgggt                                         20
```

<210> SEQ ID NO 21
<211> LENGTH: 22
<212> TYPE: DNA
<213> ORGANISM: Artificial Sequence
<220> FEATURE:
<223> OTHER INFORMATION: Synthetic primer

<400> SEQUENCE: 21
cagaagtcct acaaggtgtc ca                                            22

<210> SEQ ID NO 22
<211> LENGTH: 21
<212> TYPE: DNA
<213> ORGANISM: Artificial Sequence
<220> FEATURE:
<223> OTHER INFORMATION: Synthetic primer

<400> SEQUENCE: 22
ctctggttga ccgtaactgc g                                             21

<210> SEQ ID NO 23
<211> LENGTH: 22
<212> TYPE: DNA
<213> ORGANISM: Artificial Sequence
<220> FEATURE:
<223> OTHER INFORMATION: Synthetic primer

<400> SEQUENCE: 23
tcgcaaatac tgtggacaat gc                                            22

<210> SEQ ID NO 24
<211> LENGTH: 21
<212> TYPE: DNA
<213> ORGANISM: Artificial Sequence
<220> FEATURE:
<223> OTHER INFORMATION: Synthetic primer

<400> SEQUENCE: 24
gcagtcgtgt gatattggtg t                                             21

<210> SEQ ID NO 25
<211> LENGTH: 19
<212> TYPE: DNA
<213> ORGANISM: Artificial Sequence
<220> FEATURE:
<223> OTHER INFORMATION: Synthetic primer

<400> SEQUENCE: 25
tgggagccat ttgcctctg                                                19

<210> SEQ ID NO 26
<211> LENGTH: 21
<212> TYPE: DNA
<213> ORGANISM: Artificial Sequence
<220> FEATURE:
<223> OTHER INFORMATION: Synthetic primer

<400> SEQUENCE: 26
agccgtggtg gaataggagt a                                             21

<210> SEQ ID NO 27
<211> LENGTH: 23
<212> TYPE: DNA
<213> ORGANISM: Artificial Sequence
<220> FEATURE:

<223> OTHER INFORMATION: Synthetic primer

<400> SEQUENCE: 27
atgaccaagg agtatcaaga cct                                    23

<210> SEQ ID NO 28
<211> LENGTH: 22
<212> TYPE: DNA
<213> ORGANISM: Artificial Sequence
<220> FEATURE:
<223> OTHER INFORMATION: Synthetic primer

<400> SEQUENCE: 28
tgaagttgct gaacgtctct ct                                     22

<210> SEQ ID NO 29
<211> LENGTH: 18
<212> TYPE: DNA
<213> ORGANISM: Artificial Sequence
<220> FEATURE:
<223> OTHER INFORMATION: Synthetic primer

<400> SEQUENCE: 29
agcgtcctct gacactcg                                          18

<210> SEQ ID NO 30
<211> LENGTH: 18
<212> TYPE: DNA
<213> ORGANISM: Artificial Sequence
<220> FEATURE:
<223> OTHER INFORMATION: Synthetic primer

<400> SEQUENCE: 30
ggcatcttgg ctttgact                                          18

<210> SEQ ID NO 31
<211> LENGTH: 18
<212> TYPE: DNA
<213> ORGANISM: Artificial Sequence
<220> FEATURE:
<223> OTHER INFORMATION: Synthetic Primer

<400> SEQUENCE: 31
gcatcctatg tcgcaccc                                          18

<210> SEQ ID NO 32
<211> LENGTH: 18
<212> TYPE: DNA
<213> ORGANISM: Artificial Sequence
<220> FEATURE:
<223> OTHER INFORMATION: Synthetic Primer

<400> SEQUENCE: 32
tcagcaacta accgctcc                                          18

<210> SEQ ID NO 33
<211> LENGTH: 20
<212> TYPE: DNA
<213> ORGANISM: Artificial Sequence
<220> FEATURE:
<223> OTHER INFORMATION: Synthetic Primer

<400> SEQUENCE: 33
tgtctacata gcgggcaagt                                        20

```
<210> SEQ ID NO 34
<211> LENGTH: 18
<212> TYPE: DNA
<213> ORGANISM: Artificial Sequence
<220> FEATURE:
<223> OTHER INFORMATION: Synthetic Primer

<400> SEQUENCE: 34
gttccagcca gcggttct                                                 18

<210> SEQ ID NO 35
<211> LENGTH: 23
<212> TYPE: DNA
<213> ORGANISM: Artificial Sequence
<220> FEATURE:
<223> OTHER INFORMATION: Synthetic Primer

<400> SEQUENCE: 35
ctggcacctc agacaatcca ctc                                           23

<210> SEQ ID NO 36
<211> LENGTH: 23
<212> TYPE: DNA
<213> ORGANISM: Artificial Sequence
<220> FEATURE:
<223> OTHER INFORMATION: Synthetic Primer

<400> SEQUENCE: 36
cagtacggct ttcttgcttc ctc                                           23

<210> SEQ ID NO 37
<211> LENGTH: 20
<212> TYPE: DNA
<213> ORGANISM: Artificial Sequence
<220> FEATURE:
<223> OTHER INFORMATION: Synthetic Primer

<400> SEQUENCE: 37
ggccctcaag gtttccaagg                                               20

<210> SEQ ID NO 38
<211> LENGTH: 21
<212> TYPE: DNA
<213> ORGANISM: Artificial Sequence
<220> FEATURE:
<223> OTHER INFORMATION: Synthetic Primer

<400> SEQUENCE: 38
caccctgtgg tccaacaact c                                             21

<210> SEQ ID NO 39
<211> LENGTH: 21
<212> TYPE: DNA
<213> ORGANISM: Artificial Sequence
<220> FEATURE:
<223> OTHER INFORMATION: Synthetic Primer

<400> SEQUENCE: 39
tcggaagcct aactacagcg a                                             21

<210> SEQ ID NO 40
<211> LENGTH: 20
<212> TYPE: DNA
<213> ORGANISM: Artificial Sequence
<220> FEATURE:
<223> OTHER INFORMATION: Synthetic Primer
```

```
<400> SEQUENCE: 40
agatgagcat tggcagcgag                                               20

<210> SEQ ID NO 41
<211> LENGTH: 25
<212> TYPE: DNA
<213> ORGANISM: Artificial Sequence
<220> FEATURE:
<223> OTHER INFORMATION: Synthetic Primer

<400> SEQUENCE: 41
gctacagcaa gaagtcgagc gaaga                                         25

<210> SEQ ID NO 42
<211> LENGTH: 20
<212> TYPE: DNA
<213> ORGANISM: Artificial Sequence
<220> FEATURE:
<223> OTHER INFORMATION: Synthetic Primer

<400> SEQUENCE: 42
ttgtcagagg gcagcgtggg                                               20

<210> SEQ ID NO 43
<211> LENGTH: 19
<212> TYPE: DNA
<213> ORGANISM: Artificial Sequence
<220> FEATURE:
<223> OTHER INFORMATION: Synthetic Primer

<400> SEQUENCE: 43
cgaggtgccc tatgcctac                                                19

<210> SEQ ID NO 44
<211> LENGTH: 19
<212> TYPE: DNA
<213> ORGANISM: Artificial Sequence
<220> FEATURE:
<223> OTHER INFORMATION: Synthetic Primer

<400> SEQUENCE: 44
ctcggcagag tcaaagtgg                                                19

<210> SEQ ID NO 45
<211> LENGTH: 21
<212> TYPE: DNA
<213> ORGANISM: Artificial Sequence
<220> FEATURE:
<223> OTHER INFORMATION: Synthetic Primer

<400> SEQUENCE: 45
tcctgccaac tttgctctac a                                             21

<210> SEQ ID NO 46
<211> LENGTH: 21
<212> TYPE: DNA
<213> ORGANISM: Artificial Sequence
<220> FEATURE:
<223> OTHER INFORMATION: Synthetic Primer

<400> SEQUENCE: 46
cagggctgga acagttcaca t                                             21

<210> SEQ ID NO 47
<211> LENGTH: 19
```

```
<212> TYPE: DNA
<213> ORGANISM: Artificial Sequence
<220> FEATURE:
<223> OTHER INFORMATION: Synthetic Primer

<400> SEQUENCE: 47
gcgaccaact ccacgtctg                                              19

<210> SEQ ID NO 48
<211> LENGTH: 19
<212> TYPE: DNA
<213> ORGANISM: Artificial Sequence
<220> FEATURE:
<223> OTHER INFORMATION: Synthetic Primer

<400> SEQUENCE: 48
tccccttccc gatacaggc                                              19

<210> SEQ ID NO 49
<211> LENGTH: 18
<212> TYPE: DNA
<213> ORGANISM: Artificial Sequence
<220> FEATURE:
<223> OTHER INFORMATION: Synthetic Primer

<400> SEQUENCE: 49
atgctccgac agcgtctc                                               18

<210> SEQ ID NO 50
<211> LENGTH: 19
<212> TYPE: DNA
<213> ORGANISM: Artificial Sequence
<220> FEATURE:
<223> OTHER INFORMATION: Synthetic Primer

<400> SEQUENCE: 50
tgccctctgc tcctcttac                                              19

<210> SEQ ID NO 51
<211> LENGTH: 20
<212> TYPE: DNA
<213> ORGANISM: Artificial Sequence
<220> FEATURE:
<223> OTHER INFORMATION: Synthetic Primer

<400> SEQUENCE: 51
cttcgctacc tgcctaaccc                                             20

<210> SEQ ID NO 52
<211> LENGTH: 21
<212> TYPE: DNA
<213> ORGANISM: Artificial Sequence
<220> FEATURE:
<223> OTHER INFORMATION: Synthetic Primer

<400> SEQUENCE: 52
gactgtgtca atcctgctc c                                            21

<210> SEQ ID NO 53
<211> LENGTH: 18
<212> TYPE: DNA
<213> ORGANISM: Artificial Sequence
<220> FEATURE:
<223> OTHER INFORMATION: Synthetic Primer

<400> SEQUENCE: 53
```

-continued cagcacttcc tgaatgag                                                        18

<210> SEQ ID NO 54
<211> LENGTH: 23
<212> TYPE: DNA
<213> ORGANISM: Artificial Sequence
<220> FEATURE:
<223> OTHER INFORMATION: Synthetic Primer

<400> SEQUENCE: 54
aggtgactgg gaggacttga ggc                                                  23

<210> SEQ ID NO 55
<211> LENGTH: 21
<212> TYPE: DNA
<213> ORGANISM: Artificial Sequence
<220> FEATURE:
<223> OTHER INFORMATION: Synthetic Primer

<400> SEQUENCE: 55
gcactcctca caggactctt g                                                    21

<210> SEQ ID NO 56
<211> LENGTH: 20
<212> TYPE: DNA
<213> ORGANISM: Artificial Sequence
<220> FEATURE:
<223> OTHER INFORMATION: Synthetic Primer

<400> SEQUENCE: 56
cccaggtgta ccgtgaagac                                                      20

<210> SEQ ID NO 57
<211> LENGTH: 22
<212> TYPE: DNA
<213> ORGANISM: Artificial Sequence
<220> FEATURE:
<223> OTHER INFORMATION: Synthetic Primer

<400> SEQUENCE: 57
ctacagatag gtattaagga ca                                                   22

<210> SEQ ID NO 58
<211> LENGTH: 23
<212> TYPE: DNA
<213> ORGANISM: Artificial Sequence
<220> FEATURE:
<223> OTHER INFORMATION: Synthetic Primer

<400> SEQUENCE: 58
gcttcatatc catgcagcac cac                                                  23

<210> SEQ ID NO 59
<211> LENGTH: 24
<212> TYPE: DNA
<213> ORGANISM: Artificial Sequence
<220> FEATURE:
<223> OTHER INFORMATION: Synthetic Primer

<400> SEQUENCE: 59
tgaaggatga ggccgtctgg gaga                                                 24

<210> SEQ ID NO 60
<211> LENGTH: 24
<212> TYPE: DNA
<213> ORGANISM: Artificial Sequence

```
<220> FEATURE:
<223> OTHER INFORMATION: Synthetic Primer

<400> SEQUENCE: 60
cagtgggcac cgagaagctg aagt                                              24

<210> SEQ ID NO 61
<211> LENGTH: 23
<212> TYPE: DNA
<213> ORGANISM: Artificial Sequence
<220> FEATURE:
<223> OTHER INFORMATION: Synthetic Primer

<400> SEQUENCE: 61
ttcagcaaga agaacaagga caa                                               23

<210> SEQ ID NO 62
<211> LENGTH: 22
<212> TYPE: DNA
<213> ORGANISM: Artificial Sequence
<220> FEATURE:
<223> OTHER INFORMATION: Synthetic Primer

<400> SEQUENCE: 62
ggttgaagaa gtcctcctaa gc                                                22

<210> SEQ ID NO 63
<211> LENGTH: 23
<212> TYPE: DNA
<213> ORGANISM: Artificial Sequence
<220> FEATURE:
<223> OTHER INFORMATION: Synthetic Primer

<400> SEQUENCE: 63
cattactgac ttccgtgcta cat                                               23

<210> SEQ ID NO 64
<211> LENGTH: 22
<212> TYPE: DNA
<213> ORGANISM: Artificial Sequence
<220> FEATURE:
<223> OTHER INFORMATION: Synthetic Primer

<400> SEQUENCE: 64
ctcctgcaca aattcgtttt cc                                                22

<210> SEQ ID NO 65
<211> LENGTH: 21
<212> TYPE: DNA
<213> ORGANISM: Artificial Sequence
<220> FEATURE:
<223> OTHER INFORMATION: Synthetic Primer

<400> SEQUENCE: 65
caaatccttc caagcggcat a                                                 21

<210> SEQ ID NO 66
<211> LENGTH: 22
<212> TYPE: DNA
<213> ORGANISM: Artificial Sequence
<220> FEATURE:
<223> OTHER INFORMATION: Synthetic Primer

<400> SEQUENCE: 66
cgctgagcct aagaactgaa ag                                                22
```

<210> SEQ ID NO 67
<211> LENGTH: 19
<212> TYPE: DNA
<213> ORGANISM: Artificial Sequence
<220> FEATURE:
<223> OTHER INFORMATION: Synthetic Primer

<400> SEQUENCE: 67
gtgctcctgt gcggagtag					19

<210> SEQ ID NO 68
<211> LENGTH: 21
<212> TYPE: DNA
<213> ORGANISM: Artificial Sequence
<220> FEATURE:
<223> OTHER INFORMATION: Synthetic Primer

<400> SEQUENCE: 68
atggcagata ggcagtttcc c					21

<210> SEQ ID NO 69
<211> LENGTH: 19
<212> TYPE: DNA
<213> ORGANISM: Artificial Sequence
<220> FEATURE:
<223> OTHER INFORMATION: Synthetic Primer

<400> SEQUENCE: 69
aagcccagtg tcaacgcag					19

<210> SEQ ID NO 70
<211> LENGTH: 19
<212> TYPE: DNA
<213> ORGANISM: Artificial Sequence
<220> FEATURE:
<223> OTHER INFORMATION: Synthetic Primer

<400> SEQUENCE: 70
gggtcttccg ggtgatctc					19

<210> SEQ ID NO 71
<211> LENGTH: 22
<212> TYPE: DNA
<213> ORGANISM: Artificial Sequence
<220> FEATURE:
<223> OTHER INFORMATION: Synthetic Primer

<400> SEQUENCE: 71
aaccatactc gcaatacagc aa				22

<210> SEQ ID NO 72
<211> LENGTH: 21
<212> TYPE: DNA
<213> ORGANISM: Artificial Sequence
<220> FEATURE:
<223> OTHER INFORMATION: Synthetic Primer

<400> SEQUENCE: 72
acagctcatc ccctttgatc c					21

<210> SEQ ID NO 73
<211> LENGTH: 22
<212> TYPE: DNA
<213> ORGANISM: Artificial Sequence
<220> FEATURE:
<223> OTHER INFORMATION: Synthetic Primer

```
<400> SEQUENCE: 73
atggacacca aacatttcct gc                                            22

<210> SEQ ID NO 74
<211> LENGTH: 21
<212> TYPE: DNA
<213> ORGANISM: Artificial Sequence
<220> FEATURE:
<223> OTHER INFORMATION: Synthetic Primer

<400> SEQUENCE: 74
gggagctgat gaccgagaaa g                                             21

<210> SEQ ID NO 75
<211> LENGTH: 19
<212> TYPE: DNA
<213> ORGANISM: Artificial Sequence
<220> FEATURE:
<223> OTHER INFORMATION: Synthetic Primer

<400> SEQUENCE: 75
gcagcccaaa tgaccctgt                                                19

<210> SEQ ID NO 76
<211> LENGTH: 20
<212> TYPE: DNA
<213> ORGANISM: Artificial Sequence
<220> FEATURE:
<223> OTHER INFORMATION: Synthetic Primer

<400> SEQUENCE: 76
cccgcagcaa tatgacctga                                               20

<210> SEQ ID NO 77
<211> LENGTH: 21
<212> TYPE: DNA
<213> ORGANISM: Artificial Sequence
<220> FEATURE:
<223> OTHER INFORMATION: Synthetic Primer

<400> SEQUENCE: 77
agaggacgat aaggaaggac c                                             21

<210> SEQ ID NO 78
<211> LENGTH: 21
<212> TYPE: DNA
<213> ORGANISM: Artificial Sequence
<220> FEATURE:
<223> OTHER INFORMATION: Synthetic Primer

<400> SEQUENCE: 78
ccatgacaag gcacttctga t                                             21

<210> SEQ ID NO 79
<211> LENGTH: 20
<212> TYPE: DNA
<213> ORGANISM: Artificial Sequence
<220> FEATURE:
<223> OTHER INFORMATION: Synthetic Primer

<400> SEQUENCE: 79
ccccaaggaa tatgcctgcc                                               20

<210> SEQ ID NO 80
```

```
<211> LENGTH: 21
<212> TYPE: DNA
<213> ORGANISM: Artificial Sequence
<220> FEATURE:
<223> OTHER INFORMATION: Synthetic Primer

<400> SEQUENCE: 80
tagggcgaaa gaagaggtcc c                                              21

<210> SEQ ID NO 81
<211> LENGTH: 23
<212> TYPE: DNA
<213> ORGANISM: Artificial Sequence
<220> FEATURE:
<223> OTHER INFORMATION: Synthetic Primer

<400> SEQUENCE: 81
atagctctgt tccagactca act                                            23

<210> SEQ ID NO 82
<211> LENGTH: 21
<212> TYPE: DNA
<213> ORGANISM: Artificial Sequence
<220> FEATURE:
<223> OTHER INFORMATION: Synthetic Primer

<400> SEQUENCE: 82
tcctgaaacc tggtattgcc t                                              21

<210> SEQ ID NO 83
<211> LENGTH: 20
<212> TYPE: DNA
<213> ORGANISM: Artificial Sequence
<220> FEATURE:
<223> OTHER INFORMATION: Synthetic Primer

<400> SEQUENCE: 83
acacctacat gcgtcgcaag                                                20

<210> SEQ ID NO 84
<211> LENGTH: 21
<212> TYPE: DNA
<213> ORGANISM: Artificial Sequence
<220> FEATURE:
<223> OTHER INFORMATION: Synthetic Primer

<400> SEQUENCE: 84
gacgagcttc tcgatcatgc c                                              21

<210> SEQ ID NO 85
<211> LENGTH: 24
<212> TYPE: DNA
<213> ORGANISM: Artificial Sequence
<220> FEATURE:
<223> OTHER INFORMATION: Synthetic Primer

<400> SEQUENCE: 85
atgaagttga attagaaaat gcag                                           24

<210> SEQ ID NO 86
<211> LENGTH: 24
<212> TYPE: DNA
<213> ORGANISM: Artificial Sequence
<220> FEATURE:
<223> OTHER INFORMATION: Synthetic Primer

<400> SEQUENCE: 86
```

```
ggaaactgga ggtatacttt catc                                          24
```

<210> SEQ ID NO 87
<211> LENGTH: 22
<212> TYPE: DNA
<213> ORGANISM: Artificial Sequence
<220> FEATURE:
<223> OTHER INFORMATION: Synthetic Primer

<400> SEQUENCE: 87

```
agcagccata gagctggccc tt                                            22
```

<210> SEQ ID NO 88
<211> LENGTH: 23
<212> TYPE: DNA
<213> ORGANISM: Artificial Sequence
<220> FEATURE:
<223> OTHER INFORMATION: Synthetic Primer

<400> SEQUENCE: 88

```
agcaaaacca ggagccatgt gcc                                           23
```

<210> SEQ ID NO 89
<211> LENGTH: 23
<212> TYPE: DNA
<213> ORGANISM: Artificial Sequence
<220> FEATURE:
<223> OTHER INFORMATION: Synthetic Primer

<400> SEQUENCE: 89

```
gatcaggttt atctccaacc cca                                           23
```

<210> SEQ ID NO 90
<211> LENGTH: 22
<212> TYPE: DNA
<213> ORGANISM: Artificial Sequence
<220> FEATURE:
<223> OTHER INFORMATION: Synthetic Primer

<400> SEQUENCE: 90

```
gatcccagta cgaaacttca cc                                            22
```

<210> SEQ ID NO 91
<211> LENGTH: 22
<212> TYPE: DNA
<213> ORGANISM: Artificial Sequence
<220> FEATURE:
<223> OTHER INFORMATION: Synthetic Primer

<400> SEQUENCE: 91

```
aagaaaggtg atggcgttag ag                                            22
```

<210> SEQ ID NO 92
<211> LENGTH: 23
<212> TYPE: DNA
<213> ORGANISM: Artificial Sequence
<220> FEATURE:
<223> OTHER INFORMATION: Synthetic Primer

<400> SEQUENCE: 92

```
cttgtaactc aacgtcgtag tca                                           23
```

<210> SEQ ID NO 93
<211> LENGTH: 23
<212> TYPE: DNA

```
<213> ORGANISM: Artificial Sequence
<220> FEATURE:
<223> OTHER INFORMATION: Synthetic Primer

<400> SEQUENCE: 93
aaggacaagg tgccctataa agg                                              23

<210> SEQ ID NO 94
<211> LENGTH: 21
<212> TYPE: DNA
<213> ORGANISM: Artificial Sequence
<220> FEATURE:
<223> OTHER INFORMATION: Synthetic Primer

<400> SEQUENCE: 94
acgatcccta tggtgcaagg a                                                21

<210> SEQ ID NO 95
<211> LENGTH: 19
<212> TYPE: DNA
<213> ORGANISM: Artificial Sequence
<220> FEATURE:
<223> OTHER INFORMATION: Synthetic Primer

<400> SEQUENCE: 95
tccttggtta ccctcggca                                                   19

<210> SEQ ID NO 96
<211> LENGTH: 21
<212> TYPE: DNA
<213> ORGANISM: Artificial Sequence
<220> FEATURE:
<223> OTHER INFORMATION: Synthetic Primer

<400> SEQUENCE: 96
agaggcaggt ctctgatggt t                                                21

<210> SEQ ID NO 97
<211> LENGTH: 21
<212> TYPE: DNA
<213> ORGANISM: Artificial Sequence
<220> FEATURE:
<223> OTHER INFORMATION: Synthetic Primer

<400> SEQUENCE: 97
ttggaggtgt tttgactgct t                                                21

<210> SEQ ID NO 98
<211> LENGTH: 23
<212> TYPE: DNA
<213> ORGANISM: Artificial Sequence
<220> FEATURE:
<223> OTHER INFORMATION: Synthetic Primer

<400> SEQUENCE: 98
acaagtggat aaggtcgatg ttg                                              23

<210> SEQ ID NO 99
<211> LENGTH: 23
<212> TYPE: DNA
<213> ORGANISM: Artificial Sequence
<220> FEATURE:
<223> OTHER INFORMATION: Synthetic Primer

<400> SEQUENCE: 99
tatgtggaca ttaaccagat gcc                                              23
```

```
<210> SEQ ID NO 100
<211> LENGTH: 22
<212> TYPE: DNA
<213> ORGANISM: Artificial Sequence
<220> FEATURE:
<223> OTHER INFORMATION: Synthetic Primer

<400> SEQUENCE: 100
ctgtgactgc taagaccttt cg                                              22

<210> SEQ ID NO 101
<211> LENGTH: 20
<212> TYPE: DNA
<213> ORGANISM: Artificial Sequence
<220> FEATURE:
<223> OTHER INFORMATION: Synthetic Primer

<400> SEQUENCE: 101
cagctgattg aggtgtccag                                                 20

<210> SEQ ID NO 102
<211> LENGTH: 20
<212> TYPE: DNA
<213> ORGANISM: Artificial Sequence
<220> FEATURE:
<223> OTHER INFORMATION: Synthetic Primer

<400> SEQUENCE: 102
cactggagga tgtgagtgga                                                 20

<210> SEQ ID NO 103
<211> LENGTH: 20
<212> TYPE: DNA
<213> ORGANISM: Artificial Sequence
<220> FEATURE:
<223> OTHER INFORMATION: Synthetic Primer

<400> SEQUENCE: 103
accaggtctc cactccattg                                                 20

<210> SEQ ID NO 104
<211> LENGTH: 20
<212> TYPE: DNA
<213> ORGANISM: Artificial Sequence
<220> FEATURE:
<223> OTHER INFORMATION: Synthetic Primer

<400> SEQUENCE: 104
atcctgcaag tcgtccatct                                                 20

<210> SEQ ID NO 105
<211> LENGTH: 20
<212> TYPE: DNA
<213> ORGANISM: Artificial Sequence
<220> FEATURE:
<223> OTHER INFORMATION: Synthetic Primer

<400> SEQUENCE: 105
aatatggccc aactgcagaa                                                 20

<210> SEQ ID NO 106
<211> LENGTH: 20
<212> TYPE: DNA
<213> ORGANISM: Artificial Sequence
<220> FEATURE:
```

<223> OTHER INFORMATION: Synthetic Primer

<400> SEQUENCE: 106
catcgcattt tcacatccaa						20

<210> SEQ ID NO 107
<211> LENGTH: 19
<212> TYPE: DNA
<213> ORGANISM: Artificial Sequence
<220> FEATURE:
<223> OTHER INFORMATION: Synthetic Primer

<400> SEQUENCE: 107
cctacggcgt cttctcgac						19

<210> SEQ ID NO 108
<211> LENGTH: 20
<212> TYPE: DNA
<213> ORGANISM: Artificial Sequence
<220> FEATURE:
<223> OTHER INFORMATION: Synthetic Primer

<400> SEQUENCE: 108
ctgcaagaac actctcgcct						20

<210> SEQ ID NO 109
<211> LENGTH: 20
<212> TYPE: DNA
<213> ORGANISM: Artificial Sequence
<220> FEATURE:
<223> OTHER INFORMATION: Synthetic Primer

<400> SEQUENCE: 109
actgaatcca gaacactgca						20

<210> SEQ ID NO 110
<211> LENGTH: 20
<212> TYPE: DNA
<213> ORGANISM: Artificial Sequence
<220> FEATURE:
<223> OTHER INFORMATION: Synthetic Primer

<400> SEQUENCE: 110
tgcagtcaat gcatctttca						20

<210> SEQ ID NO 111
<211> LENGTH: 23
<212> TYPE: DNA
<213> ORGANISM: Artificial Sequence
<220> FEATURE:
<223> OTHER INFORMATION: Synthetic Primer

<400> SEQUENCE: 111
ccaggacaag catggtccca cat					23

<210> SEQ ID NO 112
<211> LENGTH: 25
<212> TYPE: DNA
<213> ORGANISM: Artificial Sequence
<220> FEATURE:
<223> OTHER INFORMATION: Synthetic Primer

<400> SEQUENCE: 112
tccaccgcat ttctccttga cttta					25

<210> SEQ ID NO 113
<211> LENGTH: 18
<212> TYPE: DNA
<213> ORGANISM: Artificial Sequence
<220> FEATURE:
<223> OTHER INFORMATION: Synthetic Primer

<400> SEQUENCE: 113
taacatctgg gtgggtct                                            18

<210> SEQ ID NO 114
<211> LENGTH: 20
<212> TYPE: DNA
<213> ORGANISM: Artificial Sequence
<220> FEATURE:
<223> OTHER INFORMATION: Synthetic Primer

<400> SEQUENCE: 114
cagtggatta gccaataaca                                          20

<210> SEQ ID NO 115
<211> LENGTH: 18
<212> TYPE: DNA
<213> ORGANISM: Artificial Sequence
<220> FEATURE:
<223> OTHER INFORMATION: Synthetic Primer

<400> SEQUENCE: 115
caacccaacc tcatcctc                                            18

<210> SEQ ID NO 116
<211> LENGTH: 18
<212> TYPE: DNA
<213> ORGANISM: Artificial Sequence
<220> FEATURE:
<223> OTHER INFORMATION: Synthetic Primer

<400> SEQUENCE: 116
gtcccatctc acctgctc                                            18

<210> SEQ ID NO 117
<211> LENGTH: 19
<212> TYPE: DNA
<213> ORGANISM: Artificial Sequence
<220> FEATURE:
<223> OTHER INFORMATION: Synthetic Primer

<400> SEQUENCE: 117
gccacctgct gccatccaa                                           19

<210> SEQ ID NO 118
<211> LENGTH: 19
<212> TYPE: DNA
<213> ORGANISM: Artificial Sequence
<220> FEATURE:
<223> OTHER INFORMATION: Synthetic Primer

<400> SEQUENCE: 118
tgcagcccgt agtttaaac                                           19

<210> SEQ ID NO 119
<211> LENGTH: 20
<212> TYPE: DNA
<213> ORGANISM: Artificial Sequence
<220> FEATURE:
<223> OTHER INFORMATION: Synthetic Primer

<400> SEQUENCE: 119
gccctacaac ttcaaccacc                                                    20

<210> SEQ ID NO 120
<211> LENGTH: 19
<212> TYPE: DNA
<213> ORGANISM: Artificial Sequence
<220> FEATURE:
<223> OTHER INFORMATION: Synthetic Primer

<400> SEQUENCE: 120
tgcagcccgt agtttaaac                                                     19

<210> SEQ ID NO 121
<211> LENGTH: 18
<212> TYPE: DNA
<213> ORGANISM: Artificial Sequence
<220> FEATURE:
<223> OTHER INFORMATION: Synthetic Primer

<400> SEQUENCE: 121
ccgtcgccac aatcgtca                                                      18

<210> SEQ ID NO 122
<211> LENGTH: 19
<212> TYPE: DNA
<213> ORGANISM: Artificial Sequence
<220> FEATURE:
<223> OTHER INFORMATION: Synthetic Primer

<400> SEQUENCE: 122
tgcagcccgt agtttaaac                                                     19

<210> SEQ ID NO 123
<211> LENGTH: 17
<212> TYPE: DNA
<213> ORGANISM: Artificial Sequence
<220> FEATURE:
<223> OTHER INFORMATION: Synthetic Primer

<400> SEQUENCE: 123
ccacctttga cgctggg                                                       17

<210> SEQ ID NO 124
<211> LENGTH: 23
<212> TYPE: DNA
<213> ORGANISM: Artificial Sequence
<220> FEATURE:
<223> OTHER INFORMATION: Synthetic Primer

<400> SEQUENCE: 124
cataccagga aatgagcttg aca                                                23

<210> SEQ ID NO 125
<211> LENGTH: 20
<212> TYPE: DNA
<213> ORGANISM: Artificial Sequence
<220> FEATURE:
<223> OTHER INFORMATION: Synthetic Primer

<400> SEQUENCE: 125
aggccttgag tcaatacggg                                                    20

<210> SEQ ID NO 126
<211> LENGTH: 21

<212> TYPE: DNA
<213> ORGANISM: Artificial Sequence
<220> FEATURE:
<223> OTHER INFORMATION: Synthetic Primer

<400> SEQUENCE: 126
tctttggctg aggaggtaga c                                              21

<210> SEQ ID NO 127
<211> LENGTH: 22
<212> TYPE: DNA
<213> ORGANISM: Artificial Sequence
<220> FEATURE:
<223> OTHER INFORMATION: Synthetic Primer

<400> SEQUENCE: 127
cttctcacct tcttggcctt cg                                             22

<210> SEQ ID NO 128
<211> LENGTH: 22
<212> TYPE: DNA
<213> ORGANISM: Artificial Sequence
<220> FEATURE:
<223> OTHER INFORMATION: Synthetic Primer

<400> SEQUENCE: 128
tgcggaaaca gcactcctca ac                                             22

<210> SEQ ID NO 129
<211> LENGTH: 18
<212> TYPE: DNA
<213> ORGANISM: Artificial Sequence
<220> FEATURE:
<223> OTHER INFORMATION: Synthetic Primer

<400> SEQUENCE: 129
agaacgacgg cgtctgca                                                  18

<210> SEQ ID NO 130
<211> LENGTH: 20
<212> TYPE: DNA
<213> ORGANISM: Artificial Sequence
<220> FEATURE:
<223> OTHER INFORMATION: Synthetic Primer

<400> SEQUENCE: 130
gacctgtgaa ctcgggcttg                                                20

<210> SEQ ID NO 131
<211> LENGTH: 18
<212> TYPE: DNA
<213> ORGANISM: Artificial Sequence
<220> FEATURE:
<223> OTHER INFORMATION: Synthetic Primer

<400> SEQUENCE: 131
aggagatggg tgagatgc                                                  18

<210> SEQ ID NO 132
<211> LENGTH: 19
<212> TYPE: DNA
<213> ORGANISM: Artificial Sequence
<220> FEATURE:
<223> OTHER INFORMATION: Synthetic Primer

<400> SEQUENCE: 132

```
gattggtaaa gccagtttc                                                19
```

<210> SEQ ID NO 133
<211> LENGTH: 19
<212> TYPE: DNA
<213> ORGANISM: Artificial Sequence
<220> FEATURE:
<223> OTHER INFORMATION: Synthetic Primer

<400> SEQUENCE: 133

```
tccactttgc catccctaa                                                19
```

<210> SEQ ID NO 134
<211> LENGTH: 20
<212> TYPE: DNA
<213> ORGANISM: Artificial Sequence
<220> FEATURE:
<223> OTHER INFORMATION: Synthetic Primer

<400> SEQUENCE: 134

```
ggtcgtccat actgctgttg                                               20
```

<210> SEQ ID NO 135
<211> LENGTH: 18
<212> TYPE: DNA
<213> ORGANISM: Artificial Sequence
<220> FEATURE:
<223> OTHER INFORMATION: Synthetic Primer

<400> SEQUENCE: 135

```
tgaaactgac tcggaagg                                                 18
```

<210> SEQ ID NO 136
<211> LENGTH: 18
<212> TYPE: DNA
<213> ORGANISM: Artificial Sequence
<220> FEATURE:
<223> OTHER INFORMATION: Synthetic Primer

<400> SEQUENCE: 136

```
cagaatgaga tggtggtg                                                 18
```

<210> SEQ ID NO 137
<211> LENGTH: 20
<212> TYPE: DNA
<213> ORGANISM: Artificial Sequence
<220> FEATURE:
<223> OTHER INFORMATION: Synthetic Primer

<400> SEQUENCE: 137

```
taaccctgct cggtcctttg                                               20
```

<210> SEQ ID NO 138
<211> LENGTH: 20
<212> TYPE: DNA
<213> ORGANISM: Artificial Sequence
<220> FEATURE:
<223> OTHER INFORMATION: Synthetic Primer

<400> SEQUENCE: 138

```
ccaccctgga gttgatgtcg                                               20
```

<210> SEQ ID NO 139
<211> LENGTH: 20
<212> TYPE: DNA
<213> ORGANISM: Artificial Sequence

```
<220> FEATURE:
<223> OTHER INFORMATION: Synthetic Primer

<400> SEQUENCE: 139
cgtagaggct ttccggtttg                                                    20

<210> SEQ ID NO 140
<211> LENGTH: 22
<212> TYPE: DNA
<213> ORGANISM: Artificial Sequence
<220> FEATURE:
<223> OTHER INFORMATION: Synthetic Primer

<400> SEQUENCE: 140
tagtaggaga tcgggtgagt gg                                                 22

<210> SEQ ID NO 141
<211> LENGTH: 19
<212> TYPE: DNA
<213> ORGANISM: Artificial Sequence
<220> FEATURE:
<223> OTHER INFORMATION: Synthetic Primer

<400> SEQUENCE: 141
cgctggcggt actgaagtc                                                     19

<210> SEQ ID NO 142
<211> LENGTH: 21
<212> TYPE: DNA
<213> ORGANISM: Artificial Sequence
<220> FEATURE:
<223> OTHER INFORMATION: Synthetic Primer

<400> SEQUENCE: 142
gaggaacggt gacatgctca t                                                  21

<210> SEQ ID NO 143
<211> LENGTH: 23
<212> TYPE: DNA
<213> ORGANISM: Artificial Sequence
<220> FEATURE:
<223> OTHER INFORMATION: Synthetic Primer

<400> SEQUENCE: 143
aataaggcga agatcaacat ggc                                                23

<210> SEQ ID NO 144
<211> LENGTH: 23
<212> TYPE: DNA
<213> ORGANISM: Artificial Sequence
<220> FEATURE:
<223> OTHER INFORMATION: Synthetic Primer

<400> SEQUENCE: 144
tttgttacca atgtccccaa gag                                                23

<210> SEQ ID NO 145
<211> LENGTH: 21
<212> TYPE: DNA
<213> ORGANISM: Artificial Sequence
<220> FEATURE:
<223> OTHER INFORMATION: Synthetic Primer

<400> SEQUENCE: 145
tgctctgcaa aatcgaggac a                                                  21
```

<210> SEQ ID NO 146
<211> LENGTH: 20
<212> TYPE: DNA
<213> ORGANISM: Artificial Sequence
<220> FEATURE:
<223> OTHER INFORMATION: Synthetic Primer

<400> SEQUENCE: 146
gccaatccac taggatggca                                                   20

<210> SEQ ID NO 147
<211> LENGTH: 20
<212> TYPE: DNA
<213> ORGANISM: Artificial Sequence
<220> FEATURE:
<223> OTHER INFORMATION: Synthetic Primer

<400> SEQUENCE: 147
tccgaaccaa gtttgagacg                                                   20

<210> SEQ ID NO 148
<211> LENGTH: 21
<212> TYPE: DNA
<213> ORGANISM: Artificial Sequence
<220> FEATURE:
<223> OTHER INFORMATION: Synthetic Primer

<400> SEQUENCE: 148
ccctcagcgt actgatttcc t                                                 21

<210> SEQ ID NO 149
<211> LENGTH: 18
<212> TYPE: DNA
<213> ORGANISM: Artificial Sequence
<220> FEATURE:
<223> OTHER INFORMATION: Synthetic Primer

<400> SEQUENCE: 149
tccaacgacc agaccatc                                                     18

<210> SEQ ID NO 150
<211> LENGTH: 18
<212> TYPE: DNA
<213> ORGANISM: Artificial Sequence
<220> FEATURE:
<223> OTHER INFORMATION: Synthetic Primer

<400> SEQUENCE: 150
agtctcctcc atttagcg                                                     18

<210> SEQ ID NO 151
<211> LENGTH: 20
<212> TYPE: DNA
<213> ORGANISM: Artificial Sequence
<220> FEATURE:
<223> OTHER INFORMATION: Synthetic Primer

<400> SEQUENCE: 151
caacgtgagc ggtagcttca                                                   20

<210> SEQ ID NO 152
<211> LENGTH: 19
<212> TYPE: DNA
<213> ORGANISM: Artificial Sequence
<220> FEATURE:
<223> OTHER INFORMATION: Synthetic Primer

```
<400> SEQUENCE: 152
gcatcttgtc ggtgggcat                                              19

<210> SEQ ID NO 153
<211> LENGTH: 23
<212> TYPE: DNA
<213> ORGANISM: Artificial Sequence
<220> FEATURE:
<223> OTHER INFORMATION: Synthetic Primer

<400> SEQUENCE: 153
gaggctaaag aactttggga tca                                         23

<210> SEQ ID NO 154
<211> LENGTH: 19
<212> TYPE: DNA
<213> ORGANISM: Artificial Sequence
<220> FEATURE:
<223> OTHER INFORMATION: Synthetic Primer

<400> SEQUENCE: 154
catttcgggg tcggcctta                                              19

<210> SEQ ID NO 155
<211> LENGTH: 18
<212> TYPE: DNA
<213> ORGANISM: Artificial Sequence
<220> FEATURE:
<223> OTHER INFORMATION: Synthetic Primer

<400> SEQUENCE: 155
atttcctcgg tggtgtcc                                               18

<210> SEQ ID NO 156
<211> LENGTH: 21
<212> TYPE: DNA
<213> ORGANISM: Artificial Sequence
<220> FEATURE:
<223> OTHER INFORMATION: Synthetic Primer

<400> SEQUENCE: 156
ccaaactgtt caagtggcag a                                           21

<210> SEQ ID NO 157
<211> LENGTH: 24
<212> TYPE: DNA
<213> ORGANISM: Artificial Sequence
<220> FEATURE:
<223> OTHER INFORMATION: Synthetic Primer

<400> SEQUENCE: 157
gactacaccg accaccagaa ctcc                                        24

<210> SEQ ID NO 158
<211> LENGTH: 19
<212> TYPE: DNA
<213> ORGANISM: Artificial Sequence
<220> FEATURE:
<223> OTHER INFORMATION: Synthetic Primer

<400> SEQUENCE: 158
gtctgcggga tggaaggga                                              19

<210> SEQ ID NO 159
```

```
<211> LENGTH: 20
<212> TYPE: DNA
<213> ORGANISM: Artificial Sequence
<220> FEATURE:
<223> OTHER INFORMATION: Synthetic Primer

<400> SEQUENCE: 159
ttgtgaggct taggaatgaa                                               20

<210> SEQ ID NO 160
<211> LENGTH: 20
<212> TYPE: DNA
<213> ORGANISM: Artificial Sequence
<220> FEATURE:
<223> OTHER INFORMATION: Synthetic Primer

<400> SEQUENCE: 160
aaggacctga gtggtaggaa                                               20

<210> SEQ ID NO 161
<211> LENGTH: 20
<212> TYPE: DNA
<213> ORGANISM: Artificial Sequence
<220> FEATURE:
<223> OTHER INFORMATION: Synthetic Primer

<400> SEQUENCE: 161
ttgaggccag gagtttgaga                                               20

<210> SEQ ID NO 162
<211> LENGTH: 21
<212> TYPE: DNA
<213> ORGANISM: Artificial Sequence
<220> FEATURE:
<223> OTHER INFORMATION: Synthetic Primer

<400> SEQUENCE: 162
ggcattacag gcatgtgcta c                                             21
```

HUMAN HEPATOCYTE-LIKE CELLS AND USES THEREOF

CROSS REFERENCE TO RELATED APPLICATION

This application is a 371 International Application PCT/CN2014/071898 filed 8 Feb. which was published on 14 Aug. 2014 with International Publication Number WO 2014/121758.This application claims priority of Chinese Application No. 201310050796.7filed on Feb. 8,2013. The content of the application is incorporated by reference in its entirety.

FIELD OF THE INVENTION

This invention relates to hepatocyte-like cells, related compositions, and related methods that are useful for improving liver function and treating various liver disorders.

BACKGROUND OF THE INVENTION

The liver is a pivotal organ in regulating many physiological processes, such as glycogen storage, lipid metabolism, plasma protein secretion, and xenobiotic detoxification. Liver diseases, such as liver metabolic diseases and fulminant liver failure, are responsible for a huge number of deaths worldwide. Liver transplantation is currently the only curative treatment for these diseases at the end stages. In addition, primary human hepatocyte (PHH) transplantation has been recently evaluated in clinics as an alternative to organ transplantation. On the other hand, liver support devices containing functional hepatocytes have been developed in order to allow the liver to recover from acute liver failure (Carpentier et al., 2009, Gut 58, 1690-1702.). Besides the therapeutic applications, hepatocytes are widely used for disease modeling, such as hepatitis C virus infection and humanized animal models, and for drug metabolism and pharmacokinetics analysis, e.g. hepatobiliary disposition of drug candidates (Azuma, et al., 2007, Nat Biotechnol 25, 903-910; Gomez-Lechon et al., 2004, Current drug metabolism 5, 443-462; and Lazaro, et al. 2007, Am J Pathol 170, 478-489). However, the demand for liver organs and functional hepatocytes far exceeds the supply of cadaveric livers and liver tissues from living donors. Generation of surrogate hepatocytes can be used to meet these demands. Thus, there is a need for human hepatocytes or hepatocyte-like cells.

Overexpression of lineage-specific transcription factors has been used to change cell fates. Direct cell lineage conversion through reprogramming facilitates the generation of donor organ-independent cells for applications in regenerative medicine or personalized disease modeling. Whereas several studies have successfully converted mouse fibroblasts into other cell types, it is well accepted that human cells are resistant to lineage reprogramming (Nam et al. 2013, Proc Natl Acad Sci USA 110, 5588-5593; Pang et al. 2011, Nature 476, 220-223; and Qiang et al., 2011, Cell 146, 359-371). For example, trans-differentiation into neuronal cells (iN) has been demonstrated in human cells; however, the in vivo functions of human iN, especially their application in therapeutic treatment, have not yet been thoroughly characterized. A recent study managed to reprogram human fibroblasts into cells with a cardiac fate, but these cells lacked mature cardiac functions (Nam et al. 2013, Proc Natl Acad Sci USA 110, 5588-5593). Furthermore, trans-differentiated cells are proliferation arrested, which precludes them from expanding in large numbers for in vivo measurements and biomedical applications.

SUMMARY OF INVENTION

This invention relates to a novel method for generating human hepatocyte-like cells, related cells, and related methods.

In one aspect, the invention provides a method of generating human hepatocyte-like cells. The method includes forcing expression (e.g., via nucleic acid transfection, virus infection, and protein transduction) of a FOXA polypeptide and a HNF polypeptide in a non-hepatic human cell or its progeny cell, and culturing the cell in a medium for a period of time (e.g., about 1-20 days, 2-14 days or 10-14 days) to obtain one or more progeny cells thereof, thereby generating human hepatocyte-like cells. The HNF polypeptide can be HNF4A, HNF1A, or HNF1B; the FOXA polypeptide can be FOXA1, FOXA2, or FOXA3.

In some embodiments, the FOXA polypeptide can be FOXA3 and the HNF polypeptide can be HNF4A or HNF1A. In that case, the method includes forcing expression of (i) the FOXA3 polypeptide and the HNF1A polypeptide or (ii) the FOXA3 polypeptide and the HNF4A polypeptide in the non-hepatic human cell.

In other embodiments, the method includes forcing expression of the FOXA3polypeptide, the HNF4A polypeptide, and one or both of the HNF1A polypeptide and HNF1B polypeptide in the non-hepatic human cell.

The non-hepatic human cell can be any suitable somatic cell. Examples of such a cell include a fibroblast, an epithelium cell, a blood cell, a neuron, an embryonic cell, or a cell derived from a non-hepatic tissue or organ of a subject.

In preferred embodiments, the method further includes increasing cell proliferation, or decreasing apoptosis or cell senescence, of the non-hepatic human cell or one or more of the progeny cells. The increasing step can be carried out by forcing expression of a SV40 large T antigen in the non-hepatic human cell or one or more of the progeny cells. The decreasing step can be carried out by reducing expression or activity of an Rb family gene in the non-hepatic human cell or one or more of the progeny cells. Preferably, forcing expression of the SV40 large T antigen or reducing expression/activity of an Rb family gene is carried out in a controllable manner. In some other embodiments, the method can further include forcing expression of one or more additional polypeptides selected from the group consisting of C/EBPβ, GATA4, HHEX, KLF4, and PROX1 in the non-hepatic human cell or its progeny.

In a second aspect, the invention provides a cultured recombinant cell. The cell contains (i) a first agent selected from a first group consisting of a heterologous HNF polypeptide and a first heterologous nucleic acid encoding said HNF polypeptide; and (ii) a second agent selected from a second group consisting of a heterologous FOXA polypeptide and a second heterologous nucleic acid encoding the FOXA polypeptide. The HNF polypeptide can be HNF4A, HNF1A, or HNF1B. The FOXA polypeptide can be FOXA1, FOXA2, or FOXA3. The cell can further contain an additional agent selected from a group consisting of an additional heterologous polypeptide and an additional heterologous nucleic acid encoding the additional polypeptide. The additional heterologous polypeptide can be one selected from the group consisting of C/EBPβ, GATA4, HHEX, KLF4, and PROX1. In some embodiments, the cell further contains a heterologous SV40 large T antigen or a heterologous nucleic acid encoding the SV40 large T antigen. In others, the cell is RB null or expresses an Rb family gene at a level lower than a predetermined level. In yet other embodiments, the cell can contain an agent (e.g., an siRNA or related dsRNA) that inhibits expression or activity of the Rb family gene.

In a third aspect, the invention provides a cultured hepatocyte-like cell obtained using the method described above. The cell is positive for one or more hepatic functional genes, and/or displays one or more mature hepatic functions as disclosed herein. For example, the cell can display biliary excretion or is capable of metabolizing one or more compounds selected from the group consisting of 3-methylcholanthrene, phenobarbital, rifampicin, phenacetin, coumarin, dextromethorphan, testosterone, and diclofenac. The cell in general can have a normal karyotype and/or does not form tumor after transplantation in an immuno-deficient mouse.

The above-described cell can be used to make a pharmaceutical composition. Accordingly, the invention provides a pharmaceutical composition containing the cell and a pharmaceutically acceptable carrier. For the pharmaceutical composition, the cell can be encapsulated in a microcapsule, e.g., a microcapsule containing alginate-poly-L-lysine-alginate (APA).

The invention also provides a bioartificial liver device containing the above-described cell or pharmaceutical composition. The device can be either an extracorporeal device or an implantable/implanted device. The bioartificial device includes a bioreactor embedded with the cells described above and can perform certain functions of a normal liver. For example, the device can perform a metabolic function, including lipid and plasma lipoprotein synthesis, regulation of carbohydrate homeostasis, production of serum albumin and clotting factors, and/or detoxification. It can be used to support people who have liver failure. In one embodiment, the device can include a reservoir chamber configured to house hepatocytes or hepatocyte-like cells, a plurality of the cells or composition described above in the reservoir chamber, an inlet in fluid with said chamber and cells, and an outlet in fluid communication with said chamber and cells.

In another aspect, the invention provides a method for improving the liver function of a subject in need thereof. The method includes administering to the subject the cell or the pharmaceutical composition described above. Alternatively, it includes connecting to the subject or implanting in the subject the above-described extracorporeal or implantable/implanted device. The subject can be a patient having a metabolic liver disease or liver failure. In preferred embodiments, the cell is autologous to the subject, i.e., prepared from a non-hepatic cell of the subject.

In yet another aspect, the invention provides a method of evaluating toxicity, carcinogenicity, or biotransformation activity of a test substance. The method includes contacting a test substance with the above-described cell, and examining a level of metabolic activity or viability of the cell. The level indicates the toxicity, carcinogenicity, or biotransformation activity of the test substance.

In a further aspect, the invention provides a composition containing a first agent selected from a first group consisting of a HNF polypeptide and a first nucleic acid encoding said HNF polypeptide; and a second agent selected from a second group consisting of FOXA polypeptide and a second nucleic acid encoding said FOXA polypeptide. The HNF polypeptide can be HNF4A, HNF1A, or HNF1B. The FOXA polypeptide can be FOXA1, FOXA2, or FOXA3. The composition can further include an additional agent selected from a group consisting of an additional polypeptide, an additional nucleic acid encoding the additional polypeptide, and a compound (e.g., siRNA or related dsRNA) that reduces the expression of an Rb family gene. The additional polypeptide can be selected from the group consisting of SV40 large T antigen, C/EBPβ, GATA4, HHEX, KLF4, and PROX1. Also provided is a kit containing the composition.

In a further aspect, the invention provides use of the above described cells, compositions, or device for improving the liver function of a subject, including uses of the cells or compositions in the manufacture of a medicament.

The details of one or more embodiments of the invention are set forth in the description below. Other features, objectives, and advantages of the invention will be apparent from the description and from the claims.

DETAILED DESCRIPTION OF THE INVENTION

Figure 1:
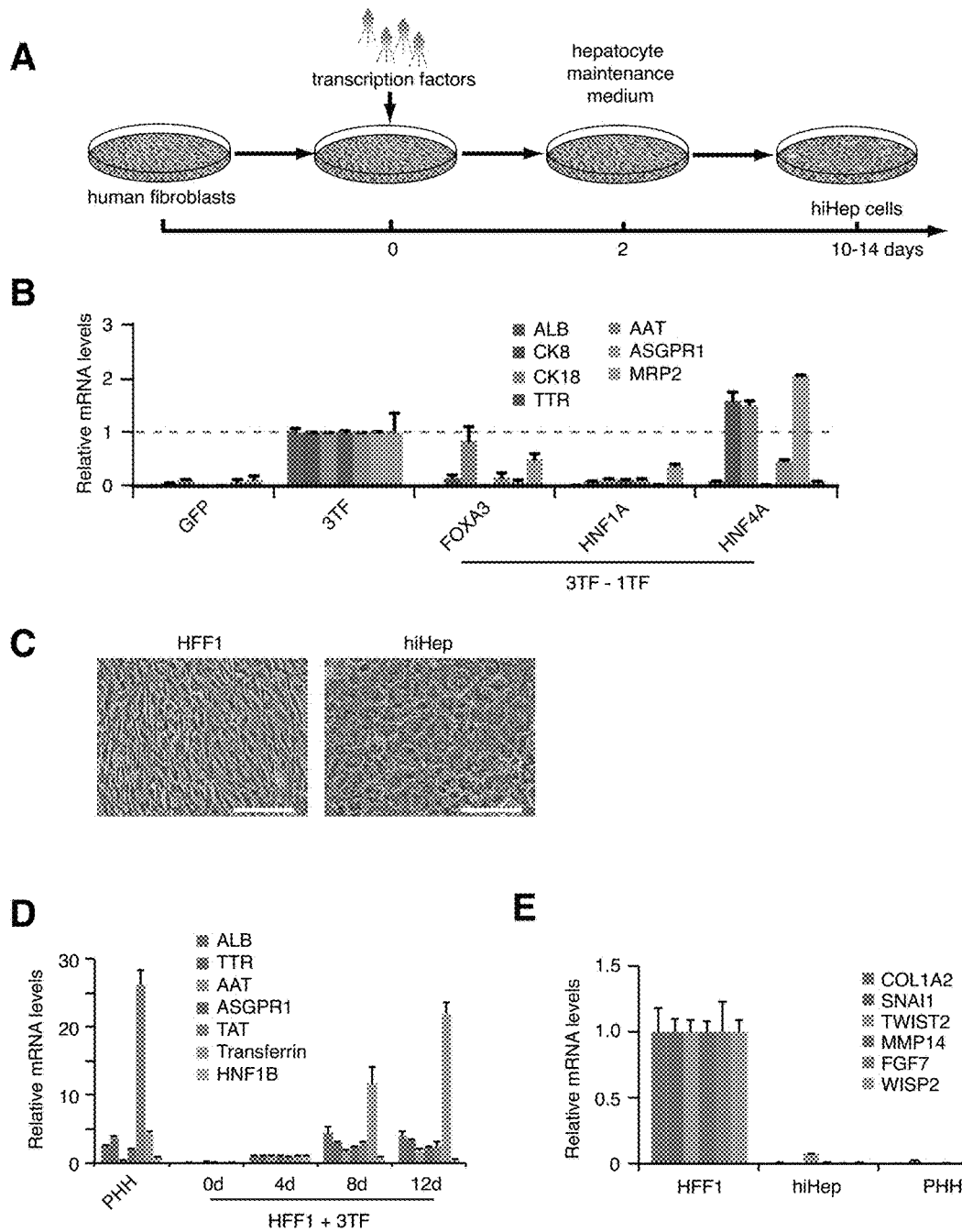
FIGS. 1A-1E are a set of diagrams and photographs showing induction of hepatocyte-like cells from human foetal fibroblasts: (A) experimental design for the induction of human hepatocyte-like (hiHep) cells; (B) FOXA3, HNF1A and HNF4A induced hepatic gene expression in human foetal limb fibroblasts (HFF1); (C) hiHep cells showed typical epithelial morphology; (D) gradually increased hepatic gene expression during the induction of hiHep cells; (E) genes specific to the original fibroblasts were silenced in hiHep cells at 2 weeks after induction. Scale bars: 100 µm. Data are represented as the mean±SD.

This invention is based, at least in part, on unexpected discoveries that non-liver human cells (e.g., adult fibroblast cells) can be converted to hepatocyte-like cells via forced expression of as few as 2 or 3 heterologous transcription factors.

It has been demonstrated that mouse fibroblasts could be directly converted to hepatic lineage by defined transcription factors (Huang et al., 2011, Nature 475, 386-389; and Sekiya et al., 2011, Nature 475, 390-393). However, the extension of these findings to human cells is a challenge that must be overcome for biomedical and pharmaceutical applications (Cherry et al., 2012, Cell 148, 1110-1122; Tiscornia et al., 2011, Nat Med 17, 1570-1576; and Vierbuchen et al., 2011, Nat Biotechnol 29, 892-907).

As disclosed herein, human induced hepatocyte-like (hiHep) cells can be efficiently generated from non-hepatic human cells, such as human foetal fibroblasts (HFF), adult fibroblasts (HAF) and adult adipose tissue-derived mesenchymal stem cells (AD-MSC) by forced expression of FOXA3, HNF1A and HNF4A, which differ from factors used for mouse cells. As disclosed herein, hiHep cells show mature hepatic functions, specifically, cytochrome P450 (CYP) enzyme activities and biliary excretion of drug compounds. Notably, the therapeutic effects of hiHep cells were demonstrated on fumarylacetoacetate hydrolase (Fah) deficiency-induced metabolic liver disease and concanavalin A (Con A)-induced acute liver failure, which is the first therapeutic characterization of trans-differentiated human cells in vivo. These results indicate that hiHep cells could be applied in cellular therapies, disease modeling and drug discovery.

An iHep cell refers to a cell displaying one or more properties that are characteristic of mature, parenchymal hepatocytes as disclosed below. Preferably, an iHep cell may display at least one, two, three, four, five or more of the following properties: ability to use pyruvate as a sole carbon source; phase I biotransformation capacity (e.g., ethoxyresorufin, pentoxyresorufin, testosterone); phase II biotransformation capacity (e.g., 1-chloro-2,4 dinitrobenzene, 1,2-dichloro-4-nitrobenzene, 7-chloro-4-nitrobenzene-2-oxa-1, 3-diazole, estradiol, estrogen), the presence of cytochrome P450 protein and gene expression; inducibility of phase I and phase II biotransformation enzymes (e.g., beta-naphthoflavone, phenobarbital, methylcholanthrene); albumin secretion, urea production, glycogen storage, the presence of the expression of one or more of endogenous ALB, AFP, gamma-glutyryltransferase, hepatocyte nuclear factor (HNF) 1α, HNF 1β, HNF 3α, HNF 3β, HNF 5, HNF-6, anti-trypsin, CX32, MRP2, C/EBPα, transthyretin, CK-18 and/or CFTR; polygonal morphology. In one specific embodiment, iHep cells of this invention showed an expression profile and hepatic function close to those of mature hepatocytes where some CYP genes were not induced, and CK19 and Afp were up-regulated. The iHep cells are not identical to hepatocytes. The iHep cells of this invention are genetically stable and not prone to tumor formation. They can be used for disease modeling, transplantation, and tissue engineering.

As mentioned above, there is an unmet need for human hepatocytes or hepatocyte-like cells. Differentiating human embryonic stem cells (hESCs) into hepatocytes or the like has been recently developed. Although these hESCs derived cells show typical morphology and phenotypes of human hepatocytes, their uses as patient-compatible hepatocytes or the like are limited by the number of hESC lines available. The success in generating induced pluripotent stem cell (iPSC) makes it possible to produce hepatocytes from a patient's own cells, when iPSCs are differentiated to hepatic endoderm. Yet, cells derived from either hESC or iPSC pose the concern for contamination of undifferentiated pluripotent stem cells that could form teratoma in vivo. Multipotential mesenchymal stem cells (MSCs), which show in vitro proliferation and multiple lineage differentiations, can be differentiated in vitro into hepatocyte-like cells with appropriate hepatic gene expression and functional attributes. However, the application of MSC-derived hepatocyte-like cells is limited by the low efficiency and a mixture of differentiated cells derived.

As disclosed herein, conversion of non-hepatic human cells, such as foetal fibroblasts, adult fibroblasts, and adipose tissue-derived mesenchymal stem cells to induce exogenous hepatocyte-like (iHep) cells were established by over-expression of transcription factors such as FOXA3, HNF1A and HNF4A and forced expression of SV 40 large T antigen or inactivation of one or more RB family genes. It was found that epithelial colony from fibroblasts was induced after forced expression of transduction of transcription factors, and iHep cells were obtained and readily expandable. iHep cells appeared to be epigenetically stable since exogenous transcription factors were silenced after lineage conversion. Remarkably, iHep cells with an expression profile close to mature hepatocytes showed multiple hepatic functions in vitro, such as glycogen storage, albumin secretion, low-density-lipoprotein transportation and metabolism of xenobiotics. By rigorous analysis of lineage markers, fibroblasts were only converted to mature hepatic cells, but not to hepatic progenitor cells or other cell lineages.

Transcription Factors and Other Factors Useful for the Invention

Various transcription factors can be used in this invention to generate iHep cells. Examples of them include those of the hepatocyte nuclear factor (HNF) 1 or 4 subfamily (e.g., HNF1A, HNF1B, and HNF4A) and the forkhead box A protein (FOXA) family (e.g., FOXA1, FOXA2, and FOXA3). These transcription factors and other exemplary factors are listed in Table 1 below. Also listed in the table are examples of other factors, the forced expression or reduction of which is for expanding iHep cells, including SV 40 large T antigen and RB family genes. Homologs from other species (e.g., other mammals) can also be used. See e.g., WO2012058868, the content of which is incorporated by reference.

TABLE 1

Human Transcription Factors And Other Factors
For Hepatic Conversion Of Human Fibroblasts

| Gene Name | Genbank Number | SEQ ID NO for corresponding polypeptides |
| --- | --- | --- |
| FOXA3 | NM_004497 | 1 |
| HNF1B | NM_000458 | 2 |
| GATA4 | NM_002052 | 3 |
| HNF4A | NM_000457 | 4 |
| C/EBPβ | NM_005194 | 5 |
| HHEX | NM_002729 | 6 |
| PROX1 | NM_002763 | 7 |
| KLF4 | NM_004235 | 8 |
| HNF1A | NM_000545 | 9 |
| SV40 large T | YP_003708382 | 10 |
| RB family gene p130 | NM_005611 | 11 |
| RB family gene RB1 | NM_000321 | 12 |
| RB family gene p107 | N_002895 | 13 |

FOXA3 (SEQ ID NO: 1)
MLGSVKMEAHDLAEWSYYPEAGEVYSPVTPVPTMAPLNSYMTLNPLSSPY
PPGGLPASPLPSGPLAPPAPAAPLGPTFPGLGVSGGSSSSGYGAPGPGLV
HGKEMPKGYRRPLAHAKPPYSYISLITMAIQQAPGKMLTLSEIYQWIMDL
FPYYRENQQRWQNSIRHSLSFNDCFVKVARSPDKPGKGSYWALHPSSGNM
FENGCYLRRQKRFKLEEKVKKGGSGAATTTRNGTGSAASTTTPAATVTSP

TABLE 1-continued

Human Transcription Factors And Other Factors
For Hepatic Conversion Of Human Fibroblasts PQPPPPAPEPEAQGGEDVGALDCGSPASSTPYFTGLELPGELKLDAPYNF
NHPFSINNLMSEQTPAPPKLDVGFGGYGAEGGEPGVYYQGLYSRSLLNAS HNF1B (SEQ ID NO: 2)
MVSKLTSLQQELLSALLSSGVTKEVLVQALEELLPSPNFGVKLETLPLSP
GSGAEPDTKPVFHTLTNGHAKGRLSGDEGSEDGDDYDTPPILKELQALNT
EEAAEQRAEVDRMLSEDPWRAAKMIKGYMQQHNIPQREVVDVTGLNQSHL
SQHLNKGTPMKTQKRAALYTWYVRKQREILRQFNQTVQSSGNMTDKSSQD
QLLFLFPEFSQQSHGPGQSDDACSEPTNKKMRRNRFKWGPASQQILYQAY
DRQKNPSKEEREALVEECNRAECLQRGVSPSKAHGLGSNLVTEVRVYNWF
ANRRKEEAFRQKLAMDAYSSNQTHSLNPLLSHGSPHHQPSSSPPNKLSGV
RYSQQGNNEITSSSTISHHGNSAMVTSQSVLQQVSPASLDPGHNLLSPDG
KMISVSGGGLPPVSTLTNIHSLSHHNPQQSQNLIMTPLSGVMAIAQSLNT
SQAQSVPVINSVAGSLAALQPVQFSQQLHSPHQQPLMQQSPGSHMAQQPF
MAAVTQLQNSHMYAHKQEPPQYSHTSRFPSAMVVTDTSSISTLTNMSSSK
QCPLQAW GATA4 (SEQ ID NO: 3)
MYQSLAMAANHGPPPGAYEAGGPGAFMHGAGAASSPVYVPTPRVPSSVLG
LSYLQGGGAGSASGGASGGSSGGAASGAGPGTQQGSPGWSQAGADGAAYT
PPPVSPRFSFPGTTGSLAAAAAAAAREAAAYSSGGGAAGAGLAGREQYG
RAGFAGSYSSPYPAYMADVGASWAAAAAASAGPFDSPVLHSLPGRANPAA
RHPNLDMFDDFSEGRECVNCGAMSTPLWRRDGTGHYLCNACGLYHKMNGI
NRPLIKPQRRLSASRRVGLSCANCQTTTTTLWRRNAEGEPVCNACGLYMK
LHGVPRPLAMRKEGIQTRKRKPKNLNKSKTPAAPSGSESLPPASGASSNS
SNATTSSSEEMRPIKTEPGLSSHYGHSSSVSQTFSVSAMSGHGPSIHPVL
SALKLSPQGYASPVSQSPQTSSKQDSWNSLVLADSHGDIITA HNF4A (SEQ ID NO: 4)
MRLSKTLVDMDMADYSAALDPAYTTLEFENVQVLTMGNDTSPSEGTNLNA
PNSLGVSALCAICGDRATGKHYGASSCDGCKGFFRRSVRKNHMYSCRFSR
QCVVDKDKRNQCRYCRLKKCFRAGMKKEAVQNERDRISTRRSSYEDSSLP
SINALLQAEVLSRQITSPVSGINGDIRAKKIASIADVCESMKEQLLVLVE
WAKYIPAFCELPLDDQVALLRAHAGEHLLLGATKRSMVFKDVLLLGNDYI
VPRHCPELAEMSRVSIRILDELVLPFQELQIDDNEYAYLKAIIFFDPDAK
GLSDPGKIKRLRSQVQVSLEDYINDRQYDSRGRFGELLLLLPTLQSITWQ
MIEQIQFIKLFGMAKIDNLLQEMLLGGSPSDAPHAHHPLHPHLMQEHMGT
NVIVANTMPTHLSNGQMCEWPRPRGQAATPETPQPSPPGGSGSEPYKLLP
GAVATIVKPLSAIPQPTITKQEVI C/EBPβ (SEQ ID NO: 5)
MQRLVAWDPACLPLPPPPPAFKSMEVANFYYEADCLAAAYGGKAAPAAPP
AARPGPRPPAGELGSIGDHERAIDFSPYLEPLGAPQAPAPATATDTFEAA
PPAPAPAPASSGQHHDFLSDLFSDDYGGKNCKKPAEYGYVSLGRLGAAKG
ALHPGCFAPLHPPPPPPPPPAELKAEPGFEPADCKRKEEAGAPGGGAGMA
AGFPYALRAYLGYQAVPSGSSGSLSTSSSSSPPGTPSPADAKAPPTACYA
GAAPAPSQVKSKAKKTVDKHSDEYKIRRERNNIAVRKSRDKAKMRNLETQ
HKVLELTAENERLQKKVEQLSRELSTLRNLFKQLPEPLLASSGHC HHEX (SEQ ID NO: 6)
MQYPHPGPAAGAVGVPLYAPTPLLQPAHPTPFYIEDILGRGPAAPTPAPT
LPSPNSSFTSLVSPYRTPVYEPTPIHPAFSHHSAAALAAAYGPGGFGGPL
YPFPRTVNDYTHALLRHDPLGKPLLWSPFLQRPLHKRKGGQVRFSNDQTI
ELEKKFETQKYLSPPERKRLAKMLQLSERQVKTWFQNRRAKWRRLKQENP
QSNKKEELESLDSSCDQRQDLPSEQNKGASLDSSQCSPSPASQEDLESEI
SEDSDQEVDIEGDKSYFNAG PROX1 (SEQ ID NO: 7)
MPDHDSTALLSRQTKRRRVDIGVKRTVGTASAFFAKARATFFSAMNPQGS
EQDVEYSVVQHADGEKSNVLRKLLKRANSYEDAMMPFPGATIISQLLKNN
MNKNGGTEPSFQASGLSSTGSEVHQEDICSNSSRDSPPECLSPFGRPTMS
QFDMDRLCDEHLRAKRARVENIIRGMSHSPSVALRGNENEREMAPQSVSP
RESYRENKRKQKLPQQQQQSFQQLVSARKEQKREERRQLKQQLEDMQKQL
RQLQEKFYQIYDSTDSENDEDGNLSEDSMRSEILDARAQDSVGRSDNEMC
ELDPGQFIDRARALIREQEMAENKPKREGNNKERDHGPNSLQPEGKHLAE
TLKQELNTAMSQVVDTVVKVFSAKPSRQVPQVFPPLQIPQARFAVNGENH
NFHTANQRLQCFGDVIIPNPLDTFGNVQMASSTDQTEALPLVVRKNSSDQ
SASGPAAGGHHQPLHQSPLSATTGFTTSTFRHPFPLPLMAYPFQSPLGAP
SGSFSGKDRASPESLDLTRDTTSLRTKMSSHHLSHHPCSPAHPPSTAEGL
SLSLIKSECGDLQDMSEISPYSGSAMQEGLSPNHLKKAKLMFFYTRYPSS
NMLKTYFSDVKFNRCITSQLIKWFSNFREFYYIQMEKYARQAINDGVTST
EELSITRDCELYRALNMHYNKANDFEVPERFLEVAQITLREFFNAIIAGK
DVDPSWKKAIYKVICKLDSEVPEIFKSPNCLQELLHE KLF4 (SEQ ID NO: 8)
MRQPPGESDMAVSDALLPSFSTFASGPAGREKTLRQAGAPNNRWREELSH
MKRLPPVLPGRPYDLAAATVATDLESGGAGAACGGSNLAPLPRRETEEFN TABLE 1 -continued Human Transcription Factors And Other Factors
For Hepatic Conversion Of Human Fibroblasts DLLDLDFILSNSLTHPPESVAATVSSSASASSSSSPSSSGPASAPSTCSF
TYPIRAGNDPGVAPGGTGGGLLYGRESAPPPTAPFNLADINDVSPSGGFV
AELLRPELDPVYIPPQQPQPPGGGLMGKFVLKASLSAPGSEYGSPSVISV
SKGSPDGSHPVVVAPYNGGPPRTCPKIKQEAVSSCTHLGAGPPLSNGHRP
AAHDFPLGRQLPSRTTPTLGLEEVLSSRDCHPALPLPPGFHPHPGPNYPS
FLPDQMQPQVPPLHYQELMPPGSCMPEEPKPKRGRRSWPRKRTATHTCDY
AGCGKTYTKSSHLKAHLRTHTGEKPYHCDWDGCGWKFARSDELTRHYRKH
TGHRPFQCQKCDRAFSRSDHLALHMKRHF HNF1A (SEQ ID NO: 9)
MVSKLSQLQTELLAALLESGLSKEALIQALGEPGPYLLAGEGPLDKGESC
GGGRGELAELPNGLGETRGSEDETDDDGEDFTPPILKELENLSPEEAAHQ
KAVVETLLQEDPWRVAKMVKSYLQQHNIPQREVVDTTGLNQSHLSQHLNK
GTPMKTQKRAALYTWYVRKQREVAQQFTHAGQGGLIEEPTGDLETPKKGR
RNRFKWGPASQQILFQAYERQKNPSKEERETLVEECNRAECIQRGVSPSQ
AQGLGSNLVTEVRVYNWFANRRKEEAFRHKLAMDTYSGPPPGPGPGPALP
AHSSPGLPPPALSPSKVHGVRYGQPATSETAEVPSSSGGPLVTVSTPLHQ
VSPTGLEPSHSLLSTEAKLVSAAGGPLPPVSTLTALHSLEQTSPGLNGQP
QNLIMASLPGVMTIGPGEPASLGPTFTNTGASTLVIGLASTQAQSVPVIN
SMGSSLTTLQPVQFSQPLHPSYQQPLMPPVQSHVTQSPFMATMAQLQSPH
ALYSHKPEVAQYTHTGLLPQTMLITDTTNLSALASLTPTKQVFTSDTEAS
SESGLHTPASQATTLHVPSQDPAGIQHLQPAHRLSASPTVSSSSLVLYQS
SDSSNGQSHLLPSNHSVIETFISTQMASSSQ SV40 large T/Gene ID: 1489531 (SEQ ID NO: 10)
MDKVLNREESLQLMDLLGLERSAWGNIPLMRKAYLKKCKEFHPDKGGDEE
KMKKMNTLYKKMEDGVKYAHQPDFGGFWDATEIPTYGTDEWEQWWNAFNE
ENLFCSEEMPSSDDEATADSQHSTPPKKKRKVEDPKDFPSELLSFLSHAV
FSNRTLACFAIYTTKEKAALLYKKIMEKYSVTFISRHNSYNHNILFFLTP
HRHRVSAINNYAQKLCTFSFLICKGVNKEYLMYSALTRDPFSVIEESLPG
GLKEHDFNPEEAEETKQVSWKLVTEYAMETKCDDVLLLLGMYLEFQYSFE
MCLKCIKKEQPSHYKYHEKHYANAAIFADSKNQKTICQQAVDTVLAKKRV
DSLQLTREQMLTNRFNDLLDRMDIMFGSTGSADIEEWMAGVAWLHCLLPK
MDSVVYDFLKCMVYNIPKKRYWLFKGPIDSGKTTLAAALLELCGGKALNV
NLPLDRLNFELGVAIDQFLVVFEDVKGTGGESRDLPSGQGINNLDNLRDY
LDGSVKVNLEKKHLNKRTQIFPPGIVTMNEYSVPKTLQARFVKQIDFRPK
DYLKHCLERSEFLLEKRIIQSGIALLLMLIWYRPVAEFAQSIQSRIVEWK
ERLDKEFSLSVY QKMKFNVAMGIGVLDWLRNSDDDDEDSQENADKNEDG
GEKNMEDSGHETGIDSQSQGSFQAPQSSQSVHDHNQPYHICRGFTCFKKP
PTPPPEPET RB family gene p130 (SEQ ID NO: 11)
MPSGGDQSPPPPPPPAAAASDEEEEDDGEAEDAAPPAESPTPQIQQRFD
ELCSRLNMDEAARAEAWDSYRSMSESYTLEGNDLHWLACALYVACRKSVP
TVSKGTVEGNYVSLTRILKCSEQSLIEFFNKMKKWEDMANLPPHFRERTE
RLERNFTVSAVIFKKYEPIFQDIFKYPQEEQPRQQRGRKQRRQPCTVSEI
FHFCWVLFIYAKGNFPMISDDLVNSYHLLLCALDLVYGNALQCSNRKELV
NPNFKGLSEDFHAKDSKPSSDPPCIIEKLCSLHDGLVLEAKGIKEHFWKP
YIRKLYEKKLLKGKEENLTGFLEPGNFGESPKAINKAYEEYVLSVGNLDE
RIFLGEDAEEEIGTLSRCLNAGSGTETAERVQMKNILQQHFDKSKALRIS
TPLTGVRYIKENSPCVTPVSTATHSLSRLHTMLTGLRNAPSEKLEQILRT
CSRDPTQAIANRLKEMFEIYSQHFQPDEDFSNCAKEIASKHFRFAEMLYY
KVLESVIEQEQKRLGDMDLSGILEQDAFHRSLLACCLEVVTFSYKPPGNF
PFITEIFDVPLYHFYKVIEVFIRAEDGLCREVVKHLNQIEEQILDHLAWK
PESPLWEKIRDN ENRVPTCEEVMPPQNLERADEICIAGSPLTPRRVTEV
RADTGGLGRSITSPTTLYDRYSSPPASTTRRRLFVENDSPSDGGTPGRMP
PQPLVNAVPVQNVSGETVSVTPVPGQTLVTMATATVTANNGQTVTIPVQG
IANENGGITFFPVQVNVGGQAQAVTGSIQPLSAQALAGSLSSQQVTGTTL
QVPGQVAIQQISPGGQQQKQGQSVTSSSNRPRKTSSLSLFFRKVYHLAAV
RLRDLCAKLDISDELRKKIWTCFEFSIIQCPELMMDRHLDQLLMCAIYVM
AKVTKEDKSFQNIMRCYRTQPQARSQVYRSVLIKGKRKRRNSGSSDSRSH
QNSPTELNKDRTSRDSSPVMRSSSTLPVPQPSSAPPTPTRLTGANSDMEE
EERGDLIQFYNNIYIKQIKTFAMKYSQANMDAPPLSPYPFVRTGSPRRIQ
LSQNHPVYISPHKNETMLSPREKIFYYFSNSPSKRLREINSMIRTGETPT
KKRGILLEDGSESPAKRICPENHSALLRRLQDVANDRGSH RB family gene RB1 (SEQ ID NO: 12)
MPPKTPRKTAATAAAAAAEPPAPPPPPPEEDPEQDSGPEDLPLVRLEFE
ETEEPDFTALCQKLKIPDHVRERAWLTWEKVSSVDGVLGGYIQKKKELWG
ICIFIAAVDLDEMSFTFTELQKNIEISVHKFPNLLKEIDTSTKVDNAMSR
LLKKYDVLFALFSKLERTCELIYLTQPSSSISTEINSALVLKVSWITFLL
AKGEVLQMEDDLVISFQLMLCVLDYFIKLSPPMLLKEPYKTAVIPINGSP
RTPRRGQNRSARIAKQLENDTRIIEVLCKEHECNIDEVKNVYFKNFIPFM
NSLGLVTSNGLPEVENLSKRYEEIYLKNKDLDARLFLDHDKTLQTDSIDS
FETQRTPRKSNLDEEVNVIPPHTPVRTVMNTIQQLMMILNSASDQPSENL
ISYFNNCTVNPKESILKRVKDIGYIFKEKFAKAVGQGCVEIGSQRYKLGV
RLYYRVMESMLKSEEERLSIQNFSKLLNDNIFHMSLLACALEVVMATYSR
STSQNLDSGTDLSFPWILNVLNLKAFDFYKVIESFIKAEGNLTREMIKHL
ERCEHRIMESLAWLSDSPLFDLIKQSKDREGPTDHLESACPLNLPLQNNH
TAADMYLSPVRSPKKKGSTTRVNSTANAETQATSAFQTQKPLKSTSLSLF
YKKVYRLAYLRLNTLCERLLSEHPELEHII WTLFQHTLQNEYELMRDRH
LDQIMMCSMYGICKVKNIDLKFKIIVTAYKDLPHAVQETFKRVLIKEEEY
DSIIVFYNSVFMQRLKTNILQYASTRPPTLSPIPHIPRSPYKFPSSPLRI
PGGNIYISPLKSPYKISEGLPTPTKMTPRSRILVSIGESFGTSEKFQKIN
QMVCNSDRVLKRSAEGSNPPKPLKKLRFDIEGSDEADGSKHLPGESKFQQ
KLAEMTSTRTRMQKQKMNDSMDTSNKEEK RB family gene p107 (SEQ ID NO: 13)
MFEDKPHAEGAAVVAAAGEALQALCQELNLDEGSAAEALDDFTAIRGNYS
LEGEVTHWLACSLYVACR KSIIPTVGKGIMEGNCVSLTRILRSAKLSLI
QFFSKMKKWMDMSNLPQEFRERIERLERNFEVSTVIFKKYEPIFLDIFQN
PYEEPPKLPRSRKQRRIPCSVKDLFNFCWTLFVYTKGNFRMIGDDLVNSY
HLLLCCLDLIFANAIMCPNRQDLLNPSFKGLPSDFHTADFTASEEPPCII
AVLCELHDGLLVEAKGIKEHYFKPYISKLFDRKILKGECLLDLSSFTDNS
KAVNKEYEEYVLTVGDFDERIFLGADAEEEIGTPRKFTRDTPLGKLTAQA
NVEYNLQQHFEKKRSFAPSTPLTGRRYLREKEAVITPVASATQSVSRLQS
IVAGLKNAPSDQLINIFESCVRNPVENIMKILKGIGETFCQHYTQSTDEQ
PGSHIDFAVNRLKLAEILYYKILETVMVQETRRLHGMDMSVLLEQDIFHR
SLMACCLEIVLFAYSSPRTFPWIIEVLNLQPFYFYKVIEVVIRSEEGLSR
DMVKHLNSIEEQILESLAWSHDSALWEALQVSANKVPTCEEVIFPNNFET
GNGGNVQGHLPLMPMSPLMHPRVKEVRTDSGSLRRDMQPLSPISVHERYS
SPTAGSAKRRLFGEDPPKEMLMDKIITEGTKLKIAPSSSITAENVSILPG
QTLLTMATAPVTGTTGHKVTIPLHGVANDAGEITLIPLSMNTNQESKVKS
PVSLTAHSLIGASPKQTNLTKAQEVHSTGINRPKRTGSLALFYRKVYHLA
SVRLRDLCLKLDVSNELRRKIWTCFEFTLVHCPDLMKDRHLDQLLLCAFY
IMAKVTKEERTFQEIMKSYRNQPQANSHVYRSVLLKSIPREVVAYNKNIN
DDFEMIDCDLEDATKTPDCSSGPVKEERGDLIKFYNTIYVGRVKSFALKY
DLANQDHMMDAPPLSPFPHIKQQPGSPRRISQQHSIYISPHKNGSGLTPR
SALLYKFNGSPSKSLKDINNMIRQGEQRTKKRVIAIDSDAESPAKRVCQE
NDDVLLKRLQDVVSERANH Members of the HNF1 subfamily are transcription factors that contain a POU-homeodomain and bind to DNA as homodimers. Among them, HNF1A is highly expressed in the liver and is involved in the regulation of the expression of several liver-specific genes. Members of the HNF4 subfamily are nuclear receptors and bind to DNA either as homodimers or RXR heterodimers. HNF4A, as a transcription factor, binds DNA as a homodimer, and controls the expression of several genes, including HNF1A. This transcription factor plays a role in the development of the liver, kidney, and intestines. Alternative splicing of this gene results in multiple transcript variants.

Forkhead box proteins are a family of transcription factors that play important roles in regulating the expression of genes involved in cell growth, proliferation, differentiation, and longevity. Many forkhead box proteins are important to embryonic development. They are a subgroup of the helix-turn-helix class of proteins. The defining feature of these proteins is the forkhead box, a sequence of 80 to 100 amino acids forming a motif that binds to DNA. This forkhead motif is also known as the winged helix due to the butterfly-like appearance of the loops in the protein structure of the domain. FOXA1, FOXA2, and FOXA3, also known as Hnf3α, β, and γ, respectively, are members of the forkhead class of DNA-binding proteins. They are transcriptional activators for liver-specific transcripts such as albumin and transthyretin, and they also interact with chromatin.

As used herein, a particular transcription factor polypeptide (e.g., a Hnf polypeptide or Foxa polypeptide) refer to a member of a particular transcription factor family (e.g., one of the above-mentioned families), which include the corresponding transcription factors described above, their homologs, polypeptides having sequences thereof, and their mutant forms that retain substantial their transcription factor functions.

As disclosed herein, a forced expression of members of two or three of the above transcription factor families or subfamilies was sufficient to convert non-liver cells (such as adult fibroblast cells) to iHep cells. Accordingly, this invention provides agents that can convert non-liver cells to iHep cells, thereby supplying an unlimited cell source for modeling and understanding liver diseases, testing drug efficacy and toxicity, and cell replacement therapy.

Both polypeptides of the aforementioned factors and nucleic acids encoding the polypeptides can be used to practice the invention. While many polypeptide preparations can be used, a highly purified or isolated polypeptide is preferred. The terms "peptide," "polypeptide," and "protein" are used herein interchangeably to describe the arrangement of amino acid residues in a polymer. A peptide, polypeptide, or protein can be composed of the standard 20 naturally occurring amino acid, in addition to rare amino acids and synthetic amino acid analogs. They can be any chain of amino acids, regardless of length or post-translational modification (e.g., glycosylation or phosphorylation).

The peptide, polypeptide, or protein of this invention include recombinantly or synthetically produced fusion or chimeric versions of any of the aforementioned transcription factors, having the particular domains or portions that bind to the DNA site of the transcription factor and regulates the expression of a target gene of the transcription factor. The term also encompasses polypeptides that have an added amino-terminal methionine (useful for expression in pro-karyotic cells).

Within the scope of this invention are fusion proteins containing one or more of the afore-mentioned sequences and a heterologous sequence. A "chimeric" or "fusion" refers to the combination of amino acid sequences of different origin in one polypeptide chain by in-frame combination of their coding nucleotide sequences. The term explicitly encompasses internal fusions, i.e., insertion of sequences of different origin within a poly-peptide chain, in addition to fusion to one of its termini. A heterologous polypeptide, nucleic acid, or gene is one that originates from a foreign species, or, if from the same species, is substantially modified from its original form. Two fused domains or sequences are heterologous to each other if they are not adjacent to each other in a naturally occurring protein or nucleic acid.

The term "heterologous" is a relative term, which when used with reference to portions of a nucleic acid indicates that the nucleic acid comprises two or more subsequences that are not found in the same relationship to each other in nature. For instance, a nucleic acid that is recombinantly produced typically has two or more sequences from unrelated genes synthetically arranged to make a new functional nucleic acid, e.g., a promoter from one source and a coding region from another source. The two nucleic acids are thus heterologous to each other in this context. When added to a cell, the recombinant nucleic acids would also be heterologous to the endogenous genes of the cell. Thus, in a chromosome, a heterologous nucleic acid would include a non-native (non-naturally occurring) nucleic acid that has integrated into the chromosome, or a non-native (non-naturally occurring) extrachromosomal nucleic acid. In contrast, a naturally translocated piece of chromosome would not be considered heterologous in the context of this patent application, as it comprises an endogenous nucleic acid sequence that is native to the mutated cell.

An "isolated" or "purified" peptide, polypeptide, or protein refers to a peptide, polypeptide, or protein that has been separated from other proteins, lipids, and nucleic acids with which it is naturally associated. The polypeptide/protein can constitute at least 10% (i.e., any percentage between 10% and 100%, e.g., 20%, 30%, 40%, 50%, 60%, 70 %, 80%, 85%, 90%o, 95%, and 99%) by dry weight of the purified preparation. Purity can be measured by any appropriate standard method, for example, by column chromatography, polyacrylamide gel electrophoresis, or HPLC analysis. An isolated polypeptide/protein described in the invention can be purified from a natural source, produced by recombinant DNA techniques, or by chemical methods.

A "recombinant" peptide, polypeptide, or protein refers to a peptide, polypeptide, or protein produced by recombinant DNA techniques; i.e., produced from cells transformed by an exogenous DNA construct encoding the desired peptide. A "synthetic" peptide/polypeptide/protein refers to a peptide/polypeptide/protein prepared by chemical synthesis. The term "recombinant" when used with reference, e.g., to a cell, nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified.

"Overexpression" refers to the expression of a RNA or polypeptide or protein encoded by a DNA introduced into a host cell, wherein the RNA or polypeptide or protein is either not normally present in the host cell, or wherein the RNA or polypeptide or protein is present in said host cell at a higher level than that normally expressed from the endogenous gene encoding the RNA or polypeptide or protein. Overexpression or forcing expression of a factor can be carried out using various techniques known in the art, including but not limited to nucleic acid transfection, virus infection, and protein transduction.

The amino acid composition of each of the above-mentioned peptides/polypeptides/proteins may vary without disrupting their factor functions, e.g., the ability to bind to a DNA site and enhance or inhibit the respective target gene expression. For example, it can contain one or more conservative amino acid substitutions. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), β-branched side chains (e.g., threonine, valine, isoleucine) and aromatic side chains (e.g., tyrosine, phenylalanine, tryptophan, histidine). Thus, a predicted nonessential amino acid residue in one of the above-described factors (e.g., SEQ ID NOs: 1-13) is preferably replaced with another amino acid residue from the same side chain family. Alternatively, mutations can be introduced randomly along all or part of the sequences, such as by saturation mutagenesis, and the resultant mutants can be screened for the ability to bind to the respective DNA site(s) and trigger the respective cellular response to identify mutants that retain the activity as descried below in the examples.

A functional equivalent of a peptide, polypeptide, or protein of this invention refers to a polypeptide derivative of the peptide, polypeptide, or protein, e.g., a protein having one or more point mutations, insertions, deletions, truncations, a fusion protein, or a combination thereof. It retains substantially the activity to one of the above-mentioned factors. The isolated polypeptide of this invention can contain one of SEQ ID NOs: 1-13, or a functional equivalent or fragment thereof. In general, the functional equivalent is at least 75% (e.g., any number between 75% and 100%, inclusive, e.g., 75 %, 80%, 85%, 90%, 95%, and 99%) identical to one of SEQ ID NOs: 1-13.

A polypeptide described in this invention can be induced into cells of interest via protein transduction. The polypeptide can be obtained as a recombinant polypeptide. For example, to prepare a recombinant polypeptide, a nucleic acid encoding it can be linked to another nucleic acid encoding a fusion partner, e.g., glutathione-s-transferase (GST), 6x-His epitope tag, or M13 Gene 3 protein. The resultant fusion nucleic acid expresses in suitable host cells a fusion protein that can be isolated by methods known in the art. The isolated fusion protein can be further treated, e.g., by enzymatic digestion, to remove the fusion partner and obtain the recombinant polypeptide of this invention. Alternatively, the peptides/polypeptides/proteins of the invention can be chemically synthesized (see e.g., Creighton, "Proteins: Structures and Molecular Principles," W.H. Freeman & Co., NY, 1983). For additional guidance, skilled artisans may consult Ausubel et al. (Current Protocols in Molecular Biology and Short Protocols in Molecular Biology, 3rd Ed. 1987 & 1995), Sambrook et al. (Molecular Cloning, A Laboratory Manual, Cold Spring Harbor Press, Cold Spring Harbor, N.Y., 1989), and chemical synthesis Gait, M. J. Ed. (Oligonucleotide Synthesis, IRL Press, Oxford, 1984).

Due to their functions as transcription factors, the above-disclosed polypeptides can be associated with, e.g., conjugated or fused to, one or more of an amino acid sequence comprising a nuclear localization signal (NLS), a cell-penetrating peptide (CPP) sequence, and the like. In this manner, a composition of the invention as discussed below can include a transport enhancer. For example, the composition may include a penetration enhancing agent, such as MSM, for the delivery of the transcription factors or related therapeutic polypeptides to a cell and/or through the cell membrane and into the nucleus of the cell. The transcription factors then function to regulate transcription of target genes, thereby resulting in an induction of iHep cells. The transcription factors may be delivered by itself or as a fusion with one or more of an NLS, CPP, and/or other domains. See, e.g., Tachikawa et al. PNAS (2004) vol. 101, no. 42:15225-15230, US 20090156503.

A cell-penetrating peptide (CPP) generally consists of less than 30 amino acids and has a net positive charge. CPPs internalize in living animal cells in vitro and in vivo in an endocytotic or receptor/energy-independent manner. There are several classes of CPPs with various origins, from totally protein-derived CPPs via chimeric CPPs to completely synthetic CPPs. Examples of CPPs are known in the art. See, e.g., U.S. Application Nos. 20090099066 and 20100279918. It is known that CPPs can deliver an exogenous protein to various cells.

Although the above-described factors to be delivered to a cell may be fusion proteins including an NLS and/or CPP, in certain instances, the protein does not include an NLS and/or a CPP as the transport enhancer may serve the function of delivering the biologically active agent directly to the cell, and/or through the cell membrane into the cytoplasm of the cell and/or into the nucleus of the cell as desired. For instance, in certain instances, it may be desirable to deliver a biologically active protein to the cell wherein the protein is not conjugated or fused to another molecule. In such instance, any biologically active protein may be delivered directly in conjunction with the transport enhancer.

All of naturally occurring versions, genetically engineered versions, and chemically synthesized versions of the above-mentioned transcription factors or other factors can be used to practice the invention disclosed therein. Polypeptides obtained by recombinant DNA technology may have the same amino acid sequence as a naturally occurring version (e.g., one of SEQ ID NOs: 1-13) or a functionally equivalent thereof. They also include chemically modified versions. Examples of chemically modified polypeptides include polypeptides subjected to conformational change, addition or deletion of a side chain, and those to which a compound such as polyethylene glycol has been bound. Once purified and tested by standard methods or according to the method described in the examples below or other methods known in the art, the polypeptides can be included in a suitable composition.

For expressing the above-mentioned factors, the invention provides a nucleic acid that encodes any of the polypeptides mentioned above. Preferably, the nucleotide sequences are isolated and/or purified. A nucleic acid refers to a DNA molecule (e.g., but not limited to, a cDNA or genomic DNA), an RNA molecule (e.g., but not limited to, an mRNA), or a DNA or RNA analog. A DNA or RNA analog can be synthesized from nucleotide analogs. The nucleic acid molecule can be single-stranded or double-stranded. An "isolated nucleic acid" is a nucleic acid the structure of which is not identical to that of any naturally occurring nucleic acid or to that of any fragment of a naturally occurring genomic nucleic acid. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein.

The present invention also provides recombinant constructs having one or more of the nucleotide sequences described herein. Examples of the constructs include a vector, such as a plasmid or viral vector, into which a nucleic acid sequence of the invention has been inserted, in a forward or reverse orientation. In a preferred embodiment, the construct further includes regulatory sequences, including a promoter, operably linked to the sequence. Large numbers of suitable vectors and promoters are known to those of skill in the art, and are commercially available. Appropriate cloning and expression vectors for use with prokaryotic and eukaryotic hosts are also described in Sambrook et al. (2001, Molecular Cloning: A Laboratory Manual, Cold Spring Harbor Press).

Examples of expression vectors include chromosomal, nonchromosomal and synthetic DNA sequences, e.g., Simian virus 40 (SV40), bacterial plasmids, phage DNA, baculovirus, yeast plasmids, vectors derived from combinations of plasmids and phage DNA, viral DNA such as vaccinia, adenovirus, fowl pox virus, and pseudorabies. However, any other vector may be used as long as it is replicable and viable in the host. The appropriate nucleic acid sequence may be inserted into the vector by a variety of procedures. In general, a nucleic acid sequence encoding one of the polypeptides described above can be inserted into an appropriate restriction endonuclease site(s) by procedures known in the art. Such procedures and related sub-cloning procedures are within the scope of those skilled in the art.

The nucleic acid sequence in the aforementioned expression vector is preferably operatively linked to an appropriate transcription control sequence (promoter) to direct mRNA synthesis. Examples of such promoters include: the retroviral long terminal (LTR) or SV40 promoter, the *E. coli* lac or trp promoter, the phage lambda PL promoter, and other promoters known to control expression of genes in prokaryotic or eukaryotic cells or viruses. The expression vector can also contain a ribosome binding site for translation initiation, and a transcription terminator. The vector may include appropriate sequences for amplifying expression. In addition, the expression vector preferably contains one or more selectable marker genes to provide a phenotypic trait for selection of transformed host cells such as dihydrofolate reductase or neomycin resistance for eukaryotic cell cultures, or such as tetracycline or ampicillin resistance in *E. coli*.

The vector containing the appropriate nucleic acid sequences as described above, as well as an appropriate promoter or control sequence, can be employed to transform, transfect, or infect an appropriate host to permit the host to express the polypeptides described above (e.g., one of SEQ ID NOs: 1-13). Examples of suitable expression hosts include bacterial cells (e.g., *E. coli, Streptomyces, Salmonella typhimurium*), fungal cells (yeast), insect cells (e.g., *Drosophila* and *Spodoptera frugiperda* (Sf9)), animal cells (e.g., CHO, COS, and HEK 293), adenoviruses, and plant cells. The selection of an appropriate host is within the scope of those skilled in the art. In some embodiments, the present invention provides methods for producing the above mentioned polypeptides by transfecting a host cell with an expression vector having a nucleotide sequence that encodes one of the polypeptides. The host cells are then cultured under a suitable condition, which allows for the expression of the polypeptide.

As mentioned above, a nucleic acid sequence of this invention can be a DNA or RNA. The terms "RNA," "RNA molecule," and "ribonucleic acid molecule" are used interchangeably herein, and refer to a polymer of ribonucleotides. The term "DNA" or "DNA molecule" or "deoxyribonucleic acid molecule" refers to a polymer of deoxyribonucleotides. DNA and RNA can be synthesized naturally (e.g., by DNA replication or transcription of DNA, respectively). RNA can be post-transcriptionally modified. DNA and RNA also can be chemically synthesized. DNA and RNA can be single-stranded (i.e., ssRNA and ssDNA, respectively) or multi-stranded (e.g., double-stranded, i.e., dsRNA and dsDNA, respectively).

Starting Cells

As disclosed herein, the invention provides methods of generating iHep cells from non-liver cells (i.e., the starting cells). In one example, the methods involve introducing into starting cells heterologous transcription factors discussed above or nucleic acids encoding them so that the starting cells over-express the transcription factors. See, e.g., FIG. 1A. The modified starting cells are then cultured for a period of time, e.g., 10-14 days to generate iHep cells.

Various cells from a subject or animal can be used as the starting cells. For example, somatic cells can be used as the starting cells. As used herein, the term "somatic cell" refers to any cell other than a germ cell, a cell present in or obtained from a pre-implantation embryo, or a cell resulting from proliferation of such a cell in vitro. Stated another way, a somatic cell refers to any cell forming the body of an organism, as opposed to a germline cell. In mammals, germline cells (also known as "gametes") are the spermatozoa and ova which fuse during fertilization to produce a cell called a zygote, from which the entire mammalian embryo develops. Every other cell type in the mammalian body—apart from the sperm and ova, the cells from which they are made (gametocytes) and undifferentiated, pluripotent, embryonic stem cells—is a somatic cell: internal organs, skin, bones, blood, and connective tissue are all made up of somatic cells. In some embodiments the somatic cell is a "non-embryonic somatic cell," by which is meant a somatic cell that is not present in or obtained from an embryo and does not result from proliferation of such a cell in vitro. In some embodiments the somatic cell is an "adult somatic cell," by which is meant a cell that is present in or obtained from an organism other than an embryo or a fetus or results from proliferation of such a cell in vitro. Unless otherwise indicated, the compositions and methods for reprogramming a somatic cell described herein can be performed both in vivo and in vitro (where in vivo is practiced when a somatic cell is present within a subject, and where in vitro is practiced using an isolated somatic cell maintained in culture). The term excludes gametes, germ cells, gametocytes, fertilized eggs or embryos at development stages before the blastula stage.

In some embodiments, the starting cells are stem cells. The stem cells useful for the method described herein include but not limited to embryonic stem cell, mesenchymal stem cells, bone-marrow derived stem cells, hematopoietic stem cells, chrondrocytes progenitor cells, epidermal stem cells, gastrointestinal stem cells, neural stem cells, hepatic stem cells, adipose-derived mesenchymal stem cells, pancreatic progenitor cells, hair follicular stem cells, endothelial progenitor cells, and smooth muscle progenitor cells. The stem cells can be pluripotent or multipotent. In some embodiments, the stem cell is an adult, fetal or embryonic stem cell. The stem cells can be isolated from umbilical, placenta, amniotic fluid, chorion villi, blastocysts, bone marrow, adipose tissue, brain, peripheral blood, blood vessels, skeletal muscle, and skin.

In some embodiments, the starting cells are differentiated cells. Examples include a fibroblast, an epithelium cell, a blood cell, a neuron, an embryonic cell, or a cell derived from a tissue or organ of a subject. These differentiated cells differ from stem cells in that differentiated cells generally do not undergo self-renewing proliferation while stem cells can undergo self-renewing cell division to give rise to phenotypically and genotypically identical daughters for an indefinite time and ultimately can differentiate into at least one final cell type.

The term "differentiated cell" encompasses any somatic cell that is not, in its native form, pluripotent, as that term is defined herein. Thus, the term a "differentiated cell" also encompasses cells that are partially differentiated, such as multipotent cells, or cells that are stable, non-pluripotent partially reprogrammed, or partially differentiated cells, generated using any of the compositions and methods described herein. In some embodiments, a differentiated cell is a cell that is a stable intermediate cell, such as a non-pluripotent, partially reprogrammed cell. It should be noted that placing many primary cells in culture can lead to some loss of fully differentiated characteristics. Thus, simply culturing such differentiated or somatic cells does not render these cells non-differentiated cells (e.g. undifferentiated cells) or pluripotent cells. The transition of a differentiated cell (including stable, non-pluripotent partially reprogrammed cell intermediates) to pluripotency requires a reprogramming stimulus beyond the stimuli that lead to partial loss of differentiated character upon placement in culture. Reprogrammed and, in some embodiments, partially reprogrammed cells, also have the characteristic of having the capacity to undergo extended passaging without loss of growth potential, relative to parental cells having lower developmental potential, which generally have capacity for only a limited number of divisions in culture. In some embodiments, the term "differentiated cell" also refers to a cell of a more specialized cell type (i.e., decreased developmental potential) derived from a cell of a less specialized cell type (i.e., increased developmental potential) (e.g., from an undifferentiated cell or a reprogrammed cell) where the cell has undergone a cellular differentiation process.

The terms "proliferation" and "expansion" as used interchangeably herein refer to an increase in the number of cells of the same type by division. The term "differentiation" refers to a developmental process whereby cells become specialized for a particular function, for example, where cells acquire one or more morphological characteristics and/or functions different from that of the initial cell type. The term includes both lineage commitment and terminal differentiation processes. Differentiation may be assessed, for example, by monitoring the presence or absence of lineage markers, using immuno-histochemistry or other procedures known to a skilled in the art. Differentiated progeny cells derived from progenitor cells may be, but are not necessarily, related to the same germ layer or tissue as the source tissue of the stem cells. For example, neural progenitor cells and muscle progenitor cells can differentiate into hematopoietic cell lineages.

To convert the differentiated cells to iHep cells, one needs to reprogram the differentiated cells so that they proliferate. This can be achieved by forced expression of a protein the enhance cell proliferation, such as the SV 40 large T antigen by inactivating or down-regulating one or more components of the cellular senescence pathway that inhibits induced pluripotent stem cell reprogramming, such as one or more of the Rb family genes.

Various means can be used for that purpose. In one embodiment, one can use the RNA interference (RNAi) technology or antisense technology. For example, one can generate a nucleic acid sequence that encode a small interference RNA (e.g., an RNAi agent) that targets one or more of genes encoding a component of the cellular senescence pathway and inhibits its expression or activity.

The term "RNAi agent" refers to an RNA, or analog thereof, having sufficient sequence complementarity to a target RNA to direct RNA interference. Examples also include a DNA that can be used to make the RNA. RNA interference (RNAi) refers to a sequence-specific or selective process by which a target molecule (e.g., a target gene, protein or RNA) is down-regulated. Generally, an interfering RNA ("iRNA") is a double stranded short-interfering RNA (siRNA), short hairpin RNA (shRNA), or single-stranded micro-RNA (miRNA) that results in catalytic degradation of specific mRNAs, and also can be used to lower or inhibit gene expression.

The term "short interfering RNA" or "siRNA" (also known as "small interfering RNAs") refers to an RNA agent, preferably a double-stranded agent, of about 10-50 nucleotides in length, preferably about 17, 18, 19, 20, 21, 22, 23, 24, or 25 nucleotides in length, the strands optionally having overhanging ends comprising, for example 1, 2 or 3 overhanging nucleotides (or nucleotide analogs), which is capable of directing or mediating RNA interference. Naturally-occurring siRNAs are generated from longer dsRNA molecules (e.g., >25 nucleotides in length) by a cell's RNAi machinery (e.g., Dicer or a homo log thereof).

The term "shRNA" refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region.

The term "miRNA" or "microRNA" refers to an RNA agent, preferably a single-stranded agent, of about 10-50 nucleotides in length, preferably between about 15-25nucleotides in length, more preferably about 17, 18, 19, 20, 21, 22, 23, 24, or 25 nucleotides in length, which is capable of directing or mediating RNA interference. Naturally-occurring miRNAs are generated from stem-loop precursor RNAs (i.e., pre-miRNAs) by Dicer. The term microRNA (or "miRNA") is used interchangeably with the term "small temporal RNA" (or "stRNA") based on the fact that naturally-occurring microRNAs (or "miRNAs") have been found to be expressed in a temporal fashion (e.g., during development).

Thus, also within the scope of this invention is utilization of RNAi featuring degradation of RNA molecules (e.g., within a cell). Degradation is catalyzed by an enzymatic, RNA-induced silencing complex (RISC). A RNA agent having a sequence sufficiently complementary to a target RNA sequence (e.g., one or more of the above-mentioned genes of the cellular senescence pathway) to direct RNAi means that the RNA agent has a homology of at least 50%, (e.g., 50%, 60%, 70%, 80%, 90%, 95%, 98%, 99%, or 100% homology) to the target RNA sequence so that the two are sufficiently complementary to each other to hybridize and trigger the destruction of the target RNA by the RNAi machinery (e.g., the RISC complex) or process. A RNA agent having a "sequence sufficiently complementary to a target RNA sequence to direct RNAi" also means that the RNA agent has a sequence sufficient to trigger the translational inhibition of the target RNA by the RNAi machinery or process. A RNA agent also can have a sequence sufficiently complementary to a target RNA encoded by the target DNA sequence such that the target DNA sequence is chromatically silenced. In other words, the RNA agent has a sequence sufficient to induce transcriptional gene silencing, e.g., to down-modulate gene expression at or near the target DNA sequence, e.g., by inducing chromatin structural changes at or near the target DNA sequence.

The above-mentioned polynucleotides can be delivered to cells in vitro or in vivo using polymeric, biodegradable microparticle or microcapsule delivery devices known in the art. Another way to achieve uptake of the polynucleotides is using liposomes, prepared by standard methods. The polynucleotide can be incorporated alone into these delivery vehicles or co-incorporated with tissue-specific antibodies. Alternatively, one can prepare a molecular conjugate composed of a plasmid or other vector attached to poly-L-lysine by electrostatic or covalent forces. Poly-L-lysine binds to a ligand that can bind to a receptor on target cells (Cristiano, et al., 1995, J. Mol. Med. 73:479). Alternatively, tissue specific targeting can be achieved by the use of tissue-specific transcriptional regulatory elements that are known in the art. Delivery of naked DNA (i.e., without a delivery vehicle) to an intramuscular, intradermal, or subcutaneous site is another means to achieve in vivo expression.

siRNA, miRNA, and asRNA (antisense RNA) molecules can be designed by methods well known in the art. siRNA, miRNA, and asRNA molecules with homology sufficient to provide sequence specificity required to uniquely degrade any RNA can be designed using programs known in the art, including, but not limited to, those maintained on websites for AMBION, Inc. and DHARMACON, Inc. Systematic testing of several designed species for optimization of the siRNA, miRNA, and asRNA sequences can be routinely performed by those skilled in the art. Considerations when designing short interfering nucleic acid molecules include, but are not limited to, biophysical, thermodynamic, and structural considerations, base preferences at specific positions in the sense strand, and homology. These considerations are well known in the art and provide guidelines for designing the above-mentioned RNA molecules.

An antisense polynucleotide (preferably DNA) of the present invention can be any antisense polynucleotide so long as it possesses a base sequence complementary or substantially complementary to that of the DNA encoding a key component of the cellular senescence pathway that inhibits induced pluripotent stem cell reprogramming and capable of suppressing expression of the component polypeptide. The base sequence can be at least about 70%, 80%, 90%, or 95% homology to the complement of the DNA encoding the polypeptide. These antisense DNAs can be synthesized using a DNA synthesizer.

The antisense DNA of the present invention may contain changed or modified sugars, bases or linkages. The antisense DNA, as well as the RNAi agent mentioned above, may also be provided in a specialized form such as liposomes, microspheres, or may be applied to gene therapy, or may be provided in combination with attached moieties. Such attached moieties include polycations such as polylysine that act as charge neutralizers of the phosphate backbone, or hydrophobic moieties such as lipids (e.g., phospholipids, cholesterols, etc.) that enhance the interaction with cell membranes or increase uptake of the nucleic acid. Preferred examples of the lipids to be attached are cholesterols or derivatives thereof (e.g., cholesteryl chloroformate, cholic acid, etc.). These moieties may be attached to the nucleic acid at the 3' or 5' ends thereof and may also be attached thereto through a base, sugar, or intramolecular nucleoside linkage. Other moieties may be capping groups specifically placed at the 3' or 5' ends of the nucleic acid to prevent degradation by nucleases such as exonuclease, RNase, etc. Such capping groups include, but are not limited to, hydroxyl protecting groups known in the art, including glycols such as polyethylene glycol, tetraethylene glycol and the like. The inhibitory action of the antisense DNA can be examined using a cell-line or animal based gene expression system of the present invention in vivo and in vitro.

The above-discussed nucleic acids encoding one or more of the polypeptides mentioned above or RNAi agents can be cloned in a vector for delivering to cells in vitro or in vivo. For in vivo uses, the delivery can target a specific tissue or organ (e.g., liver). Targeted delivery involves the use of vectors (e.g., organ-homing peptides) that are targeted to specific organs or tissues after systemic administration. For example, the vector can have a covalent conjugate of avidin and a monoclonal antibody to a liver specific protein.

In certain embodiments, the present invention provides methods for in vivo production of the above-mentioned iHep cells. Such method would achieve its therapeutic effect by introduction of the nucleic acid sequences into cells or tissues of a human or a non-human animal in need of an increase in liver function. Delivery of the nucleic acid sequences can be achieved using a recombinant expression vector such as a chimeric virus or a colloidal dispersion system. Preferred for therapeutic delivery of the nucleic acid sequences is the use of targeted liposomes.

Various viral vectors which can be utilized for gene therapy disclosed herein include, adenovirus, herpes virus, vaccinia, or, preferably, an RNA virus such as a retrovirus and a lentivirus. Preferably, the retroviral vector is a lentivirus or a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes.

Recombinant lentivirus has the advantage of gene delivery into either dividing or non-dividing mammalian cells. The HIV-1 based lentivirus can effectively transduce a broader host range than the Moloney Leukemia Virus (MoMLV)-base retroviral systems. Preparation of the recombinant lentivirus can be achieved using the pLenti4/V5-DEST™, pLenti6/V5-DEST™ or pLenti vectors together with ViraPower™.

All of these vectors can transfer or incorporate a gene for a selectable marker so that transduced cells can be identified and generated. Retroviral vectors can be made target-specific by attaching, for example, a sugar, a glycolipid, or a protein. Preferred targeting is accomplished by using a target-specific antibody or hormone that has a receptor in the target. Those of skill in the art will recognize that specific polynucleotide sequences can be inserted into the retroviral genome or attached to a viral envelope to allow target specific delivery of the retroviral vector.

Another targeted system for delivery of nucleic acids is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. RNA, DNA, and intact virions can be encapsulated within the aqueous interior and delivered to cells in a biologically active form. Methods for efficient gene transfer using a liposome vehicle are known in the art. The composition of the liposome is usually a combination of phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Exemplary phospholipids include egg phosphatidylcholine, dipalmitoylphosphatidylcholine, and distearoylphosphatidylcholine. The targeting of liposomes is also possible based on, for example, organ-specificity, cell-specificity, and organelle-specificity and is known in the art.

When used in vivo, it is desirable to use a reversible delivery-expression system. To that end, the Cre-loxP or FLP/FRT system and other similar systems can be used for reversible delivery-expression of one or more of the above-described nucleic acids. See WO2005/112620, WO2005/039643, U.S. Applications 20050130919, 20030022375, 20020022018, 20030027335, and 20040216178. In particular, the reversible delivery-expression system described in US Application NO 20100284990 can be used to provide a selective or emergency shut-off.

Cell Conversion

To covert the starting cells to iHep cells, the starting cells are cultured in culture medium, which is a nutrient-rich buffered aqueous solution capable of sustaining cell growth. Suitable culture media include but not limited to high glucose Dulbecco's Modified Eagle's Medium (DMEM), DMEM/F-12, DMEM/F-15, Liebovitz L-15, RPMI 1640, Iscove's modified Dubelcco's media (IMDM), and Opti-MEM SFM. Chemically defined medium comprises a minimum essential medium such as Iscove's Modified Dulbecco's Medium (IMDM), supplemented with human serum albumin, human Ex Cyte lipoprotein, transferrin, insulin, vitamins, essential and non-essential amino acids, sodium pyruvate, glutamine and a mitogen. A mitogen refers to an agent that stimulates cell division of a cell. An agent can be a chemical, usually some form of a protein that encourages a cell to commence cell division, triggering mitosis. In one embodiment, serum free media such as those described in WO96/39487, and the "complete media" as described in U.S. Pat. No. 5,486,359. In one preferred embodiment, one can use the media descried in the examples below.

The starting cells are plated for culturing and differentiation onto an adherent substrate. In general, adherent substrates may be any substantially hydrophilic substrate. Adherent substrate surfaces may be generated via surface coating, e.g., coating of the polymeric or treated polymeric surfaces as above. In a non-limiting example, the coating may involve suitable poly-cations, such as, e.g., poly-ornithine or poly-lysine. For example, a coating can contain one or more components of extracellular matrix, e.g., the ECM proteins fibrin, laminin, collagen, preferably collagen type 1, glycosaminoglycans, e.g., heparin or heparan sulphate, fibronectin, gelatine, vitronectin, elastin, tenascin, aggrecan, agrin, bone sialoprotein, cartilage matrix protein, fibrinogen, fibulin, mucins, entactin, osteopontin, plasminogen, restrictin, serglycin, SPARC/osteonectin, versican, thrombo-spondin 1, or cell adhesion molecules including cadherins, connexins, selectins, by themselves or in various combinations.

In a preferred embodiment, the coating contains collagen, e.g., collagen type 1. Such coating may be particularly preferred during the differentiation protocol, since collagen, especially, collagen type 1, has been shown to aid maintenance of hepatocyte function, differentiation state and hepatic gene transcription.

After culturing for a period of time, the cultured cell population contains iHep cells. It shall be understood that the cultured cell population encompasses the progeny of a starting cell population obtainable as above, or the progeny of a fraction of the said cell population. Such progeny may be a non-clonal line, i.e., containing the offspring of multiple cells or cells from multiple colonies of a starting cell population obtainable as above; or such progeny may be a clonal sub-line, i.e., derived from a single cell or a single colony of the starting cell population.

Then, one can obtain a sample of the cultured cell population and confirm their status by examining one or more markers indicative of a hepatocyte-phenotype. The iHep cells generated according to the methods described herein should express characteristic markers indicative of liver function. For example, the cells are expected to express enzymes and other polypeptides associated with carbohydrate, protein, and lipid metabolism. In one embodiment, they express a polypeptide associated with glycogen storage, glucose-6-phosphatase activity, decomposition of red blood cells, or plasma protein synthesis. In another, a cell of the invention expresses a polypeptide associated with urea production or synthesis of bile. In yet another embodiment, the cell expresses a polypeptide associated with cytochrome p450 (CYP3A4) activity, which is responsible for xenobiotic detoxification. In some other embodiments, the cell expresses arginase I, which functions in physiologic detoxification and urea production.

The expression of a hepatocyte phenotype in a cell of the invention may be evaluated by analyzing mRNA. In some embodiments, the mRNAs of key enzymes and proteins expressed in the hepatocyte-like cell are evaluated by quantitative reverse transcriptase polymerase chain reaction (qRT-PCR). Alternatively, iHep cells are characterized for a hepatocyte phenotype by analyzing the expression of hepatocyte markers (e.g., polypeptides characteristically expressed in hepatocytes) via an immunoassay (such as an immunocytochemical assay or a Western blot) or by analyzing characteristic hepatocyte metabolism pathways. Examples of useful markers and pathways are described in Tables 2 and 3 and in the examples below.

One can also confirm the iHep cell status by evaluating their biological functions as shown in the examples below. More specifically, the cells can be evaluated for glycogen storage using Periodic Acid Schiff (PAS) functional staining for glycogen granules (Thompson S W. in Selected Histochemical and Histopathological Methods, C. C. Tomas, Sprungfield, Ill. 1966; Sheehan D C. and Hrapchak, B B. in Theory and Practice of Histotechnology, 2nd Ed., Battelle memorial Institute, Columbus, Ohio, 1987)), for urea production using colorimetrically (Miyoshi et al., 1998, J Biomater Sci Polym Ed 9: 227-237), for bile secretion by fluorescein diacetate time lapse assay (Gebhart et al. J. Cell Sci. 1982, 56233-244), for lipid synthesis by oil red O staining, and for glycogen synthesis (Passonneau et al. 1974, Anal. Biochem. 60:405-415).

Once the hepatocyte phenotype is confirmed, the iHep cells can be further purified or enriched according to the method described in the examples below or other methods known in the art. The resulting purified or enriched cell population contains at least 60%, e.g., at least 65%, 70%, 75%, 80%, 85%, 90%, 95%, 99% of iHep cells. The cells can be used in various ways as disclosed below.

As disclosed in the examples below, functionally mature human hepatocyte-like cells were successfully generated directly from fibroblasts. The results showed that human cells are resistant to reprogramming, and multiple optimizations were applied to develop a new strategy for efficient hiHep induction. For example, hiHep cells were induced by a set of factors consisting of FOXA3, HNF1A and HNF4A. Intriguingly, it is known that HNF4A activates the HNF1A promoter and Hnf4a alone with Foxa1, 2 or 3 are sufficient to induce mouse iHep cells. However, additional expression of HNF1A is necessary for conversion of human fibroblasts. This may be partially explained by the fact that the transcriptional binding sites and regulation differ in human and mouse liver cells, despite that these factors are essential for hepatic gene expression in both human and mouse cells.

It was also found that the removal of C/EBPβ and GATA4 enhanced hepatic gene expression. During the induction of hiHep cells, the exogenous transcription factors trigger a dynamic change of cell identity. This process is different from the static cell identity of mature hepatocytes or liver development. It is likely that during hepatic conversion the specific combination of transcription factors form a regulatory network distinctive from that in hepatocytes. It is thus possible that the roles of C/EBPβ and GATA4 in hepatic conversion are dependent on the specific combination of factors used for hiHep induction.

Proliferation arrest is a major hurdle for the application of terminally differentiated cells generated by forced lineage change. For example, p19Arf inactivation was previously used to expand mouse iHep cells (Huang et al., (2011) Nature 475, 386-389.). Yet, that was insufficient for human cells. This is likely due to the difference between the two species, because the inactivation of p53 alone was able to immortalize mouse fibroblasts, but was not enough to enhance proliferation of human cells in vitro. As disclosed herein, it was found that LT expression enabled hiHep cells to proliferate. ALB and AAT expressing cell numbers were increased in hiHep$^{LT}$ cells, likely resulted from continuous lineage conversion during proliferation of these cells.

hiHep$^{LT}$ cells therefore provide the opportunity to definitively demonstrate the therapeutic effects of hiHep cells on metabolic liver disease and acute liver failure. Moreover, repopulation of hiHep cells in Fah-deficient mice presents a new strategy for development of humanized animal models for biomedical research. Intriguingly, hiHep$^{LT}$ cells appeared to be non-tumorigenic, partially due to attenuated SV40 LT levels in hiHep$^{LT}$ cells after transplantation in mice. Also, this observation is in line with previous findings that SV40 LT alone is not sufficient to induce tumorigenesis in mammalian cells (Land et al., Nature 304, 596-602). Although the expression of LT in hiHep cells is not a concern for in vitro disease modelling and application in extracorporeal bio-artificial liver supporting devices (Carpentier et al., (2009), Gut 58, 1690-1702), a controllable LT expression system or other safe measures to expand hiHep cells should be developed for cell replacement therapies. Similarly, for the same reasons, the inactivation of the Rb family genes should also be carried out in a controllable manner.

Techniques and methods for controllable or inducible gene expression or inhibition are well known in the art. Examples of such techniques and methods include expression systems having inducible promoters or enhancers, controllable systems based on Cre-LoxP, FLP/FRT, and the alike. See, e.g., WO2005/039643, WO2005/112620, U.S. Pat. No. 6,576,469, U.S. Patent Application Publication Nos. 200920080124379, 20080241116, 20080060099, 20050130919, 20030022375, 20020022018, and 20040216178. For controllable or inducible inhibition or reduction of gene expression, one can use RNAi-based knocking down technology described above. Also useful are systems and methods based on the CRISPR/Cas system. See, e.g., WO 2013176772, Cong et al., (2012), Science 339 (6121): 819-823, Jinek et al., (2012), Science 337 (6096): 816-821, Mali et al, (2013), Science 339 (6121): 823-826, Gasiunas et al., (2012), Proc Natl Acad Sci USA 109 (39): E2579-E2586, and Cho et al., (2013) Nature Biotechnology 31, 230-232. Hou et al., Proc Natl Acad Sci USA. 2013 Sep. 24; 110(39):15644-9, Mojica et al., Microbiology. 2009 March; 155(Pt 3):733-40, and http://www.addgene.org/CRISPR/. All of these references are incorporated herein in their entireties.

Uses of iHep Cells

The above-described iHep cells, or a cell population containing them, or the progenies thereof, can be used in a variety of applications. One example is treating diseases or liver metabolic deficiencies, e.g., liver metabolic deficiencies, liver degenerative diseases or fulminant liver failure, liver infectious diseases, etc. via transplantation or implantation. Other examples include elucidating the mechanism of liver diseases and infections; screening cytotoxic compounds, carcinogens, mutagens growth/regulatory factors, pharmaceutical compounds, etc., in vitro; evaluating metabolism, pharmacogenetics, or toxicity of an agent (e.g., a new or known drug); studying the pharmacological mechanism by which drugs and/or growth factors operate; diagnosing and monitoring cancer in a patient; gene therapy; and the production of biologically active products. Additional examples include uses in preparation of bio-artificial liver devices and liver assist devices.

The cells of this invention as used herein refer to any of the staring cells to which one or more of the above-mentioned heterologous transcription factors have been introduced, as well as progenies of the cells such as the iHep cells and progeny thereof. Progenies as used herein includes cells derived from a parent, starting, or founder cell via cell division or cell fusion with other cell(s).

Treatment of Liver Diseases

In an aspect, the invention provides methods for treating liver diseases or conditions. Also, the invention provides uses for the manufacture of a medicament for treating such liver diseases or conditions using the iHep cells disclosed herein (including iHep cells from humans and non-human animals) or the progeny thereof.

Such diseases may include disorders affecting liver tissue, and conditions affecting the hepatocyte viability and/or function (e.g., birth defects, the effect of a disease condition, the effect of trauma, toxic effects, viral infections, etc). Examples of the liver diseases or conditions include genetic liver diseases (e.g., Alagille syndrome), carbo-hydrate metabolism disorders (e.g., glycogen storage disease and galactosemia, fructosemia), amino acid metabolism disorders (e.g., tyrosinemia), glycolipid and lipid metabolism disorders (e.g., Niemann-Pick disease, Hunter's disease, Hurler's disease, and Wolman's disease), glycoprotein metabolism disorders (e.g., Gaucher's disease), metal storage disorders (e.g., Hemochromatosis and Wilson's Disease), peroxisomal disorders (e.g., Zellweger syndrome and mitochondrial cytopathies); hereditary disorders of bilirubin metabolism (e.g., Crigler-Najjar syndrome, Gilbert syndrome, and Dubin-Johnson syndrome), hereditary disorders of bile formation (e.g., progressive familial intrahepatic cholestasis), bile acid biosynthesis disorders, protein biosynthesis and targeting disorders ($\alpha_1$-Antitrypsin deficiency and cystic fibrosis), acute liver failure arising from a combination of genetic and environmental factors.

The treatment methods include administering to the subject identified as in need of such treatment an effective amount of a cell composition described herein, or a composition described herein to produce such a cell composition. Identifying a subject in need of such treatment can be in the judgment of a subject or a health care professional and can be subjective (e.g., opinion) or objective (e.g., measurable by a test or diagnostic method). Determination of those subjects "at risk" can also be made by any objective or subjective determination by a diagnostic test or opinion of a subject or health care provider (e.g., genetic test, enzyme or protein marker, family history, and the like). The compositions described herein may be also used in the treatment of any other disorders in which a reduction in liver function may be implicated.

The number of cells needed to restore liver function, fully or partially, varies depending on the degree of liver damage and the size, age and weight of the host. For example, the cells are administered in an amount effective to restore liver functions. Determination of effective amounts is well within the capability of those skilled in the art. The effective dose can be determined by using a variety of different assays designed to detect restoration of liver function. The progress of the transplant of the recipient can be determined using assays that include blood tests known as liver function tests. Such liver function tests include assays for alkaline phosphatase, alanine transaminase, aspartate transaminase and bilirubin. In addition, recipients can be examined for the presence or disappearance of features normally associated with liver disease such as, for example, jaundice, anemia, leukopenia, thrombocytopenia, increased heart rate, and high levels of insulin. Further, imaging tests such as ultrasound, computer assisted tomography (CAT) and magnetic resonance (MR) may be used to assay for liver function.

The iHep cells can be administered by conventional techniques such as injection of cells into the recipient host liver, injection into a site of liver lesion or at a site from which such cells can migrate to the site of the lesion (e.g., administration to spleen, portal vein, liver pulp, etc., e.g., by injection), or surgical transplantation of cells into the recipient host liver. See, e.g., Dhawan et al., (2010), Nature reviews Gastroenterology & hepatology 7, 288-298. In some instances it can be necessary to administer the iHep cells more than once to restore liver function. In addition, growth factors, such as G-CSF, or hormones, and TGFβ1 can be administered to the recipient prior to and following transplantation for the purpose of priming the recipient's liver and blood to accept the transplanted cells and/or to generate an environment supportive of hepatic cell proliferation.

"Treating" or "treatment" refers to administration of a compound or agent to a subject who has a disorder with the purpose to cure, alleviate, relieve, remedy, delay the onset of, prevent, or ameliorate the disorder, the symptom of the disorder, the disease state secondary to the disorder, or the predisposition toward the disorder. The terms "prevent," "preventing," "prevention," "prophylactic treatment" and the like refer to reducing the probability of developing a disorder or condition in a subject, who does not have, but is at risk of or susceptible to developing a disorder or condition.

A "subject" refers to a human and a non-human animal. In one embodiment, the subject is a human. In another, the subject is an experimental, non-human animal or animal suitable as a disease model. The term "animal" includes all vertebrate animals including humans. It also includes an individual animal in all stages of development, including embryonic and fetal stages. In particular, the term "vertebrate animal" includes, but not limited to, humans, non-human primates (particularly higher primates), canines (e.g., dogs), felines (e.g., cats); equines (e.g., horses), bovines (e.g., cattle), porcine (e.g., pigs), rodent (e.g., mouse or rat), guinea pig, cat, rabbit, as well as in avians, such as birds, amphibians, reptiles, etc. The term "avian" refers to any species or subspecies of the taxonomic class ava, such as, but not limited to, chickens (breeders, broilers and layers), turkeys, ducks, a goose, a quail, pheasants, parrots, finches, hawks, crows and ratites including ostrich, emu and cassowary. Examples of a non-human animal include all non-human vertebrates, e.g., non-human mammals and non-mammals mentioned above.

When using the cells, methods, compositions and device in treating a subject (e.g., a patient of liver failure), subject or patient-derived hiHep cells represent a new type of functional hepatocytes that could be used in personalized regenerative medicine and disease modeling. This is an advantage unmatchable by HepG2 or other hepatic cell lines. Previous studies have successfully generated hepatocyte-like cells from human induced pluripotent stem cells (iPSCs, Ji et al., (2012), J Cell Biochem.) derivations of hepatocyte-like cells from iPSCs or direct lineage conversion represent two valuable approaches to obtain surrogate hepatocytes for disease modeling and therapeutic applications.

The results in the examples below showed that hiHep cells resemble PHH markedly in terms of gene expression, hepatic functions and therapeutic effects; therefore, hiHep cells have potential uses as surrogate hepatocytes in pharmaceutical research and cellular therapies. For example, biliary excretion is a key function of mature hepatocytes for the detoxification of non-degradable xenobiotics (Pan et al., (2012), J Pharm Sci 101, 1898-1908.). Because hiHep cells possess significant biliary excretion functions, it is possible to apply these cells to evaluate biliary excretion of candidate drugs.

It is remarkable that the repopulation of hiHep cells rescued around 30% of Fah-deficient mice. Previous studies showed that transplantation of primary mouse hepatocytes usually leads to a survival rate close to 100%, whereas a survival rate of 30%-50% is commonly observed after transplantation of human primary hepatocytes (He et al. (2010), Am J Pathol 177, 1311-1319.). Interestingly, the serum albumin level in hiHep-transplanted mice was only 1/20-1/30 of that in PHH-transplanted mice when normalized to the repopulation efficiency. Therefore, it is plausible that there may be therapeutic effects of hiHep cells or primary hepatocytes other than secretion of albumin.

Bio-Artificial Liver

One skilled in the art can use hiHep to obtain better therapeutic effect, to generate humanized animal models, or make devices to support patients who have liver disorders or failure. For example, because encapsulated hiHep cells showed the capability to treat acute liver failure mice, one can use the cells as source cells for extracorporeal or implantable bio-artificial liver supporting devices. See e.g., Strain (2002) Science 295 (5557): 1005-9; Carpentier et al., (2009), Gut 58, 1690-1702, Palakkan et al., (2013), Liver international: official journal of the International Association for the Study of the Liver 33, 666-676).

Bio-artificial livers can be used in aiding patients with liver failure, several variations of bio-artificial livers are known in the art. Yet, a common type of this device includes a plasma separator, recirculation reservoir, a pump, charcoal cylinder filter, oxygenator/heater and a bioreactor. The plasma separator isolates the plasma and cellular components of the blood. The cellular components remain in a storage device to later be reunited with the plasma. The plasma then gets fed through a charcoal cylinder that filters plasma bacteria and matter that the hepatic cells cannot handle. The plasma then gets fed through a cell-containing bioreactor device. During this process the plasma and hepatocytes are constantly being kept at body temperature and oxygenated. The newly cleaned plasma is then reunited with the cellular component and fed back into the patient. The bioreactors used in a bio-artificial liver device can vary. The current bioreactor devices are either; hollow fiber, flat plate and monolayer, perfused beds/scaffolds, encapsulation and suspension. See, e.g., US Pat. No. 8,486,699 and US Application Nos. 20130344154, 20130095077, 20120111795, 20120009086, 20110195056, 20110125286, 20090311765, 20090291064, and 20050148073.

The main challenge in developing either an extracorporeal artificial liver device or implantable artificial livers are the procumbent and maintenance of hepatic cells, as well as patient safety. For obvious reasons, it is logistically difficult to obtain a large number of human hepatocytes due to constraints in time, money and resources. Hepatocytes from non-human animal such as pigs can be used instead. However, this alternative is controversial due to possible transmission of viral infections to humans. In addition, the materials used in the bioreactors and the filtration processes have shown mixed results in the fostering of hepatocytes. Much care has to be taken to obtain hepatocytes and maintain their survival when they come in contact with the plasma because they are not only put through tremendous stress but do not fare well in low concentrations of oxygen levels. The hiHep cells disclosed herein provide a much need source for bio-artificial liver devices, either extracorporeal devices or implanted devices.

In one example, the bioreactor in the bio-artificial liver device includes a reservoir chamber that contains iHep cells, a pump assembly, and inlet and outlet in fluid communication with the chamber. The chamber is adapted for receiving a supply of blood from a blood supply assembly. The blood supply assembly may include a supply of blood provided for infusion to a patient or to another particular desired location. The supply of blood may be received from a bag or other blood container (e.g., plasma separator, recirculation reservoir, a pump, charcoal cylinder filter, oxygenator/heater and); from a blood transferring device, such as a heart bypass system, blood oxygenator, blood filtration assembly, artificial heart and the like; from another individual; or from the patient.

The blood supply assembly provides the blood to the reservoir chamber via the inlet. The reservoir chamber has iHep cells housed therein for providing a liver function, such as detoxification. The reservoir chamber and cells therein process the received blood. The processed blood is then provided to a delivery assembly for delivery via the outlet to a desired location of the patient.

The device and method described above can be used to treat or support patients with liver disorder or failure. Factors influencing the determination of blood flow characteristics for the extracorporeal circuit may include one or more of the many clinical parameters or variables of the blood to be supplied to the patient, e.g., the size of the patient, the percentage of overall circulation to be provided, the size of the target to be accessed, hemolysis, hemodilution, $pO_2$, pulsatility, mass flow rate, volume flow rate, temperature, hemoglobin concentration and pH. The device may be used in conjunction with angiographic or guiding catheters, arterial sheaths, and/or other devices used in angioplasty and in other interventional cardiovascular procedures. The system may be used in applications involving one or more vascular openings, i.e., in either contralateral or ipsilateral procedures.

Tissue-Engineering

The invention also provides a tissue-engineered organ, or portion, or specific section thereof, as well as a tissue engineered device having the iHep cells of this invention or progenies thereof. A tissue engineered liver can provide a new therapy in which differentiated iHep cells are transplanted within three-dimensional polymer scaffolds to supplement or replace the function of a failing liver. Tissue-engineered organs can be used with a biocompatible scaffold to support cell growth in a three-dimensional configuration, which can be biodegradable.

The construction of a three-dimensional polymer-cell scaffold made of polymer and hepatocyte-like cell can be carried out according to WO/2003/076564 and U.S. Pat. Nos. 5,624,840 and 5,759,830. A tissue engineered liver can be made of iHep cells fabricated onto a matrix or a scaffold made of natural or manmade material. For example, the cells can be used to seed a decellularized liver scaffold as described in U.S. Patent Application 20050249816. Manmade materials that can be used are often biodegradable polymers, such as the three-dimensional tissue culture system in which cells were laid over a polymer support system (See U.S. Pat. No. 5,863,531). Materials suitable for polymer scaffold fabrication include, alginate-poly-L-lysine-alginate (APA), polylactic acid (PLA), poly-L-lactic acid (PLLA), poly-D-lactic acid (PDLA), polyglycolide, polyglycolic acid (PGA), polylactide-co-glycolide (PLGA), polydioxanone, polygluconate, polylactic acid-polyethylene oxide copolymers, modified cellulose, collagen, polyhydroxybutyrate, polyhydroxpriopionic acid, polyphosphoester, poly (alpha-hydroxy acid), polycaprolactone, polycarbonates, polyamides, polyanhydrides, polyamino acids, polyorthoesters, polyacetals, polycyanoacrylates, degradable urethanes, aliphatic polyesterspolyacrylates, polymethacrylate, acyl substituted cellulose acetates, non-degradable polyurethanes, polystyrenes, polyvinyl chloride, polyvinyl flouride, polyvinyl imidazole, chlorosulphonated polyolifms, polyethylene oxide, polyvinyl alcohol, Teflon™, nylon silicon, and shape memory materials, such as poly (styrene-block-butadiene), polynorbornene, hydrogels, metallic alloys, and oligo (s-caprolactone) diol as switching segment/oligo (p-dioxyanone) diol as physical crosslink. Other suitable polymers can be obtained by reference to The Polymer Handbook, 3rd edition (Wiley, N.Y., 1989). Such tissue engineered liver can be implanted into the patient to restore liver function.

This invention also provides use of the hepatocyte-like cells of the invention as part of a bioreactor, e.g., a liver assist device. Further, the iHep cells of this invention or their progenies can be used as biological components of detoxification devices such as liver perfusion or liver assist devices. Specifically, the cells of this invention can be used to construct extracorporeal liver assist device such as a bio-artificial liver for use by subjects having liver disorders that result in hepatic failure or insufficiency. The use of such bio-artificial livers involves the perfusion of the subject's blood through the bio-artificial liver. In the blood perfusion protocol, the subject's blood is withdrawn and passed into contact with the iHep cell cultures. During such passage, molecules dissolved in the patient's blood, such as bilirubin, are taken up and metabolized by the hepatocyte cultures. In addition, the hepatocyte-like cells provide factors normally supplied by liver tissue.

An exemplary liver assist device includes a rigid, plastic outer shell and hollow semi-permeable membrane fibers which are seeded with iHep cells of this invention or their progenies. The fibers can be coated with collagen, lectin, laminin, or fibronectin, for the attachment of cells. Body fluid from a subject can perfuse through the device for detoxification according to procedures known in the art and then returned to the subject.

Drug Testing and Screening

The iHep cells of this invention or their progenies can also be used as a tool for drug testing and development process. For example, one can use the cells to assess changes in gene expression patterns caused by drugs being considered for development. The changes in gene expression pattern from potential drugs can be compared with those caused by control drugs known to affect the liver. This allows one to screen compounds for their effects on the liver earlier in the development process without using animals, thereby saving time and money. In some embodiments, the iHep cells of this invention or their progenies are used in a high throughput drug screening, such as in the manner described in U.S. Pat. No. 7,282,366.

The iHep cells of this invention or their progenies can also be used to assess toxicity of various compounds or compositions of interest, e.g., chemical, pharmaceutical, cosmetic, biocidal or biological compounds, food additives or compositions, or biological agents. The use of differentiated cells may be preferred in such assays of toxicity, as the cells more closely resemble the cell types present in the liver of an organism. For example, a particular compound or composition is considered toxic or likely toxic, if it shows a detrimental effect on the viability of cells or on one or more aspects of cellular metabolism or function. The viability of cells in vitro may be measured using techniques known in the art, including colorimetric assays, such as the MTT (or MTT derivative) assays or LDH leakage assays, or using fluorescence-based assays, such as, e.g., the Live/Dead assay, CyQuant cell proliferation assay, or assays of apoptosis. Other useful assays include those that measure particular aspects of cellular metabolism or function. See, e.g., Azuma, et al., (2007), Nat Biotechnol 25, 903-910; Gomez-Lechon et al., (2004), Current drug metabolism 5, 443-462; and Lazaro, et al. (2007), Am J Pathol 170, 478-489

Carcinogenicity Evaluation

It is known in the art that various compounds cause tumors in experimental animals such as mice even though they fail to act as mutagens in test organisms such as bacteria or fungi. One of the reasons for this phenomenon is metabolic activation; i.e., some chemicals are metabolically altered by enzymes in the liver (the P450 oxidase system and hydroxylation systems) or other tissues, creating new compounds that are both mutagenic and carcinogenic. In order to identify such carcinogens, people have used screening assays involving incubating a test chemical compound with liver extracts or liver tissues prior to exposure of the test organism to the metabolic product (Ames et al., 1975, Mut. Res. 31:347-364; U.S. Pat. No. 7,026,137). The iHep cells of this invention or their progenies can be used as a substitute for the liver extracts or liver tissues described in the conventional assays.

Thus, the present invention also provides methods and assays to evaluate the carcinogenicity of a test compound or agent using the cells of this invention, which closely resemble the cell types present in the liver of an organism. These cells can be used in assays of both genotoxic and non-genotoxic (i.e., epigenetic) carcinogenicity. For example, one can contact the cells with a test agent and then examine neoplastic transformation or genetic stability of the cells. The agent is considered carcinogenic or likely carcinogenic, if it induces neoplastic transformation of the cells, or induces phenotypic changes in the cells that may be predictive of such neoplastic transformation, or induces genetic or metabolic changes that may potentially cause such neoplastic transformation.

Examples of phenotypic changes in the cells include, but are not limited to, morphological transformation, increased proliferation, dedifferentiation, independence of attachment, removal of contact inhibition of cells grown in monolayers, or expression of specific marker proteins. Such genetic changes in the cells may comprise, but are not limited to, DNA damage, chromosomal aberrations, e.g., chromosomal rearrangements, alterations in chromosome number (aneuploidy), or karyotype aberrations, gene mutations, e.g., point mutations, deletions or insertions. Agents that cause this kind of genetic changes are often referred to as mutagenic or mutagens. Accordingly, the cells provided by the present invention will be very useful in assays of mutagens, i.e., in assays of mutagenicity.

For the purposes of mutagenicity testing, the cells of the present invention can be genetically altered. For example, the cells may contain a transgene, encoding a polypeptide that increases the cells' sensitivity to a particular proliferation-inhibiting agent. Consequently, genetic alterations in some cells by removing the expression of such transgene would release these cells from this inhibition. Mutagenicity may then be assessed by methods of scoring such cells.

Other Uses

The cells of this invention can be further used for various other uses. For example, they can be used in producing one or more proteins expressed in the liver.

One example is blood coagulation factors, which are useful for subjects with hemophilia and other blood clotting disorders. Currently, most of the preparations of blood coagulation factors are from donated blood, presenting disadvantage and danger of transmitting hepatitis. Producing blood coagulation factors in vitro from the hepatocyte-like cell described herein greatly reduces the risk of transmitting hepatitis or other blood borne diseases. To produce coagulation factors, one can culture the cells of this invention under suitable conditions. After the cultured hepatocyte-like cells have reached confluency, the supernatant culture media can be collected and purified according to methods known in the art, such as those described in U.S. Pat. No. 4,789,733 and Kane et al. J. Biol. Chem., 256:1002-1007, 1981.

Primary hepatocytes have versatile characteristics and functions. To use iHep cells for fully recapitulating primary hepatocytes, one can improve iHep cells in vitro for specialized purposes. For example, iHep cells as disclosed herein express several Cyp genes and acquire Cyp1a, Cyp3a and Cyp2c activities. By further optimization of iHep cells to express drug transporter genes and enhanced Cyp activities, one can obtain an alternative to primary hepatocytes for the early stages of drug discovery. Interestingly, preliminary data by the inventors implicate that mouse ESC-derived hepatocyte-like cells appeared to be more immature compared with iHep cells as disclosed herein. Nonetheless, a comprehensive comparison of iHep cells with other surrogate hepatocyte-like cells would be necessary, so that when a specialized hepatic function is desired one can decide which hepatocyte-like cells to choose.

Compositions

In a further aspect, the invention relates to a pharmaceutical composition comprising the human iHep cells, or iHep cells from other species including man, obtainable or directly obtained using the herein described methods, or a cell population comprising such as defined above, or the progeny thereof.

The term "pharmaceutical composition" refers to the combination of an active agent (e.g., cells or transcription factors disclosed herein) with a carrier, inert or active, making the composition especially suitable for diagnostic or therapeutic use in vivo or ex vivo. A "pharmaceutically acceptable carrier," after administered to or upon a subject, does not cause undesirable physiological effects. The carrier in the pharmaceutical composition must be "acceptable" also in the sense that it is compatible with the active ingredient and can be capable of stabilizing it (e.g., keeping iHep cells alive). One or more solubilizing agents can be utilized as pharmaceutical carriers for delivery of an active agent. Examples of a pharmaceutically acceptable carrier include, but are not limited to, biocompatible vehicles, adjuvants, additives, and diluents to achieve a composition usable as a dosage form. Examples of other carriers include colloidal silicon oxide, magnesium stearate, cellulose, and sodium lauryl sulfate. Additional suitable pharmaceutical carriers and diluents, as well as pharmaceutical necessities for their use, are described in Remington's Pharmaceutical Sciences.

Kits

The invention encompasses kits and systems for preparing iHep cells. To that end, one or more of the above-described factors, nucleic acids, (e.g., expression vectors, dsRNAs), or other agents/components for the methods disclosed herein can be supplied in the form of a kit. In such a kit, an appropriate amount of one or more components is provided in one or more containers.

A kit containing reagents for performing the methods may include one or more of the followings: a first agent selected from a first group consisting of a HNF polypeptide and a nucleic acid encoding said HNF polypeptide; and a second agent selected from a second group consisting of FOXA polypeptide and a nucleic acid encoding said FOXA polypeptide. The HNF polypeptide can be HNF4A, HNF1A, or HNF1B. The FOXA polypeptide can be FOXA1, FOXA2, or FOXA3. The kit can further include an additional agent selected from a group consisting of an additional polypeptide, a nucleic acid encoding the additional polypeptide, and a compound (e.g., siRNA or related dsRNA) that reduces the expression of an Rb family gene. The additional polypeptide can be selected from the group consisting of SV40 large T antigen, C/EBPβ, GATA4, HHEX, KLF4, and PROX1.

The kit may also contain additional materials for cell culturing, nucleic acid transfection, virus infection, and protein transduction. The kit may include regents for detecting a liver marker or function.

The kit components may be provided in a variety of forms. For example, the components (e.g., polypeptides and nucleic acids) can be suspended in an aqueous solution or as a freeze-dried or lyophilized powder, pellet, or bead. In the latter case, the components, when reconstituted, form a complete mixture of components for use.

A kit or system may contain, in an amount sufficient for at least one assay, any combination of the components described herein, and may further include instructions recorded in a tangible form for use of the components. In some applications, one or more kit components may be provided in pre-measured single use amounts in individual, typically disposable, tubes or equivalent containers. The amount of a component supplied in the kit can be any appropriate amount, and may depend on the target market to which the product is directed. General guidelines for cell culturing, nucleic acid transfection, virus infection, and protein transduction may be found in, for example, Joseph Sambrook and David W. Russell, Molecular Cloning: A Laboratory Manual, 3rd edition, Cold Spring Harbor Laboratory Press, 2001; and Frederick M. Ausubel, Current Protocols in Molecular Biology, John Wiley & Sons, 2003.

The kits of the invention can comprise any number of additional reagents or substances that are useful for practicing the invention. Such substances include, but are not limited to: reagents (including buffers) for processing cells, divalent cation chelating agents or other agents that inhibit unwanted nucleases, and control cells for use in ensuring that the kit components are functioning properly. The kits can be provided at any temperature. For example, for storage of kits containing protein components or complexes thereof in a liquid, it is preferred that they are provided and maintained below 0° C., preferably at or below −20° C., or otherwise in a frozen state.

The container(s) in which the components are supplied can be any conventional container that is capable of holding the supplied form, for instance, microfuge tubes, ampoules, bottles, or integral testing devices, such as fluidic devices, cartridges, lateral flow, or other similar devices. The kits can include either labeled or unlabeled nucleic acid probes, antibodies for use in detection of relevant targets. In some embodiments, the kits can further include instructions to use the components in any of the methods described herein. Typical packaging materials for such kits and systems include solid matrices (e.g., glass, plastic, paper, foil, microparticles and the like) that hold the kit components in any of a variety of configurations (e.g., in a vial, microtiter plate well, microarray, and the like).

As disclosed herein, a number of ranges of values are provided. It is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention.

The term "about" generally refers to plus or minus 10% of the indicated number. For example, "about 20" may indicate a range of 18 to 22, and "about 1" may mean from 0.9-1.1. Other meanings of "about" may be apparent from the context, such as rounding off, so, for example "about 1" may also mean from 0.5 to 1.4.

As used herein, the term "contacting" and its variants, when used in reference to any set of components, includes any process whereby the components to be contacted are mixed into same mixture (for example, are added into the same compartment or solution), and does not necessarily require actual physical contact between the recited components. The recited components can be contacted in any order or any combination (or subcombination), and can include situations where one or some of the recited components are subsequently removed from the mixture, optionally prior to addition of other recited components. For example, "contacting A with B and C" includes any and all of the following situations: (i) A is mixed with C, then B is added to the mixture; (ii) A and B are mixed into a mixture; B is removed from the mixture, and then C is added to the mixture; and (iii) A is added to a mixture of B and C. "Contacting a template with a reaction mixture" includes any or all of the following situations: (i) the template is contacted with a first component of the reaction mixture to create a mixture; then other components of the reaction mixture are added in any order or combination to the mixture; and (ii) the reaction mixture is fully formed prior to mixture with the template.

EXAMPLE 1

Materials and Methods

This example describes materials and methods used in EXAMPLES 2-8 below unless specifically noted otherwise.

Molecular Cloning And Lentivirus Production

Modified pWPI plasmids carrying candidate genes were introduced into 293FT cells together with packaging plasmid psPAX2 (Addgene) and envelop plasmid pMD2.G (Addgene) to produce viruses.

cDNAs of candidate genes and SV40 large T were cloned into modified pWPI plasmid. pWPI was obtained from Addgene and modified as described in previous publication. For shRNA expression, DNA oligonucleotides encoding human p53 shRNA (GACTCCAGTGGTAATCTAC, SEQ ID NO: 14), human RB1 shRNA (CAGAGATCGTGTATTGAGATT, SEQ ID NO: 15), human p21 shRNA (CGCTCTACATCTTCTGCCTTA, SEQ ID NO: 16) were inserted into pLKO.1 plasmid. Constructed plasmids were then introduced into 293FT cells together with packaging plasmid psPAX2 (Addgene) and envelop plasmid pMD2.G (Addgene). After 48 hours incubation, the medium containing lentiviruses was collected and passed through 0.45 µm filter.

Medium

Hepatocyte maintenance medium (HMM) is DMEM/F12 (Hyclone) supplemented with 0.544 mg/L $ZnCl_2$ (Sinopharm), 0.75 mg/L $ZnSO_4 \cdot 7H_2O$ (Sinopharm), 0.2 mg/L $CuSO_4 \cdot 5H2O$ (Sinopharm), 0.025 mg/L $MnSO_4$ (Sinopharm), 2 g/L Bovine serum albumin (Sigma-Aldrich), 2 g/L Galactose (Sigma-Aldrich), 0.1 g/L Ornithine, 0.03 g/L Proline, 0.61 g/L Nicotinamide, 1× Insulin-transferrin-sodium selenite media supplement (Sigma-Aldrich), 40 ng/ml TGFα (Peprotech), 40 ng/ml EGF (Peprotech), 10 µM dexamethasone and 1% fetal bovine serum (Sigma-Aldrich). hiHep CYP450 Induction Medium (HIM) consist of 75% IMDM (Hyclone), 25% Ham's F12 (Hyclone), 0.5×N2 supplement, 0.5×B27 supplement without retinoic acid, 0.1% Bovine serum albumin, 50 µg/ml ascorbic acid, 0.45 mM Monothioglycerol, 10 ng/ml bFGF, 40 ng/ml EGF (Peprotech), 40 ng/ml TGFα (Peprotech), 100 µM dibutyryl cyclic AMP (Sigma-Aldrich), 10 µM dexamethasone, 6 µg/ml Vitamin K1 (Sigma-Aldrich), 20 ng/ml Oncostatin M (Peprotech), 1% Fetal bovine serum, 1×MEM Non-Essential Amino Acids Solution (Gibco). Human Fibroblast Medium (HFM) is DMEM/F12 (Hyclone) supplemented with 10% Fetal bovine serum, 0.1 mM β-mercaptoethanol (Sigma-Aldrich), 1×MEM Non-Essential Amino Acids Solution (Gibco), and 4 ng/ml bFGF (Peprotech).

Cell Culture

Primary human hepatocytes were maintained at 37° C., 5% CO2 in HMM before used for experiments. Cryopreserved human hepatocytes from two individuals were provided by Celsius In Vitro Technologies (Baltimore, Md.) and from one individual by Invitrogen Gibco (Carlsbad, Calif.). Frozen hepatocytes have been shown to be useful for various hepatic functional assays, including xenobiotic metabolism and cytotoxicity evaluation (Hengstler et al., 2000, Drug Metabolism Reviews 32, 81-118; Li, 2007, Chemico-Biological Interactions 168, 16-29; Li et al., 1999, Chemico-Biological Interactions 121, 117-123.). During experiments, these cells gave comparable results with published primary human hepatocytes in terms of CYP activities (Hewitt et al., 2007, Drug Metabolism Reviews 39, 159-234; Monostory et al., 2005, FEBS letters 579, 229-235; Roymans et al, 2004, Biochemical Pharmacology 67, 427-437), biliary excretion (Hartman et al., (2010) Canadian Journal Of Physiology And Pharmacology 88, 682-691; Marion et al, 2012, Toxicology and Applied Pharmacology 261, 1-9), and Albumin secretion (Takebe et al., 2013, Nature 499, 481-484).

Human fetal fibroblasts (HFF) and human adult fibroblasts (HAF) were cultured in at 37° C., 5% CO2 in HFM. Two HFFs (HFF1 and HFF2) were derived from limbs of human fetuses collected by the International Peace Maternity and Child Health Hospital. HAF was produced from human skin biopsy collected at Shanghai Renji Hospital. Tissues around 1 $mm^3$ were placed on dishes and maintained in culture for 2 weeks. Fibroblasts that migrated out of tissue pieces were reseeded and expanded for experiments. The Ethical Committees of the International Peace Maternity and Child Health Hospital and of Shanghai Renji Hospital approved collection and use of human samples. Informed consent was obtained from all subjects.

For bile duct differentiation in 3-dimensional cultures, $1 \times 10^4$ cells were re-suspended in 400 µl 5×DMEM/F12 medium with 1.6 mL 1 mg/ml freshly prepared neutralized collagen gel solution and poured into a 35-mm dish. After gel solidification, cells were cultured with 1.5 mL DMEM/F12 supplemented with 10% FBS, 1×ITS, 20 ng/mL HGF. Biliary branching ducts were documented at day 3.

hiHep Induction and Cell Culture

Human fibroblasts were seeded on a collagen I coated dish and infected with lentiviruses carrying indicated genes. HFF and HAF were cultured in human fibroblast medium (HFM). HFF1 and HFF2 were derived from limbs of human foetuses. HAF was derived from human skin biopsy. Primary human hepatocytes were purchased from Invitrogen Gibco (Carlsbad, Calif.) or Celsis In Vitro Technologies (Baltimore, Md.). Institutional ethical committees approved collection and use of human samples.

In some cases, HFF and HAF between passage 5 and 9 were used for hiHep production. To generate hiHep cells, $1.75-2 \times 10^5$ human fibroblasts were seeded on a collagen I coated 6 cm dish. One day later, the cells were infected with indicated viruses (each MOI=1) supplemented with 4 µg/ml polybrene for 24 hours, and then changed to HFM for another 24 hours. The media were then changed to HMM. Compared to induction of mouse iHep cells, the original human fibroblasts should be maintained in HFM with doubling time around 24 hours for HFF or between 48 and 60 hours for HAF. Only early passages of human fibroblasts should be used. Before lentivirus infection, human fibroblasts should be re-plated in a density of $1.75 \times 10^5$ to $2 \times 10^5$ cells per 6 cm dish, which is the double of the density for mouse iHep induction. Culture medium should be changed to fresh HFM 24 hours after infection, and then to HMM 48 hours after infection. Low cell density or prolonged incubation of lentiviruses with human fibroblasts dramatically reduced the efficiency of hepatic conversion (Table 4).

PCR

For most experiments, total RNA was isolated from cells by Trizol (Invitrogen). For PHH, mRNA was extracted from PHH cultured for 24 hours after plating. 1 µg RNA was reverse transcribed into cDNA with M-MLV Reverse Transcriptase (Promega) according to manufacturer's instructions. PCR was performed with HiFi Taq polymerase (TransGen). Quantitative real-time PCR was performed with SYBR Premix Ex Taq (TaKaRa) on ABI StepOnePlus real-time PCR system (Applied Biosystems). All q-PCR data were performed with at least 2 repeats. The PCR products were confirm by proper melting curves and an agarose-gel electrophoresis. Primer sequences are provided in Table 2 below.

TABLE 2

| Gene | Forward(5'-3') | SEQ ID NO | Reverse(5'-3') | SEQ ID NO |
|---|---|---|---|---|
| ALB | GCCTTTGCTCAGTATCTT | 17 | AGGTTTGGGTTGTCATCT | 18 |
| AAT | TATGATGAAGCGTTTAGGC | 19 | CAGTAATGGACAGTTTGGGT | 20 |
| CK8 | CAGAAGTCCTACAAGGTGTCCA | 21 | CTCTGGTTGACCGTAACTGCG | 22 |
| CK18 | TCGCAAATACTGTGGACAATGC | 23 | GCAGTCGTGTGATATTGGTGT | 24 |
| TTR | TGGGAGCCATTTGCCTCTG | 25 | AGCCGTGGTGGAATAGGAGTA | 26 |
| ASGPR1 | ATGACCAAGGAGTATCAAGACCT | 27 | TGAAGTTGCTGAACGTCTCTCT | 28 |
| MRP2 | AGCGTCCTCTGACACTCG | 29 | GGCATCTTGGCTTTGACT | 30 |
| TAT | GCATCCTATGTCGCACCC | 31 | TCAGCAACTAACCGCTCC | 32 |
| Transferrin | TGTCTACATAGCGGGCAAGT | 33 | GTTCCAGCCAGCGGTTCT | 34 |
| HNF1B | CTGGCACCTCAGACAATCCACTC | 35 | CAGTACGGCTTTCTTGCTTCCTC | 36 |
| COL1A2 | GGCCCTCAAGGTTTCCAAGG | 37 | CACCCTGTGGTCCAACAACTC | 38 |
| SNAI1 | TCGGAAGCCTAACTACAGCGA | 39 | AGATGAGCATTGGCAGCGAG | 40 |
| TWIST2 | GCTACAGCAAGAAGTCGAGCGAAGA | 41 | TTGTCAGAGGGCAGCGTGGG | 42 |
| MMP14 | CGAGGTGCCCTATGCCTAC | 43 | CTCGGCAGAGTCAAAGTGG | 44 |
| FGF7 | TCCTGCCAACTTTGCTCTACA | 45 | CAGGGCTGGAACAGTTCACAT | 46 |
| WISP2 | GCGACCAACTCCACGTCTG | 47 | TCCCCTTCCCGATACAGGC | 48 |
| GJB1 | ATGCTCCGACAGCGTCTC | 49 | TGCCCTCTGCTCCTCTTAC | 50 |
| CYP1A2 | CTTCGCTACCTGCCTAACCC | 51 | GACTGTGTCAAATCCTGCTCC | 52 |
| CYP2A6 | CAGCACTTCCTGAATGAG | 53 | AGGTGACTGGGAGGACTTGAGGC | 54 |
| CYP2B6 | GCACTCCTCACAGGACTCTTG | 55 | CCCAGGTGTACCGTGAAGAC | 56 |
| CYP2C9 | CTACAGATAGGTATTAAGGACA | 57 | GCTTCATATCCATGCAGCACCAC | 58 |
| CYP2D6 | TGAAGGATGAGGCCGTCTGGGAGA | 59 | CAGTGGGCACCGAGAAGCTGAAGT | 60 |
| CYP3A4 | TTCAGCAAGAAGAACAAGGACAA | 61 | GGTTGAAGAAGTCCTCCTAAGC | 62 |
| CYP2C8 | CATTACTGACTTCCGTGCTACAT | 63 | CTCCTGCACAAATTCGTTTTCC | 64 |
| AHR | CAAATCCTTCCAAGCGGCATA | 65 | CGCTGAGCCTAAGAACTGAAAG | 66 |
| CAR | GTGCTCCTGTGCGGAGTAG | 67 | ATGGCAGATAGGCAGTTTCCC | 68 |
| PXR | AAGCCCAGTGTCAACGCAG | 69 | GGGTCTTCCGGGTGATCTC | 70 |
| FXR | AACCATACTCGCAATACAGCAA | 71 | ACAGCTCATCCCCTTTGATCC | 72 |
| RXRA | ATGGACACCAAACATTTCCTGC | 73 | GGGAGCTGATGACCGAGAAAG | 74 |
| RXRB | GCAGCCCAAATGACCCTGT | 75 | CCCGCAGCAATATGACCTGA | 76 |
| RXRG | AGAGGACGATAAGGAAGGACC | 77 | CCATGACAAGGCACTTCTGAT | 78 |
| SHP | CCCCAAGGAATATGCCTGCC | 79 | TAGGGCGAAAGAAGAGGTCCC | 80 |
| GR | ATAGCTCTGTTCCAGACTCAACT | 81 | TCCTGAAACCTGGTATTGCCT | 82 |
| LXRA | ACACCTCATGCGTCGCAAG | 83 | GACGAGCTTCTCGATCATGCC | 84 |
| MDR1 | ATGAAGTTGAATTAGAAAATGCAG | 85 | GGAAACTGGAGGTATACTTTCATC | 86 |
| MRP2 | AGCAGCCATAGAGCTGGCCTT | 87 | AGCAAAACCAGGAGCCATGTCC | 88 |
| MRP3 | GATCAGGTTTATCTCCAACCCCA | 89 | GATCCCAGTACGAAACTTCACC | 90 |
| BSEP | AAGAAAGGTGATGGCGTTAGAG | 91 | CTTGTAACTCAACGTCGTAGTCA | 92 |

TABLE 2 -continued

Primers

| Gene | Forward(5'-3') | SEQ ID NO | Reverse(5'-3') | SEQ ID NO |
|---|---|---|---|---|
| NTCP | AAGGACAAGGTGCCCTATAAAGG | 93 | ACGATCCCTATGGTGCAAGGA | 94 |
| OATP1 | TCCTTGGTTACCCTCGGCA | 95 | AGAGGCAGGTCTCTGATGGTT | 96 |
| OATP2 | TTGGAGGTGTTTTGACTGCTT | 97 | ACAAGTGGATAAGGTCGATGTTG | 98 |
| OATPB | TATGTGGACATTAACCAGATGCC | 99 | CTGTGACTGCTAAGACCTTTCG | 100 |
| APOB | CAGCTGATTGAGGTGTCCAG | 101 | CACTGGAGGATGTGAGTGGA | 102 |
| ITIH2 | ACCAGGTCTCCACTCCATTG | 103 | ATCCTGCAAGTCGTCCATCT | 104 |
| human ALU | AATATGGCCCAACTGCAGAA | 105 | CATCGCATTTTCACATCCAA | 106 |
| FAH | CCTACGGCGTCTTCTCGAC | 107 | CTGCAAGAACACTCTCGCCT | 108 |
| AFP | ACTGAATCCAGAACACTGCA | 109 | TGCAGTCAATGCATCTTTCA | 110 |
| endo HNF1 | ACCAGGACAAGCATGGTCCCACAT | 111 | TCCACCGCATTTCTCCTTGACTTTA | 112 |
| endo FOXA3 | TAACATCTGGGTGGGTCT | 113 | CAGTGGATTAGCCAATAACA | 114 |
| endo HNF4A | CAACCCAACCTCATCCTC | 115 | GTCCCATCTCACCTGCTC | 116 |
| exo HNF1A | GCCACCTGCTGCCATCCAA | 117 | TGCAGCCCGTAGTTTAAAC | 118 |
| exo FOXA3 | GCCCTACAACTTCAACCACC | 119 | TGCAGCCCGTAGTTTAAAC | 120 |
| exo HNF4A | CCGTCGCCACAATCGTCA | 121 | TGCAGCCCGTAGTTTAAAC | 122 |
| GAPDH | CCACCTTTGACGCTGGG | 123 | CATACCAGGAAATGAGCTTGACA | 124 |
| LIN28B | AGGCCTTGAGTCAATACGGG | 125 | TCTTTGGCTGAGGAGGTAGAC | 126 |
| IGF2 | CTTCTCACCTTCTTGGCCTTCG | 127 | TGCGGAAACAGCACTCCTCAAC | 128 |
| DLK1 | AGAACGACGGCGTCTGCA | 129 | GACCTGTGAACTCGGGCTTG | 130 |
| EPCAM | AGGAGATGGGTGAGATGC | 131 | GATTGGTAAAGCCAGTTTC | 132 |
| LGR5 | TCCACTTTGCCATCCCTAA | 133 | GGTCGTCCATACTGCTGTTG | 134 |
| CFTR | TGAAACTGACTCGGAAGG | 135 | CAGAATGAGATGGTGGTG | 136 |
| AQP1 | TAACCCTGCTCGGTCCTTTG | 137 | CCACCCTGGAGTTGATGTCG | 138 |
| GGT | CGTAGAGGCTTTCCGGTTTG | 139 | TAGTAGGAGATCGGGTGAGTGG | 140 |
| CCNA2 | CGCTGGCGGTACTGAAGTC | 141 | GAGGAACGGTGACATGCTCAT | 142 |
| CCNB1 | AATAAGGCGAAGATCAACATGGC | 143 | TTTGTTACCAATGTCCCCAAGAG | 144 |
| CCNB2 | TGCTCTGCAAAATCGAGGACA | 145 | GCCAATCCACTAGGATGGCA | 146 |
| CK19 | TCCGAACCAAGTTTGAGACG | 147 | CCCTCAGCGTACTGATTTCCT | 148 |
| HHEX | TCCAACGACCAGACCATC | 149 | AGTCTCCTCCATTTAGCG | 150 |
| HNF6 | CAACGTGAGCGGTAGCTTCA | 151 | GCATCTTGTCGGTGGGCAT | 152 |
| TBX3 | GAGGCTAAAGAACTTTGGGATCA | 153 | CATTTCGGGGTCGGCCTTA | 154 |
| SOX17 | ATTTCCTCGGTGGTGTCC | 155 | CCAAACTGTTCAAGTGGCAGA | 156 |
| SOX9 | GACTACACCGACCACCAGAACTCC | 157 | GTCTGCGGGATGGAAGGGA | 158 |
| ALB-pro | TTGTGAGGCTTAGGAATGAA | 159 | AAGGACCTGAGTGGTAGGAA | 160 |
| AAT-pro | TTGAGGCCAGGAGTTTGAGA | 161 | GGCATTACAGGCATGTGCTAC | 162 |

Human Albumin and α-1-Antitrypsin ELISA

To determine the secretion of human Albumin and α-1-Antitrypsin, supernatants of cell culture were collected after 48 hours culture. PHH were seeded on 12-well plates for 12 hours, and then maintained in HMM for 48 hours until collection of supernatants. For transplantation experiments, animal serum was collected. Levels of human Albumin and α-1 Antitrypsin were measured by the human Albumin ELISA Quantitation Set (Bethyl Laboratory) and the human α-1-Antitrypsin ELISA kit (Bethyl Laboratory) according to the manufacturer's instructions. Serum was diluted in a range from 10- to 10000-fold to obtain values falling to the linear range of standard curve.

Immuno-Fluorescent Staining and Flow Cytometry Analysis

For immunofluorescent staining, the cells were fixed with 4% paraformaldehyde for 15 min at room temperature, and then incubated with PBS containing 0.2% TRITON X-100 (Sigma) for 15 min. Cells were then washed three times with PBS. After being blocked by 3% BSA in PBS for 60 min at room temperature, cells were incubated with primary antibodies at 4° C. overnight, washed three times with PBS, and then incubated with appropriate fluorescence-conjugated secondary antibody for 60 min at room temperature in dark. Nuclei were stained with DAPI (Sigma). Primary and secondary antibodies were diluted in PBS containing 3% BSA.

Antibodies used for immunofluorescent staining are as follows: goat anti-human-Albumin (Bethyl Laboratories, 1:100), goat anti-mouse-Albumin (Bethyl Laboratories, 1:200), rabbit anti-FAH (AbboMax, San Jose, Calif., 1:1500), rabbit anti-human-α-1-antitrypsin (NeoMarkers, 1:200), mouse anti-human-ZO1 (Invitrogen, 1:500), Cy3-conjugated donkey anti-goat IgG (Jackson Lab, 1:1000), FITC-conjugated donkey anti-rabbit IgG (Jackson Lab, 1:1000), Cy5-conjugated donkey anti-rabbit (Jackson Lab, 1:500), Cy5-conjugated donkey anti-mouse (Jackson Lab, 1:1000).

For flow cytometry analyses, cells were harvested and washed twice in HBSS solution (Sigma-Aldrich) with 0.1% BSA, and then incubated with antibodies diluted in HBSS solution with 0.1% BSA at 4° C. in dark for 30 min. For flow cytometry analyses of ALB and AAT, cells were permeabilized by 0.3% TRITON X-100 for 15 min and incubated with ALB and AAT antibodies for 2 hours at room temperature after fixation. Cells were then incubated with the secondary antibodies for 1 hour in dark at room temperature. After incubation, the cells were washed twice and analyzed by the Calibur Flow Cytometer (Becton Dickinson). For selection of CD133-EpCAM-HFF, the cells were sorted out by BD FACS Aria II (Becton Dickinson). Antibodies used for FACS are as follows: EpCAM-FITC (Miltenyi Biotec, 1:11), CD133-PE (Miltenyi Biotec, 1:11), Mouse anti-Albumin (R&D, 2.5 μg/106 cells), Rabbit anti-AAT (NeoMarkers, 1:200). Data were analyzed with Flow Jo software (Tree Star).

Microarray Analysis

Total RNAs were hybridized to whole human gene expression microarray (Agilent) under the manufacturer's instruction. Data were normalized using Gene-Spring (Agilent). Original data are available in Gene Expression Omnibus database (GSE42643).

More specifically, total RNAs extracted from two HFFs, HepG2, three primary human hepatocytes cultured for 1, 2 and 6 days, hiHep cells from three independent experiments, hiHep$^{LT}$ cells at passage 10 from 3 independent experiments were hybridized to whole human gene expression microarray (Agilent) under the manufacturer's instruction. Data were normalized using Gene-Spring (Agilent). Microarray hybridization and analysis were carried out by ShanghaiBio Cooperation (Shanghai, China). To enrich genes with altered expressions, genes with significant expression level changes were sorted by setting 2.5-fold change in primary human hepatocytes, hiHep cells or hiHep$^{LT}$ cells. In total 6,324 genes were left for further analysis. Clustering of expression data from these genes was performed by Cluster 3.0 software (Stanford University) using Euclidean distance as similarity metric algorithm and average linkage as clustering methods. Clustered heat-maps were produced by TreeView. Original data were uploaded to Gene Expression Omnibus database (GEO) with accession number: GSE42643.

Gene Set Enrichment Analysis (GSEA) was performed with GSEA v2.0.1.2 to identify the pathways that were significantly enriched in PHH and hiHep versus HFF. All probe sets were used for analysis. Gene sets were compiled from BIOCARTA, Kyoto Encyclopedia of Genes and Genomes (KEGG) and REACTOME pathway databases. For Venn diagram, genes were grouped according to BIOCARTA, KEGG and REACTOME. Genes with expression levels >2-fold increase in hiHep cells and PHH were counted as up-regulated genes. Up-regulated hepatic genes in hiHep cells and PHH were then plotted into a Venn diagram.

ChIP Assay

HFF and hiHep cells were cross-linked using 1% formaldehyde. Lysates were then sonicated to yield DNA fragments around 500-1000 bp. DNA was co-immunoprecipitated using H3K9Ac ChIP grade antibodies (Abcam) or control IgG at 4° C. overnight. The ALB and AAT promoters were amplified and quantified by q-PCR using SYBR Green (Takara) on ABI 7500 Fastsystem. The comparative cycle threshold method was used to quantify the amplified fragments and results from each immunoprecipitation were normalized to its respective inputs. Primer sequences are provided in Table 2.

Assays for PAS, ac-LDL, ICG and Oil Red O Staining

Cells were stained by Periodic-Acid-Schiff (PAS, Sigma) and DiI-ac-LDL (Invitrogen) following manufacturer's instructions. For indocyanine green (ICG, Sigma) uptake assay, cells were changed medium with 1 mg/ml ICG and incubated at 37° C. for 1 hour, followed by washing with PBS three times. For Oil red O staining, confluent cells were cultured in HMM. After 4 days, cells were washed twice with PBS (Hyclone), fixed in 4% formalin for 30 min, washed by PBS, followed by Oil Red O (Sigma-Aldrich) staining for 10 min, and then washed twice by 70% ethanol and stained with hematoxylin (Sigma-Aldrich) for 5 min.

CYP Induction And Metabolism Assay

For the measurement of CYP enzyme activities, cells were induced with different compounds for certain drug metabolisms. The supernatants were collected for measurement of metabolized compounds by LC-MS/MS (Agilent 1200 HPLC and ABI 4000 mass-spectrometer).

More specifically, for the measurement of CYP enzyme induction, hiHep, hiHepLT, HFF and PHH cells were cultured in HIM for 48 hours and then change to HIM supplemented with 3-methylcholanthrene (25 μM), rifampicin (25 μM) and sodium phenobarbital (2 mM) for additional 48 hours. Total RNA was extracted to measure the induction of CYP enzymes responding to chemical inducers by q-PCR. Total RNA of cells without inducer treatment were used to measure the expression of CYP450 genes and nuclear receptor genes.

For measurement of CYP metabolism activities, hiHep, hiHep$^{LT}$, and HFF cells were cultured in HIM for 48 hours and then change to HIM supplemented with 25 μM 3-methylcholanthrene (for phenacetin metabolism assay), 25 µM rifampicin (for Coumarin metabolism assay) and 2 mM sodium phenobarbital (for Dextromethorphan metabolism assay) for 48 hours. Freshly thawed primary human hepatocytes were directly used as a positive control. Cells were incubated with substrate in 200 µl incubation medium at different concentrations for 3 hours at 37° C. To stop the reaction, 800 ml cold methanol was added and centrifuged. The supernatants were collected for measurement of metabolized compounds by LC-MS/MS (Agilent 1200 HPLC and ABI 4000 mass-spectrometer). Total cell protein amount was used to normalize the data. Substrates and metabolized products used for standard curves were commercially purchased.

Sandwich Culture And Biliary Excretion Assay

To prepare sandwich culture, $1 \times 10^5$ hiHep cells, primary human hepatocytes, and HFF were seeded in collagen I coated 24 well plate. 200 µL 1.5 mg/ml freshly prepared neutralized collagen gel solution were then poured on cells. After solidification, cells were cultured in Williams' E medium supplemented with 5% FBS, 10 µM TCA and 2 µM cAMP for a further 4 days.

To analyze the biliary excretion index, cells were washed once and then incubate in HBSS buffer or Calcium free HBSS buffer at 37° C. Ten minutes after incubation, buffers were aspirated and cells were incubated with test compound solution (DPDPE 5 µM; CLF 2.5µM; D8-TCA 5 µM, diluted in HBSS buffer) for 10 minutes. Cumulative uptake was stopped by washing with cold HBSS buffer for three times. DPDPE and D8-TCA were analysed by LC/MS/MS (LCMS-8030; Shimadzu, Kyoto, Japan). The amount of CLF was quantified by measuring fluorescence at 492 nm and 536 nm with a Synergy 4 microplate reader (Biotek, Winooski, USA). Biliary Excretion Index (BEI) was calculated as: $BEI=(A_{HBSS}-A_{HBSS}(Ca3+free))/A_{HBSS} \times 100\%$.

Mice

Fah−/− Rag2−/− (F/R) mice were maintained with drinking water containing 7.5 mg/L of NTBC. The genetic background for Fah−/− Rag2−/− mice was C57B16/J× 129Sv. C57B16/J mice were purchased from the Model Animal Research Center of Nanjing University (Nanjing, Jiangsu, China). F/R mice were maintained in specific pathogen free husbandry. All animal experiments were performed according to institutional regulations.

Transplantation of hiHep$^{LT}$ Cells into Fah-Deficient Mice hiHep$^{LT}$ cells were intrasplenically transplanted into F/R mice after the withdrawn of NTBC water. Body weight was monitored twice a week post transplantation. Survived recipient mice were sacrificed to collect blood and liver samples 9 weeks after transplantation.

More specifically, six days before hiHep$^{LT}$ cell transplantation, concentration of NTBC in drinking water for F/R mice was first reduced to 3.75 mg/L for 3 days and was then totally withdrawn for another 3 days, $1 \times 10^7$ hiHep$^{LT}$ cells in 200 µL PBS were intrasplenically transplanted into F/R mice. Fresh PHH were used for the experiment. To deplete nature killer cells in recipient mice, anti-mouse asialo-GM1 (40 µg in 200 µL saline per mouse) was intraperitoneally injected into F/R mice one day before transplantation and then at 7-day intervals after transplantation. Furthermore, recipient mice were administrated with FK506 (Astellas) at the dose of 1 µg per gram body weight per day after transplantation. Body weight was monitored twice a week post transplantation. Survived recipient mice were sacrificed to collect blood and liver samples 8-10 weeks after transplantation. Blood and liver samples of control Fah−/− Rag2−/− mice were collected when 30% body weight was lost after NTBC withdrawal.

Microencapsulated Cells

HFFs, HepG2, PHH and hiHep$^{LT}$ cells were packaged in APA microcapsules by the static electricity drip technique. Briefly, proliferating cells were harvested and suspended in saline containing 1.5% (w/v) filter-sterilized sodium alginate solution (Sigma) with final cell density of $1.5 \times 10^7$ cells/mL (for HFF, HepG2 and hiHep$^{LT}$) or $0.5 \times 10^7$ (for PHH). Fresh PHH were used for the experiment. The cell suspension was extruded through a 0.4-mm needle into 100 mM CaCl2 solution using an electrostatic droplet generator to form calcium alginate gel beads. After washing, the gel beads were incubated with 0.05% (w/v) poly-l-lysine (PLL) (molecular weight 21,900, Sigma) to form alginate-poly-l-lysine membrane around the surface. After washing the beads in saline, a further coating of alginate was applied by suspending them in 0.15% (w/v) alginate for 5 min. The membrane-enclosed gel beads were further suspended in 55 mM sodium citrate to liquefy the alginate gel core. As a result, APA microcapsules with a diameter around 350 µm were formed which allows penetration of compounds with molecular weight smaller than 100 kD. The microcapsules with HFFs, hepG2, PHH and hiHep$^{LT}$ cells were kept in HMM before transplantation.

hiHep$^{LT}$ Cell Transplantation to Concanavalin A-Induced Acute Liver Failure Mice C57B16/J mice were injected with Concanavalin A (Con A, Sigma-Aldrich) at the dose of 37.5 mg per kg body weight through tail vein. Con A treatment triggers strong hepatitis in a few hours which leads to acute liver failure and death within 24 hours in almost all mice. 8 hours after Con A treatment, $1.5 \times 10^7$ encapsulated HFFs or hiHep$^{LT}$ cells or $0.5 \times 10^7$ PHH were injected intraperitoneally into acute liver failure mice. Mice were monitored every 3 hours in the first day after Con A treatment and 3 times a day for the rest one week. Blood samples were collected from survived mice in a 24-hour-interval. Liver samples were collected after the survived animals were sacrificed. All animal experiments were performed according to institutional animal regulations.

Histology and Immunohistochemistry

Tissues were fixed overnight with 4% neutral formalin. Tissue sections were stained with haematoxylin and eosin for pathological evaluation. For immunohistochemical staining, paraffin sections (3-4 µm thick) were used. Slides were treated in 3% $H_2O_2$ for 15 min, locked in 5% normal goat or horse serum in 1% BSA-PBS for 20 min, and stained with the indicated antibodies in 1% BSA-PBS overnight. Secondary antibodies were used according to Vectastain ABC kits (Vector Laboratories), followed by DAB staining (DAKO). Following antibodies were used for immunohistochemical staining: rabbit anti-FAH (AbboMax, San Jose, Calif., 1:3000), rabbit anti-human AAT (NeoMarkers, 1:100).

For RNA extraction from formalin-fixed-paraffin-embedded (FFPE) tissues, eight serial sections mounted on polyethylene terephthalate (PET) membrane frame slides (Leica) were deparaffinized and air-dried. The first section was stained with anti-Fah antibody to identify the repopulated Fah+ nodules. Based on the Fah immunostaining results, Fah+ tissues within the nodules were microdissected from the following seven sections by a MMI CellCut Plus (Molecular Machines & Industries) with appropriate laser intensity and speed. After microdissection, the remaining sections on the slides were further stained with anti-Fah antibody to confirm that only tissues inside Fah+ nodules were separated. Microdissected tissues from the same Fah+ nodule were pooled together for total RNA extraction using RNeasy FFPE Kit (Qiagen).

Statistics

All data are presented as mean±s.d. For most statistic evaluation, one-sided unpaired Student's t test was applied for calculating statistical probability in this study. For survival analysis, one-sided Mantel-Cox log-rank test was applied. Statistic calculation was performed using Statistical Program for Social Sciences software (SPSS, IBM). For all statistics, data from at least 3 independent samples or repeated experiments were used.

No specific statistic calculation was performed to estimate sample size. Sample sizes were chosen mainly based on the previous experience. Details of samples sizes could be found in figure legends. No samples or animals were excluded from analysis. All animals were grouped into experimental or control groups randomly. The investigators were not totally blinded to the group allocation in the study. Different investigators verified the data.

EXAMPLE 2

Generation of hiHep Cells by Direct Lineage Conversion

Mouse fibroblasts have been converted into induced hepatocyte-like (iHep) cells. In this example, study was carried out to induce functionally mature human iHep cells.

Figure 8:
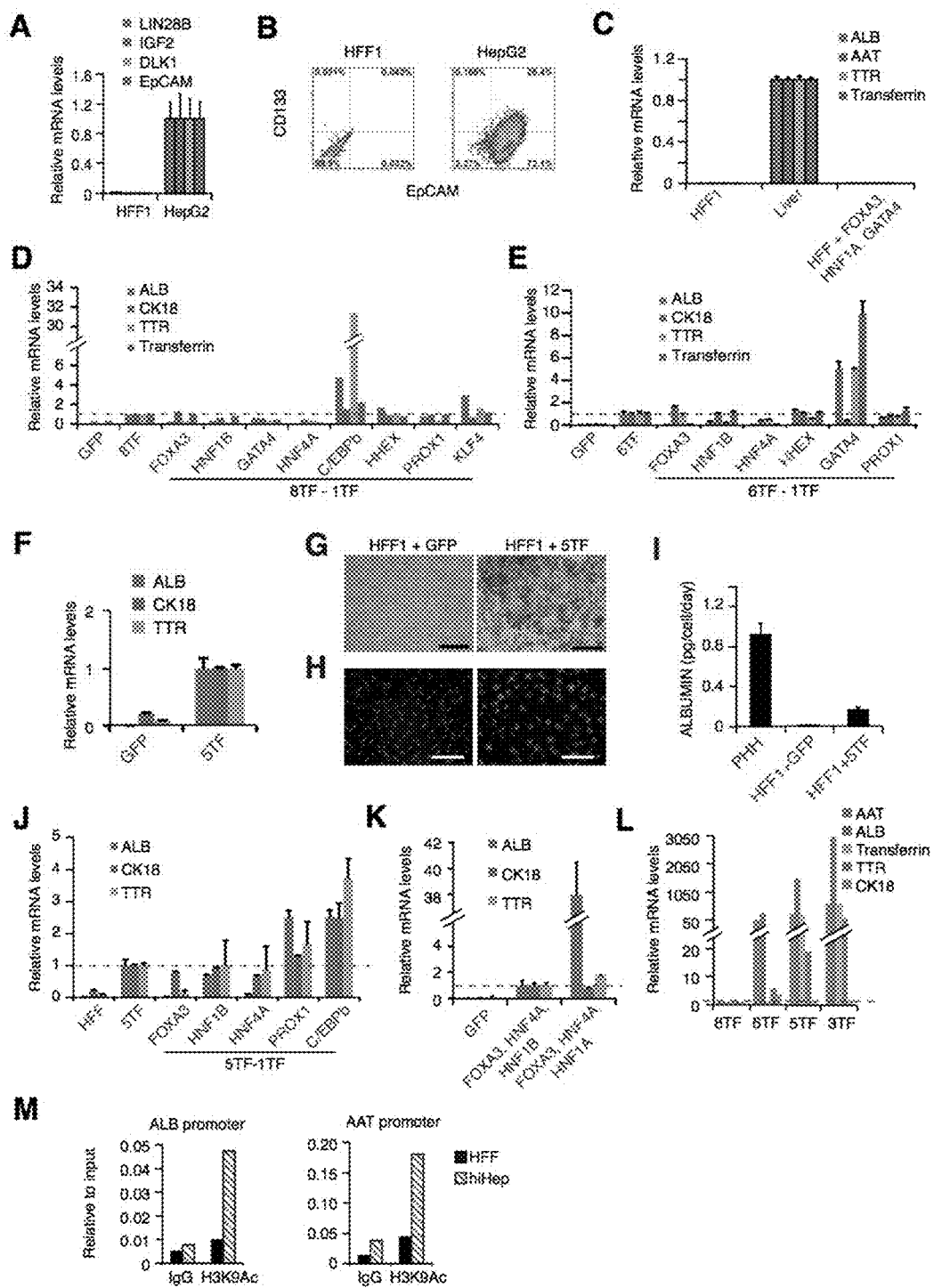
FIGS. 8A-8M are a set of diagrams and photographs showing identification of factors for human hiHep cell induction: (A) and (B) Expression of marker genes for hepatoblasts. (C) Human FOXA3, HNF1A and GATA4 were expressed in HFF1 via lentiviral infection. (D and E) Effects of individual factor withdrawal from 8 transcription factors (8TF, D) and 6 transcription factors (6TF, E) on hepatic gene expression. (F-I) A combination of FOXA3, HNF1B, HNF4A, PROX1 and C/EBPβ (collectively referred to as 5TF) induced hepatic conversion in HFF1. 5TF triggered hepatic gene expression (F), glycogen storage (G, shown as PAS staining), acetylated LDL intake (H, red fluorescence) and ALB secretion (I). Scale bars: 100 μm. Data are normalized to 5TF. (J) FOXA3, HNF1B and HNF4A were important for hepatic conversion. (K) Replacement of HNF1B with HNF1A in combination with FOXA3 and HNF4A significantly enhanced ALB expression in HFF1. (L) 8TF, 6TF, 5TF and 3TF-induced hepatic gene expression were determined by q-PCR. (M) hiHep cells show increased H3K9Ac levels at the ALB and AAT promoters.

First primary human foetal limb fibroblasts (HFF1) were generated and it was demonstrated that HFF1 cells were free of foetal hepatoblasts (FIGS. 8A and B). Briefly, expression of marker genes for hepatoblasts was determined in HFF1 by q-PCR. Data were normalized to HepG2 (FIG. 8A). It was found that HFF1 were negative for CD133 and EpCAM as shown by flow cytometry, whereas the human hepatoblastoma cell line HepG2 was EpCAM positive and partially CD133 positive (FIG. 8B).

Based on findings in mouse cells (Huang et al., (2011) Nature 475, 386-389), lentiviruses carrying human FOXA3, HNF1A and GATA4 were introduced into HFF1 cells. However, the expression of hepatic genes was not induced as measured by quantitative PCR (q-PCR) (FIG. 8C), suggesting that a different protocol is required for hepatic conversion in human cells. The expression levels of hepatic genes such as ALB, AAT, transthyretin (TTR) and transferrin were undetectable 8 days after transduction as determined by q-PCR. Data were normalized to the liver.

A de novo screen was therefore designed for factors critical for hiHep induction. Shown in FIG. 1A is the experimental design for the induction of hiHep cells. Briefly, primary human fibroblasts were infected with lentiviruses expressing human hepatic transcription factors (Table 1). The culture medium was changed to HMM medium 2 days after infection to generate hiHep cells. The hiHep cells were characterised 10-14 days after induction.

Initially, 8 human transcription factors ("8TF," FIG. 1A and Table 1) were selected, including pioneer factors FOXA3 and GATA4, liver enriched transcription factors HNF1B, HNF4A, HHEX, PROX1, C/EBPβ, and KLF4, a transcription factor important for mesenchymal-to-epithelial transition in reprogramming. It was found that the mRNA levels of hepatocyte-specific genes, such as Albumin (ALB), Cytokeratin 18 (CK18), Transthyretin (TTR) and Transferrin, were markedly induced in HFF1 after the expression of 8TF (FIG. 8D). The expression levels of the indicated hepatic genes were analyzed by q-PCR in HFF1 12 days after transduction with 8TF (FIG. 8D) or 6TF (FIG. 8E). Data were normalized to 8TF or 6TF.

Upon removing one or more single factors from 8TF, it was found that KLF4, HHEX and GATA4 were not required for hepatic gene expression. It was also found that FOXA3, HNF1B and HNF4A were important for hepatic conversion (FIGS. 8E-J). To that end, the effects of individual factor withdrawal from 5TF on hepatic gene expression were analyzed by q-PCR. Based on the expression levels of ALB, CK18 and TTR, it was found that FOXA3, HNF1B and HNF4A were important for hepatic conversion. Data were normalized to 5TF (FIG. 8J).

Interestingly, replacement of HNF1B with HNF1A dramatically enhanced ALB expression (FIG. 8K, data normalized to FOXA3, HNF4A and HNF1B group). Removing individual factors from FOXA3, HNF1A and HNF4A (collectively referred to as "3TF") reduced the expression of hepatic genes (FIG. 1B), as measured by quantitative PCR (q-PCR). Data were normalized to 3TF.

Notably, 3TF induced higher levels of hepatic gene expression than other combinations of transcription factors (FIG. 8L, data normalized to 8TF.). 3TF also triggered increased H3K9 acetylation at the promoter region of ALB and AAT genes, suggesting an epigenetic remodelling during hepatic conversion (FIG. 8M). To that end, H3K9Ac levels were measured by chromatin immunoprecipitation (ChIP) assay. Based on these 3 factors, hiHep induction was improved by optimising the culture conditions for fibroblasts, fibroblast seeding density, virus infection and hepatocyte culture medium.

hiHep cells induced with 3TF displayed an epithelial morphology at 12 days after induction (FIG. 1C). The expression of genes specific for mature hepatocytes, e.g., ALB, ASGPR1 and Transferrin, increased gradually during hiHep induction, suggesting that hepatic conversion is a progressively coordinated process (FIG. 1D). The expression levels of the indicated genes were analysed by q-PCR. Data are normalized to HFF+3TF at Day 4. By contrast, the expression of fibroblast-specific genes was dramatically reduced in hiHep cells (FIG. 1E). As shown in FIG. 1E, genes specific to the original fibroblasts were silenced in hiHep cells at 2 weeks after induction. In the above assays, all data were normalized to HFF1. PHH cultured for 2 days were used as controls in FIGS. 1D and E. See also FIG. 8 and Tables 1 and 4.

EXAMPLE 3 hiHep Cells Possess Gene Expression Pattern and Functions Specific for Mature Hepatocytes In this example, assays were carried out to examine co-expression of the mature hepatic proteins ALB and AAT. In addition, ALB and AAT double positive cells, as quantified by flow cytometry, were used to determine the conversion efficiency of hiHep. PHH cultured for 2 days were used as positive controls.

Approximately 20% of cells expressed both ALB and AAT at day 12 as determined by immunofluorescent staining and flow cytometry (FIGS. 2A and 2B), suggesting an efficient conversion. Moreover, hiHep cells showed a remarkable capability for secreting the plasma proteins ALB and AAT at the level close to PHH as measured by enzyme-linked immunosorbent assay (ELISA) (FIGS. 2C and 2D).

Gene expression profile analysis was performed on HFFs, PHHs, unsorted hiHep cells and HepG2 cells by cDNA microarray. Hierarchical clustering showed that hiHep cells were grouped together with PHH. PHH were cultured for the number of days as indicated in FIG. 2E. PHH cultured at day 2 were grouped closely to PHH at day 6, suggesting that PHH maintain gene expression at a relatively stable level after cultured for 2 or more days. Human hepatoblastoma cell line HepG2 was included to reveal that the expression pattern of hiHep cells is closer to that of PHH as indicated by cluster tree on the top. Expression levels were depicted in colors.

Figure 2:
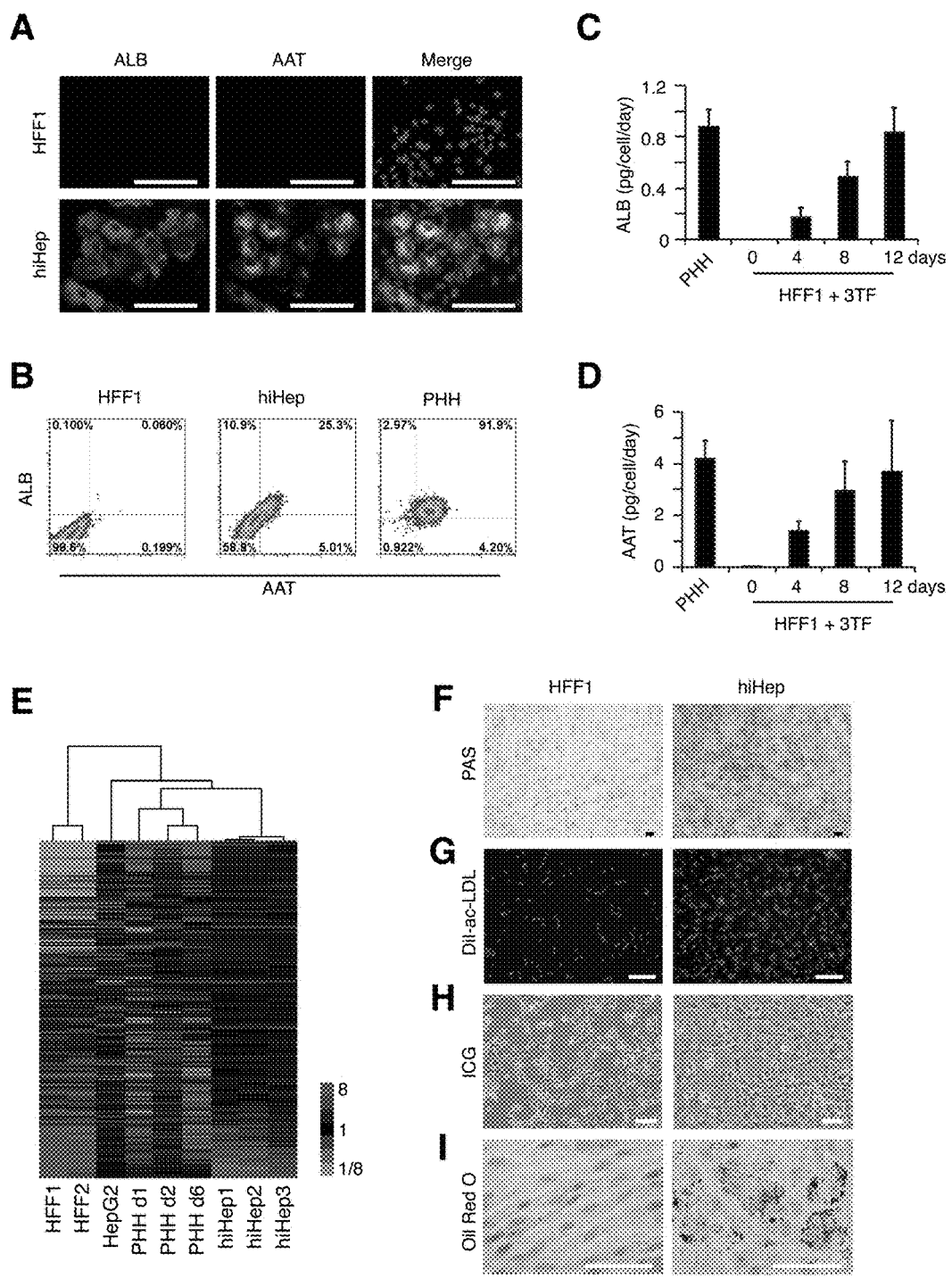
FIGS. 2A-2I are a set of diagrams and photographs showing that hiHep cells acquire hepatic gene expression pattern and mature functions: (A) Co-expression of the mature hepatic proteins albumin (ALB) and α-1-antitrypsin (AAT). (B) ALB and AAT double positive cells, as quantified by flow cytometry, were used to determine the conversion efficiency of hiHep. PHH cultured for 2 days were used as positive controls. (C, D) Excretion of ALB (C) and AAT (D) increased during hepatic conversion. (E) Gene expression profile analysis of HFFs, PHHs, unsorted hiHep cells and HepG2 cells by cDNA microarray. (F) Glycogen storage by hiHep cells was confirmed by periodic acid-Schiff (PAS) staining (magenta). (G) Intake of acetylated low density lipoprotein labeled with the fluorescent probe 1,1'-dioctadecyl-3,3,3',3'-tetramethyl-indocarbocyanine perchlorate (DiI-ac-LDL) in hiHep cells (red). (H) Indocyanine green (ICG) uptake in hiHep cells (green). (I) Lipid accumulation in hiHep cells as shown by Oil Red O staining. Scale bars: 100 µm. Data are represented as the mean±SD.

Genome-wide expression profile analysis revealed that hiHep cells were clustered closely with cultured PHH (FIG. 2E). Expression profiling also showed the fibrotic genes were efficiently silenced in hepatic conversion, which was in line with the published expression profiles of iPS cells (Sridharan et al., (2009), Cell 136, 364-377).

GSEA analysis revealed remarkably enriched hepatic gene expression in both PHH and hiHep cells. The analysis showed that pathways enriched in PHH were significantly enriched in hiHep cells, including those involved in lipid metabolism, amino acid metabolism, and phases I and II detoxification (Table 3). A peak shift to the left side indicates the enrichment of the indicated set of hepatic genes in PHH or hiHep cells. These data indicate that HFF undergo hepatic conversion by transcriptional alterations at the whole genome level.

More specifically, Table 3 below shows GSEA analysis of enriched pathways in PHH and hiHep cells. Top listed pathways are shown. The normalized enrichment score (NES) is the primary statistic for examining gene set enrichment results. NES can be used to compare analysis results across gene sets. The false discovery rate (FDR) is the estimated probability that a gene set with a given NES represents a false positive finding. In general, an FDR cutoff of 25% is appropriate.

In agreement with the systemic expression of hepatic genes, hiHep cells displayed numerous hallmark functions of mature hepatocytes, such as glycogen storage (FIG. 2F), acetylated low-density lipoprotein (ac-LDL) intake (FIG. 2G), indocyanine green (ICG) absorption (FIG. 2H) and cytoplasmic accumulation of neutral triglycerides and lipids (FIG. 2I).

Figure 9:
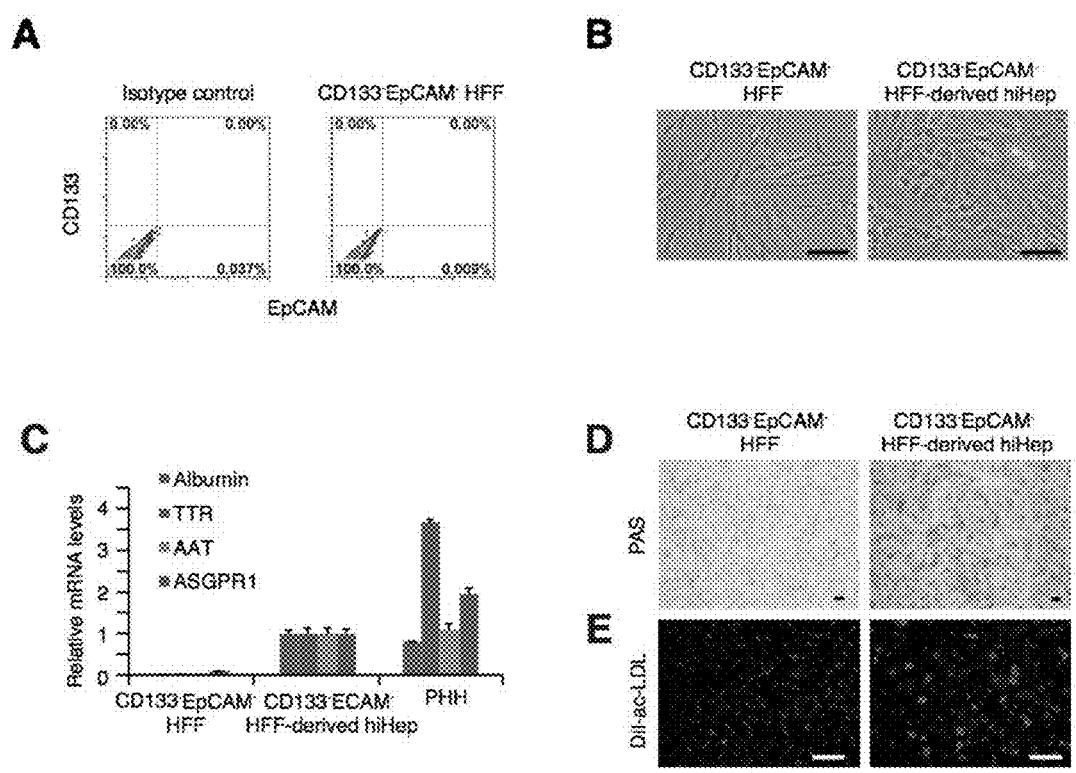
FIGS. 9A-9E are a set of diagrams and photographs showing that hiHep cells are not derived from hepatoblasts: (A) D133$^-$EpCAM$^-$ foetal fibroblast were sorted and confirmed by flow cytomtry. (B-E) CD133$^-$EpCAM$^-$ cells were converted to hihep cells by ectopic expression of 3TF. (B) hiHep cells derive from CD133$^-$EpCAM$^-$ HFF exhibited epithelial-like morphology. (C) Hepatic gene expression was induced by 3TF in C D133$^-$EpCAM$^-$ HFF cells as determined by q-PCR. Data are normalized to hiHep cells. (D,E) CD133$^-$EpCAM$^-$ HFF-derived hihep cells exhibited hepatic functions, including glycogen storage, as determined by PAS staining (D) and ac-LDL intake (E). Scale bars: 100 μm.

Hepatic lineage conversion induced by 3TF was confirmed in an additional HFF cell line, HFF2 (FIGS. 3A-D). For q-PCR, PHH cultured for 2 days were used as controls. Data were normalized to HFF2-hiHep. Furthermore, to exclude the possibility of hepatoblast contamination in foetal cell preparations, it was demonstrated that hiHep cells could be derived from CD133$^-$EpCAM$^-$ fibroblasts (FIG. 9).

Additionally, hepatic conversion from human adult dermal fibroblasts (HAF) was characterized. Morphologic change and hepatic gene expression were induced by 3TF in HAFs (FIGS. 3E and 3F). For q-PCR, PHH cultured for 2 days were used as controls. Data were normalized to HAF-hiHep. HAF-derived hiHep cells showed hepatic functions such as glycogen accumulation and ac-LDL intake (FIGS. 3H and 3H). Intriguingly, less than 10% of the cells were positive for both ALB and AAT (FIG. 3I), suggesting that hepatic conversion from HAF is less efficient than that from HFF.

TABLE 3

Hepatic pathways enriched in PHH and hiHep cells

| Enriched pathways | PHH | | hiHep | |
| --- | --- | --- | --- | --- |
| | NES | FDR q-Val | NES | FDR q-Val |
| Secretory serum protein | 2.848380 | 0.000000 | 2.897350 | 0.000000 |
| Biological oxidations | 2.593224 | 0.000000 | 2.528738 | 0.000000 |
| Retinol metabolism | 2.455535 | 0.000000 | 2.515632 | 0.000000 |
| Cytochrome P450 | 2.448759 | 0.000000 | 2.060806 | 0.001399 |
| Steroid hormone biosynthesis | 2.430169 | 0.000000 | 2.175039 | 0.000302 |
| Phase I functionalization of compounds | 2.398668 | 0.000000 | 2.184411 | 0.000169 |
| Complement and coagulation cascades | 2.393087 | 0.000000 | 2.195625 | 0.000185 |
| Drug metabolism by cytochrome P450 | 2.384630 | 0.000000 | 2.414431 | 0.000000 |
| Cytochrome P450 arranged by substrate type | 2.373544 | 0.000000 | 1.967677 | 0.003915 |
| Drug metabolism by other enzymes | 2.276418 | 0.000000 | 2.108813 | 0.000881 |
| Metabolism of amino acids and derivatives | 2.248954 | 0.000000 | 2.248841 | 0.000226 |
| Formation of fibrin clot clotting cascade | 2.211922 | 0.000000 | 2.156712 | 0.000426 |
| Peroxisome | 2.200612 | 0.000000 | 2.073016 | 0.001294 |
| Phase II conjugation | 2.169292 | 0.000000 | 2.341040 | 0.000000 |
| Complement cascade | 2.167240 | 0.000000 | 1.686066 | 0.044463 |
| Glycine serine and threonine metabolism | 2.152826 | 0.000000 | 2.067406 | 0.001419 |
| Bile acid and bile salt metabolism | 2.126958 | 0.000000 | 1.920084 | 0.006259 |
| HNF3B pathway | 2.059237 | 0.000000 | 2.155789 | 0.000397 |
| Intrinsic pathway (BIOCARTA) | 2.056696 | 0.000048 | 2.098023 | 0.000987 |
| Arginine and proline metabolism | 2.049210 | 0.000045 | 2.042419 | 0.001590 |
| Complement pathway | 2.045720 | 0.000083 | 1.506014 | 0.126983 |
| Porphyrin and chlorophyll metabolism | 2.035876 | 0.000080 | 1.943081 | 0.004898 |
| Tryptophan metabolism | 2.033409 | 0.000113 | 2.057264 | 0.001338 |
| Lipid digestion mobilization and transport | 2.022091 | 0.000299 | 2.259115 | 0.000254 |
| Lipoprotein metabolism | 2.020261 | 0.000287 | 2.314701 | 0.000000 |
| Intrinsic pathway (REACTOME) | 2.014540 | 0.000344 | 1.500063 | 0.129628 |
| Metabolism of lipids and lipoproteins | 1.983307 | 0.000664 | 1.994235 | 0.002857 |
| Tyrosine metabolism | 1.936312 | 0.001422 | 2.129963 | 0.000586 |
| Synthesis of bile acids and bile salts | 1.935945 | 0.001377 | 1.697827 | 0.040708 |
| Sulfur amino acid metabolism | 1.928390 | 0.001454 | 1.763359 | 0.026719 |
| Pentose and glucuronate interconversions | 1.907014 | 0.002129 | 1.799348 | 0.019970 |
| Gluconeogenesis | 1.900829 | 0.002369 | 1.848997 | 0.013204 |
| Histidine metabolism | 1.898671 | 0.002353 | 1.967833 | 0.004046 |
| Fatty acid metabolism | 1.876822 | 0.003338 | 2.043547 | 0.001616 |

TABLE 3-continued

Hepatic pathways enriched in PHH and hiHep cells

| Enriched pathways | PHH | | hiHep | |
|---|---|---|---|---|
| | NES | FDR q-Val | NES | FDR q-Val |
| Starch and sucrose metabolism | 1.870537 | 0.003611 | 1.682671 | 0.044046 |
| Ascorbate and aldarate metabolism | 1.864820 | 0.003911 | 1.716963 | 0.036611 |
| Ppar signaling pathway | 1.850054 | 0.004956 | 2.327915 | 0.000000 |

EXAMPLE 4

Detoxification and Biliary Excretion of hiHep Cells

Cytochrome P450 (CYP450) enzymes of hepatocytes are major enzymes accounting for drug detoxification. Their activities and responses to specific inducers are irreplaceably used to assess drug metabolism and drug-drug interaction in pharmacology. Intriguingly, phase I and phase II drug metabolic genes were enriched in both PHH and hiHep cells (Table 3).

Next, assays were carried out to analyze whether hiHep cells were responsive to CYP inducers. For the measurement of CYP enzyme expression and induction, hiHep and PHH cells were cultured for 48 hours and then changed to medium supplemented with or without chemical inducers for additional 48 hours.

Figure 4:
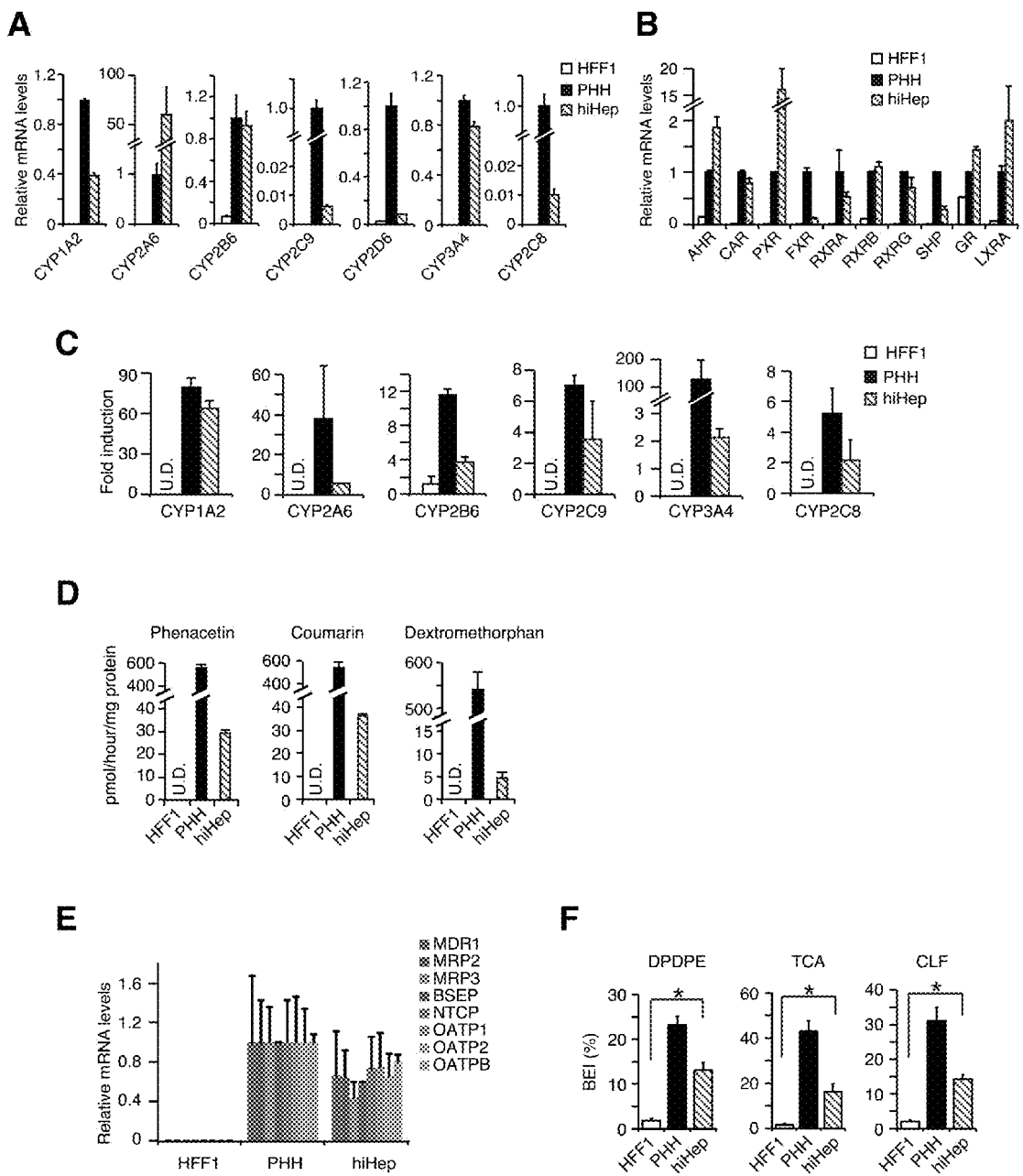
FIGS. 4A-4F are a set of diagrams showing that hiHep cells possess Cytochrome P450 (CYP) enzyme activities and biliary excretion capability. (A) The mRNA levels of CYP genes were determined by q-PCR in PHH and hiHep cells cultured for 2 days before inducer treatment. Data are normalized to PHH. (B) Expression levels of detoxification related nuclear receptors were measured by q-PCR in hiHep and PHH cells cultured for same duration as in (A). Data are normalized to PHH. (C) The mRNA levels of the induced CYP enzymes were measured by q-PCR. CYP1A2 was induced by 3-methylcholanthrene. CYP2A6, CYP2C8 and CYP2C9 were induced by rifampicin. CYP2B6 and CYP3A4 were induced by phenobarbital. Fold induction in hiHep and PHH cells were normalised to the levels in cells without inducer treatment, respectively. (D) CYP metabolic activity in hiHep cells. U.D.=undetectable. (E) Expression of drug transporter genes in hiHep cells as determined by q-PCR. Data are normalized to PHH. (F) hiHep cells showed the capability for biliary excretion as measured by clearance of [D-Pen2,5]-enkephalin hydrate (DPDPE), D8-taurocholic acid (D8-TCA) and cholyl-lysyl-fluorescein (CLF). Sandwich cultured PHH were used as positive controls. *: $P<0.05$, t-test. Data are represented as the mean±SD.

Before addition of chemical inducers, hiHep cells already expressed several CYP450 enzymes at remarkable levels (FIG. 4A). Transcriptional activation of CYP450 enzymes and many other drug metabolism enzymes are mediated by nuclear receptors including AHR, CAR, and PXR. These nuclear receptors were highly expressed in hiHep cells as determined by q-PCR (FIG. 4B). Furthermore, 3-methylcholanthrene, phenobarbital or rifampicin treatment markedly induced mRNA expression levels of CYP1A2 (an AHR target gene), CYP2A6 (a CAR target gene), CYP2B6, CYP2C8 and CYP2C9 (target genes of CAR and PXR). CYP3A4, which is a target gene of CAR and PXR, was induced at a relatively low but significant level by phenobarbital (FIG. 4C).

Importantly, in another assay for CYP activities, hiHep cells showed CYP enzyme-dependent metabolism of phenacetin, coumarin and dextromethorphan (FIG. 4D). To that end, CYP enzymes were induced in hiHep cells for 48 hours. Freshly thawed primary human hepatocytes were directly used as a positive control. The metabolic products of phenacetin (acetaminophen, assay for CYP1A2 activities), coumarin (7-hydroxycoumarin, assay for CYP2A activities) and dextromethorphan (dextrorphan, assay for CYP2D6 activities) were determined by liquid chromatography-tandem mass spectrometry.

Membrane transporter-mediated biliary excretion is another important function of hepatocytes for clearance of xenobiotics. Drug clearance through biliary excretion is a critically evaluated property in the selection of drug candidates. Significant efforts have been made to identify surrogate in vitro models to evaluate biliary excretion (Liu et al., (1999), Drug Metab Dispos 27, 637-644, and Pan et al., (2012), J Pharm Sci 101, 1898-1908). In this example, it was found that the expression levels of key transporter genes were significantly expressed in hiHep cells (FIG. 4E). Importantly, hiHep cells showed remarkable biliary excretion indices (BEI) for the clearance of multiple efflux transporter substrates, such as [D-Pen2,5]-enkephalin hydrate (DPDPE), D8-taurocholic acid (D8-TCA) and cholyl-lysyl-fluorescein (CLF) (FIG. 4F), suggesting a potential application for hiHep cells in the assessment of drug biliary clearance. Together, our data indicate that hiHep cells possess remarkable mature hepatic phenotypes and functions.

EXAMPLE 5

Expansion of Functional hiHep Cells by SV40 Large T Antigen

Figure 5:
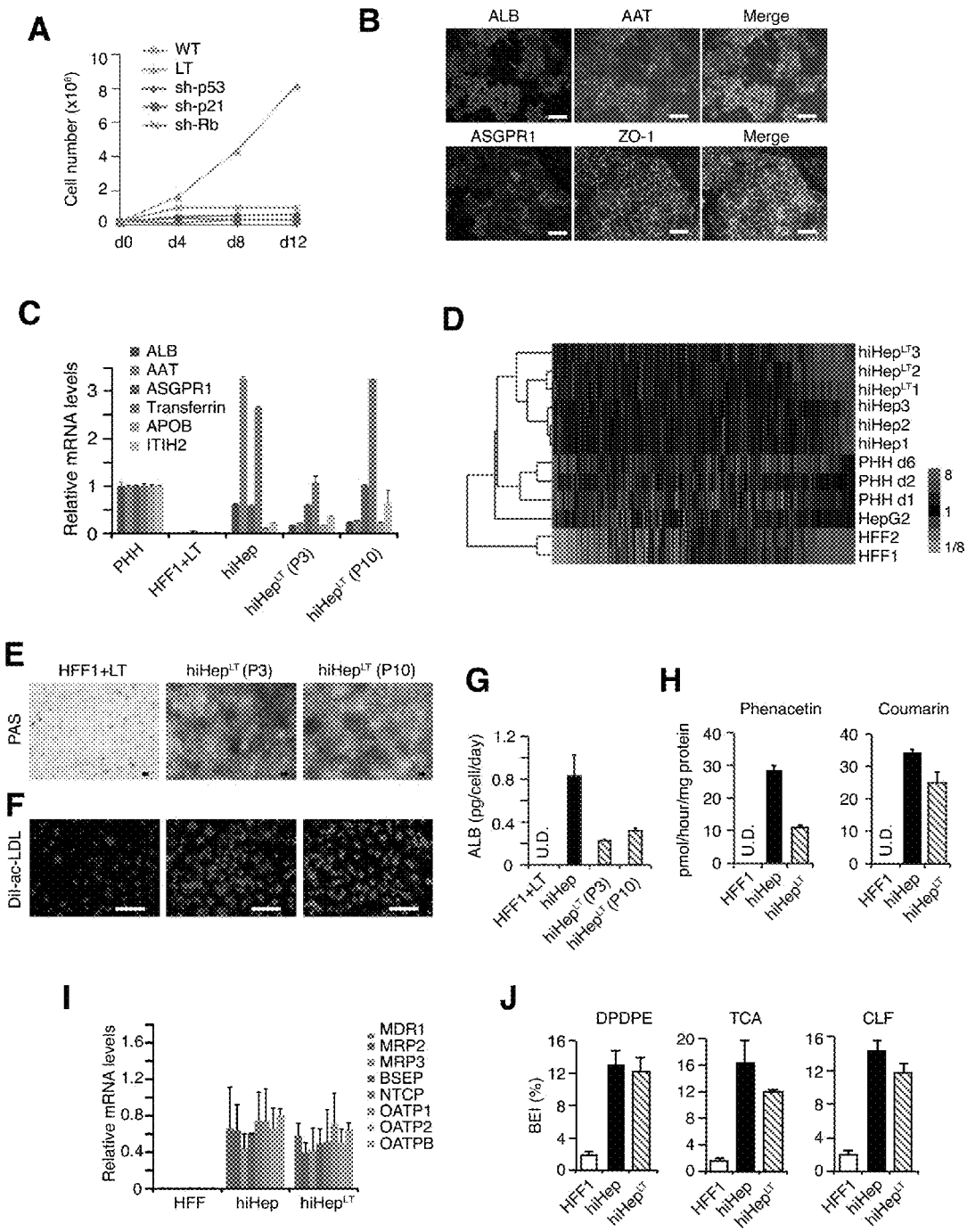
FIGS. 5A-5J are a set of diagrams and photographs showing expanding hiHep cells: (A) hiHep cells are proliferation arrested. Knockdown of p53, p21 or Rb had minimal effects on the proliferation of hiHep cells; however, SV40 large T antigen endows hiHep cells with proliferative capability. (B) Expandable hiHep$^{LT}$ cells displayed typical epithelial morphology and expressed hepatic proteins specific for mature hepatocytes as shown by co-immunostaining of ALB and AAT (up panel) and ASGPR1 and ZO-1 (low panel). (C) hiHep$^{LT}$ early (passage 3) and late (passage 10) passages show similar expression levels of hepatic genes as determined by q-PCR. (D) Whole genome expression analysis showed that the expression pattern of hiHep$^{LT}$ cells is clustered with that of hiHep cells and PHH. (E-G) hiHep$^{LT}$ cells at early and late passages show comparable glycogen accumulation (PAS staining) (E), DiI-ac-LDL intake (F) and ALB secretion (G). (H) CYP metabolic activities of hiHep$^{LT}$ cells at passage 10. (I) q-PCR assay showed that hiHep$^{LT}$ cells expressed high levels of drug transporter genes. (J) hiHep$^{LT}$ cells at passage 10 showed a biliary excretion capability comparable to that of hiHep cells. Scale bars: 100 μm. Data are represented as the mean±SD.
Figure 10:
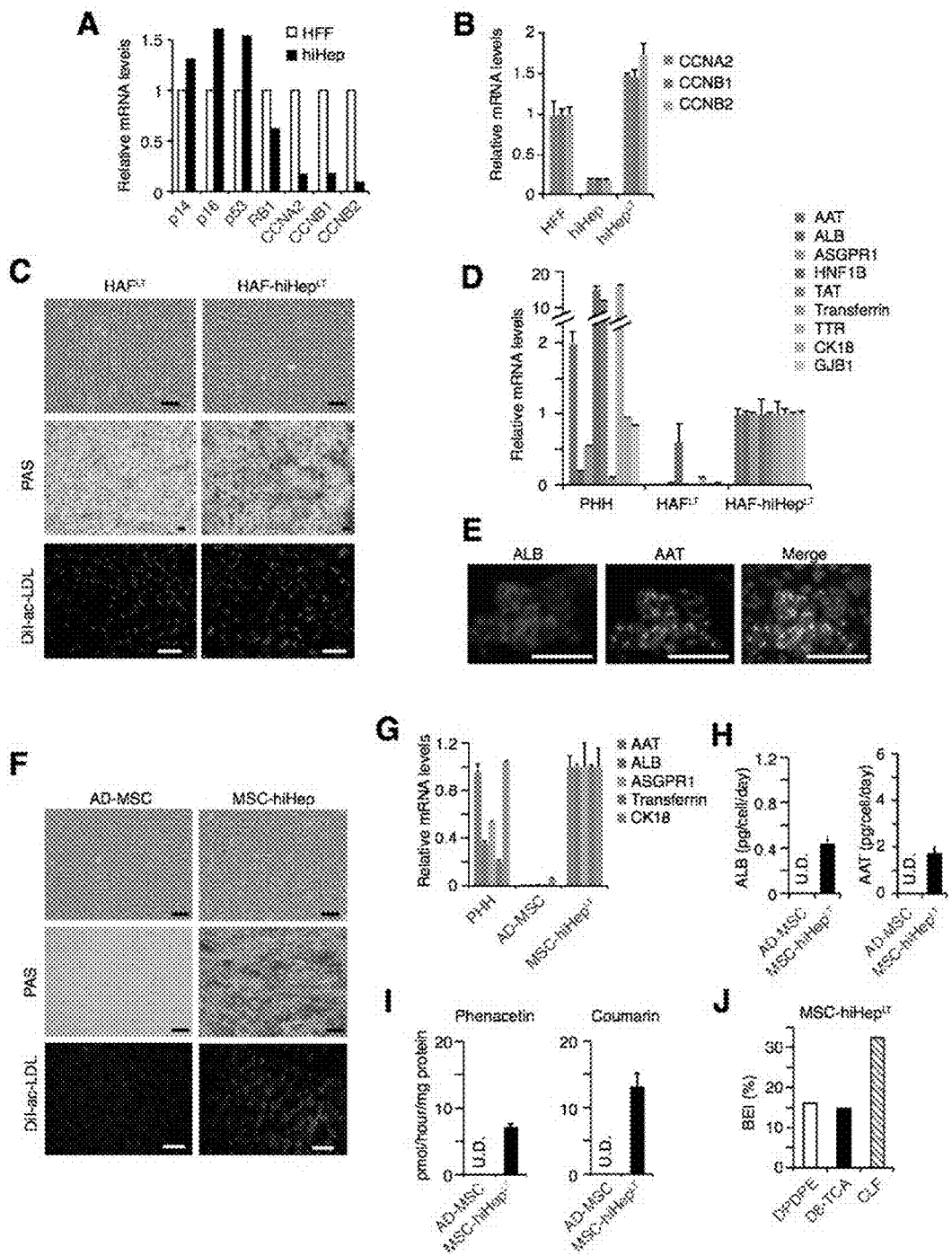
FIGS. 10A-10J are a set of diagrams and photographs showing induction of hiHep$^{LT}$ cells from human adult cells: (A, B) Cell cycle regulators in hiHep cells (A) and hiHep$^{LT}$ cells (B) were analyzed by q-PCR. Data are normalized to HFF cells. (C) HAF-derived hiHep$^{LT}$ cells showed epithelial-like morphology and possessed hepatic functions, including glycogen storage, as determined by PAS staining and ac-LDL intake. (D) Hepatic gene expression in HAF-derived hiHep$^{LT}$ cells. Data are normalized to HAF-derived hiHep$^{LT}$ cells. (E) HAF-derived hiHep$^{LT}$ cells produced both ALB and AAT proteins. (F-J) hiHep cells generated from adult adipose tissue-derived mesenchymal stem cells (AD-MSCs) (F) and express hepatic genes (G). Data are normalized to AD-MSC-derived hiHep cells. (H-J) MSC-hiHep cells also display ALB and AAT secretion (H), CYP activities (I) and biliary excretion (J). Scale bars: 100 μm.

For in vivo functional characterization, it is necessary to expand hiHep cells in large numbers. However, hiHep cells derived from both HFF and HAF were proliferation arrested (FIG. 5A), likely caused by reduced expression of Cyclin A and B (FIG. 10A). After employing several strategies, it was found that the Lentivirus-mediated expression of SV40 large T antigen (LT) allowed hiHep cells to proliferate with restored expression of Cyclin A and B (FIG. 5A and FIG. 10B). To that end, HFF1 cells were transduced with SV40 large T antigen (HFF1+LT) followed by 3TF overexpression to induce hepatic conversion (hiHep$^{LT}$). hiHep cells with LT expression (hiHep$^{LT}$) exhibited typical epithelial cell morphology (FIG. 5B) and expressed mature hepatic genes at the levels comparable to those in hiHep cells, e.g., ASGPR1 and Transferrin (FIGS. 5B and C). For q-PCR analysis, PHH cultured for 2 days were used as controls. Data were normalized to PHH.

Expression profile analysis revealed that hiHep$^{LT}$ cells were clustered together with hiHep cells and PHH (FIG. 5D). Moreover, hiHep$^{LT}$ cells acquired mature hepatic functions including glycogen accumulation, ac-LDL absorption, ALB secretion, CYP metabolism and biliary excretion (FIGS. 5E-J). For CYP metabolism assays, the products of phenacetin and coumarin metabolism were determined by liquid chromatography-tandem mass spectrometry. The products of dextromethorphan metabolism were not detected in hiHep$^{LT}$ cells.

Compared with hiHep cells, hiHep$^{LT}$ cells showed similar biliary excretion functions, whereas albumin secretion and CYP activities were attenuated (FIGS. 5G-J). Remarkably, hiHep$^{LT}$ cells maintained constant levels of hepatic gene expression and functions after several passages (FIGS. 5C-F). Similarly, hiHep$^{LT}$ cells were successfully induced from HAF (FIG. 10C-E). Furthermore, hiHep cells were generated from adipose tissue-derived mesenchymal stem cells (AD-MSC), which are readily available from patients. hiHep cells derived from AD-MSCs possessed comparable hepatic functions to those of fibroblast-derived hiHep cells (FIGS. 10F-J). As shown in FIGS. 10F-J, MSC-hiHep cells showed epithelial morphology, glycogen storage and ac-LDL intake. The products of phenacetin and coumarin metabolism were determined by liquid chromatography-tandem mass spectrometry. The products of dextromethorphan metabolism were not detected. The capability for biliary excretion as measured by clearance of DPDPE, D8-TCA and CLF.

EXAMPLE 6 hiHep Cells are Stably Converted Mature Hepatocyte-Like Cells, but not Hepatic Progenitor Cells In this example, expressions of various exogenous and endogenous factors or genes were examined. For exogenous genes, full length CDSs of the 3 transcription factors were cloned into the Lentiviral vector. Then, one primer located in the vector and the other one located in CDS were used to specifically detect exogenous genes. For endogenous mRNAs, primers located in the 3' UTR of that mRNA were used.

Figure 11:
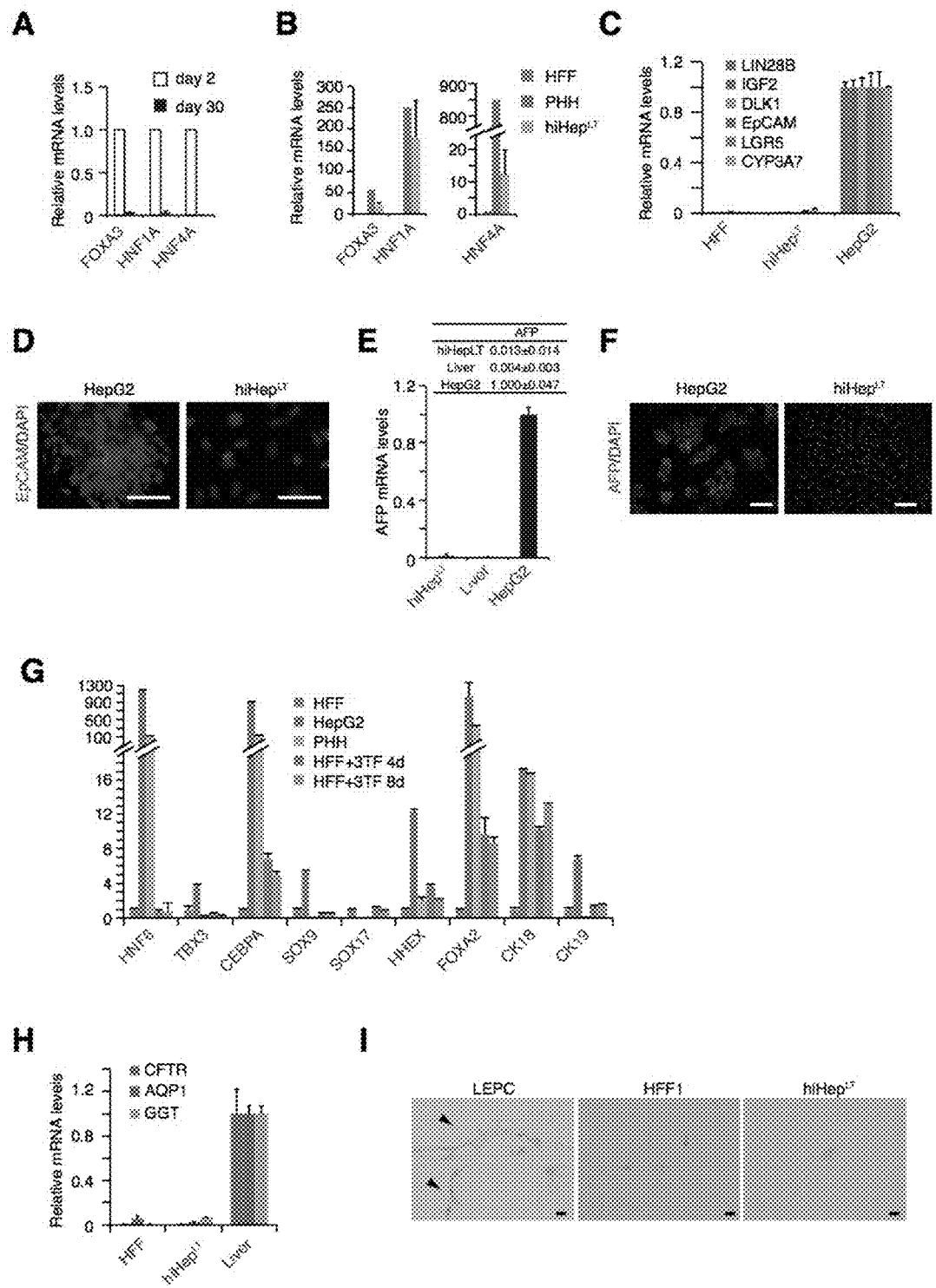
FIGS. 11A-11I are a set of diagrams and photographs showing that expandable hiHep cells are stably reprogrammed and are not hepatoblasts: (A, B) hiHep$^{LT}$ cells are stably converted hepatocyte-like cells. (A) The expression levels of ectopic transcription factors were dramatically reduced in hiHep$^{LT}$ cells cultured for 30 days. Data are normalized to day 2. (B) Endogenous FOXA3, HNF1A and HNF4A were induced in hiHep$^{LT}$ cells cultured for 30 days. (C) The expression levels of hepatoblast marker genes were determined in hiHep$^{LT}$ cells by q-PCR. Data are normalized to HepG2. (D) EpCAM, a protein that is enriched in hepatoblasts, was not detectable in hiHep$^{LT}$ cells by immunofluorescent staining. Scale bars: 50 µm. (E, F) AFP expression in hiHep$^{LT}$ cells. (E) A low level of AFP mRNA was detected by q-PCR. Data are normalized to HepG2 and are shown in the table. (F) AFP protein was not detectable in hiHep$^{LT}$ by immunofluorescent staining. Scale bars: 100 µm. (G) Expression of indicated genes during the hepatic lineage conversion. Data are normalized to HFF. (H) Genes that are enriched in bile duct cells were not expressed in hiHep$^{LT}$ cells based on q-PCR. Data are normalized to liver. (I) LEPC, a liver epithelial progenitor cell line, formed biliary branching structures at day 3 in a 3-dimensional culture system (arrow heads), whereas hiHep$^{LT}$ cells were not capable of forming branching structures.

Notably, exogenous FOXA3, HNF1A and HNF4A were silenced in expandable hiHep cells (FIG. 11A), whereas endogenous factors were markedly induced (FIG. 11B). These data suggest stable conversion of hiHep cells to a hepatic fate. Data shown in FIGS. 11A and B were normalized to HFF.

Although hiHep$^{LT}$ cells were proliferating cells, hepatoblast marker genes, including EpCAM, DLK1, LGR5 and CYP3A7, were undetectable or expressed at low levels (FIGS. 11C-D). A low level of α-fetoprotein (AFP) mRNA was detected in hiHep$^{LT}$, which is slightly higher than that observed in human liver cells (FIG. 11E). The AFP protein level in hiHep$^{LT}$ cells was undetectable by immunofluorescent staining (FIG. 11F). Furthermore, hepatoblast marker genes, including TBX3 and SOX9, were not induced during the early stage of hepatic lineage conversion (FIG. 11G). Importantly, biliary epithelium marker genes were not expressed in hiHep$^{LT}$ cells, and hiHep$^{LT}$ cells did not develop bile duct tubes in a 3-dimensional culture (FIGS. 11H-I). These results largely exclude the existence of bi-potential hepatic progenitors in hiHep cells. Taken together, our results indicate that hiHep cells are mature hepatocyte-like cells, but not hepatoblasts.

EXAMPLE 7 hiHep Cell Transplantation Improves Fah Deficiency-Induced Liver Metabolic Disease The expansion of hiHep$^{LT}$ cells in large numbers allowed the measurement of hepatic functions in vivo. To that end, hiHep$^{LT}$ cells were transplanted into fumarylacetoacetate hydrolase-deficient (Fah$^{-/-}$) mice. Fah$^{-/-}$ mice were maintained with NTBC supply and died of liver failure within 4-6 weeks after NTBC withdrawal (Azuma, et al., (2007), Nat Biotechnol 25, 903-910). Wild-type hepatocytes can repopulate the liver and rescue Fah$^{-/-}$ mice after intrasplenic transplantation, thus providing a useful model to characterize the in vivo function of hiHep cells.

To reduce the immunological response to human cells, Fah$^{-/-}$Rag2$^{-/-}$ (F/R) mice lacking mature T and B cells were additionally treated with antibodies against mouse asialo-GM1, which depleted NK-cells, and the immunosuppressive drug FK506 (FIG. 6A) (He et al. (2010), Am J Pathol 177, 1311-1319). Briefly, NTBC was withdrawn from drinking water before cell transplantation. F/R mice were pre-treated with an antibody against asialo-GM1 1 day before cell transplantation to deplete natural killer cells. HFF1 (1×10$^7$ cells), hiHep$^{LT}$ (1×10$^7$ cells) or PHH (1×10$^6$ cells) were intrasplenically transplanted into F/R mice. To reduce immune rejection of the donor cells, the recipient mice were administered anti-mouse asialo-GM1 at 7-day intervals and were given the immunosuppressive drug FK506 daily. The animals were monitored daily and sacrificed 9 weeks after transplantation. During the period, body weight was measured every week in Fah$^{-/-}$Rag2$^{-/-}$ (F/R) mice that received no transplanted cells and those that received HFF, PHH and hiHep$^{LT}$ cells. Body weights at various time points were normalized to the body weights at the commencement of the experiment.

Figure 3:
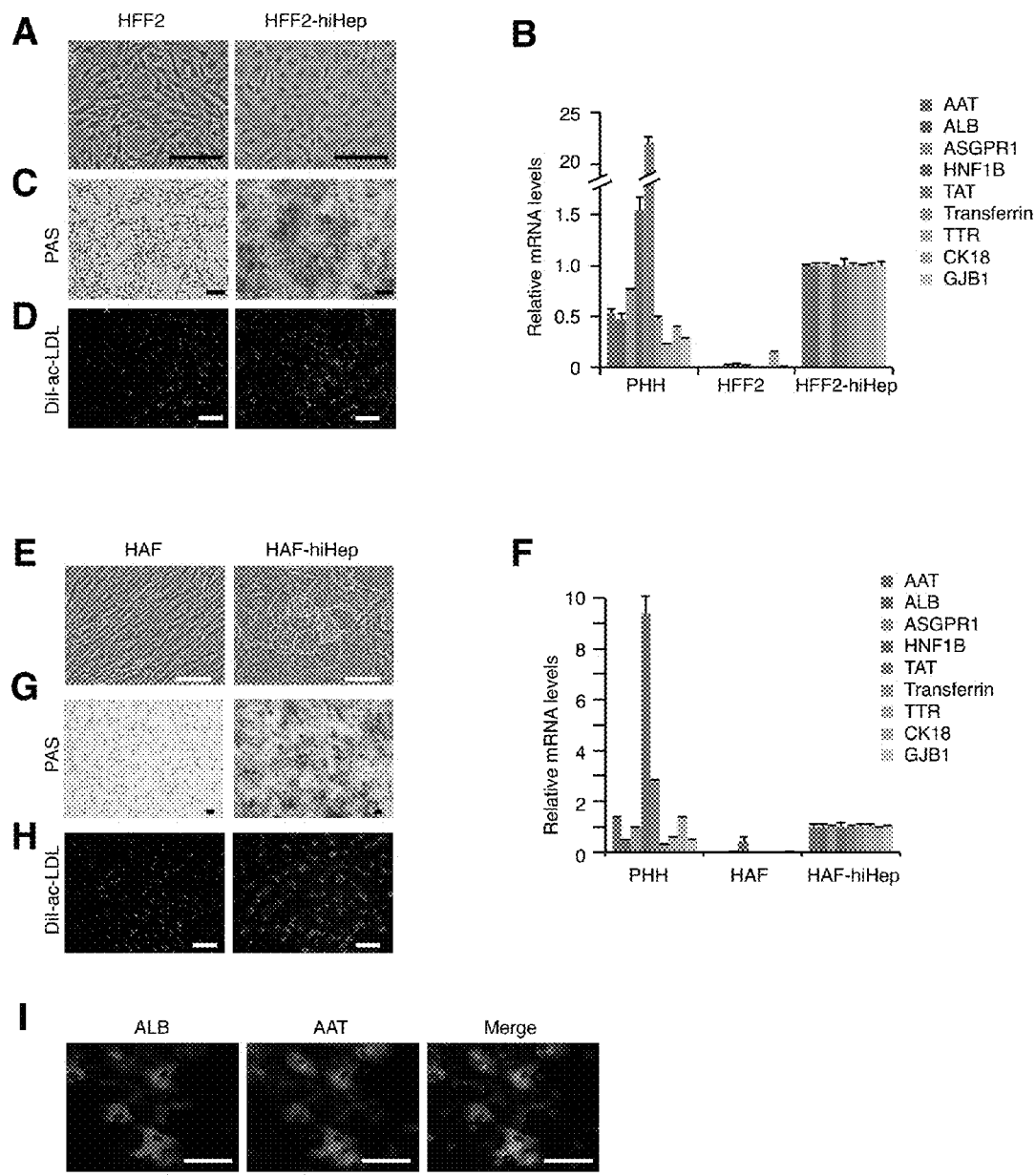
FIGS. 3A-3I are a set of diagrams and photographs showing generation of hiHep cells from human foetal and adult fibroblasts: (A) hiHep cells derived from another foetal fibroblast line, HFF2, by FOXA3, HNF1A and HNF4A overexpression exhibited epithelial-like morphology. (B) HFF2-derived hiHep cells expressed hepatic genes as determined by q-PCR. (C, D) HFF2-derived hiHep cells exhibited hepatic functions, including glycogen storage, as determined by PAS staining (C) and ac-LDL intake (D). (E) hiHep cells derived from human adult fibroblasts (HAF) exhibited epithelial-like morphology. (F) Hepatic gene expression induced by 3TF in HAF-derived hiHep cells as measured by q-PCR. (G, H) HAF-derived hiHep cells exhibited hepatic functions, including glycogen storage, as determined by PAS staining (G) and ac-LDL intake (H). (I) Twelve days after hepatic induction in HAF, 10% of the cells expressed both ALB and AAT as determined by immuno fluorescent staining. Scale bars: 100 µm. Data are represented as the mean±SD.
Figure 6:
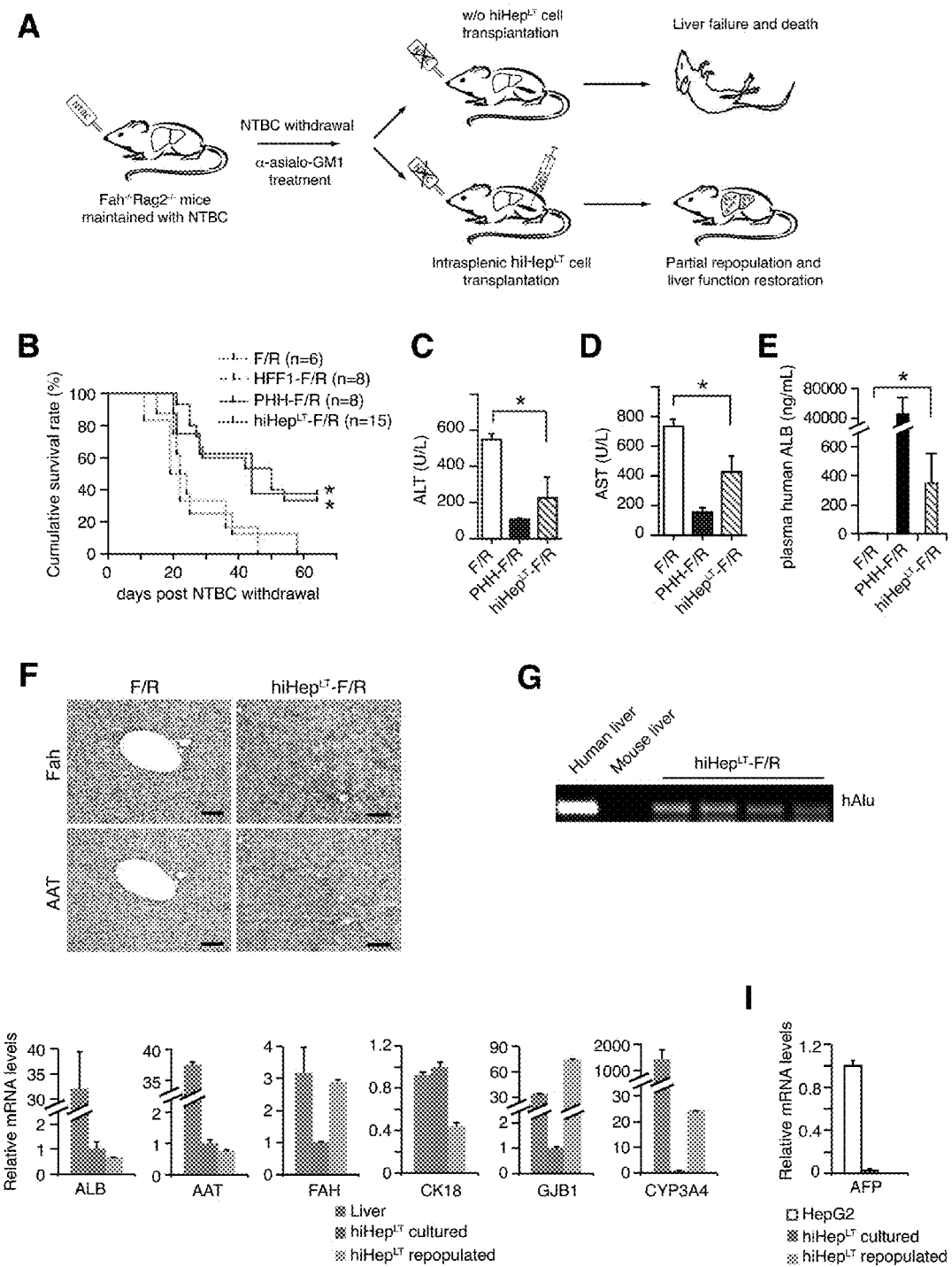
FIGS. 6A-6I are a set of diagrams and photographs showing therapeutic effects of hiHep cells on metabolic liver diseases: (A) Schematic outline of hiHep$^{LT}$ cell transplantation into the livers of Fah$^{-/-}$Rag2$^{-/-}$ mice (F/R). (B) Kaplan-Meier survival curve of F/R mice that did not receive cells or received 1×10$^7$ HFF1 (HFF-F/R), hiHep$^{LT}$ (hiHep$^{LT}$-F/R) or 1×10$^6$ PHH (PHH-F/R) after NTBC withdrawal. (C, D) Serum levels of ALT (C) and AST (D) in moribund control F/R mice (n=3), surviving hiHep$^{LT}$-F/R mice (n=5), and surviving PHH-F/R mice (n=3). (E) Human ALB levels were determined by ELISA in the sera of surviving hiHep$^{LT}$-F/R and PHH-F/R mice. (F) The integration of hiHep$^{LT}$ cells in F/R livers was determined by immunostaining for human Fah and AAT in serial sections. (G) Human-specific Alu sequences were analysed by PCR using genomic DNA extracted from hiHep$^{LT}$-repopulated F/R livers. (H, I) Fah-positive hiHep$^{LT}$ cells were collected by laser-capture micro-dissection from serial liver sections. The mRNA levels of the indicated genes were measured in hiHep$^{LT}$-repopulated nodules (hiHep$^{LT}$ repopulated) and in cultured hiHep$^{LT}$ cells (hiHep$^{LT}$ cultured) by q-PCR. Data are normalized to cultured hiHep$^{LT}$ cells (H). mRNA levels of AFP are normalized to that in HepG2 cells (I). *: $P<0.05$, log-rank test for B and t-test for C-E. Scale bars: 100 μm. Data are represented as the mean±SD.
Figure 12:
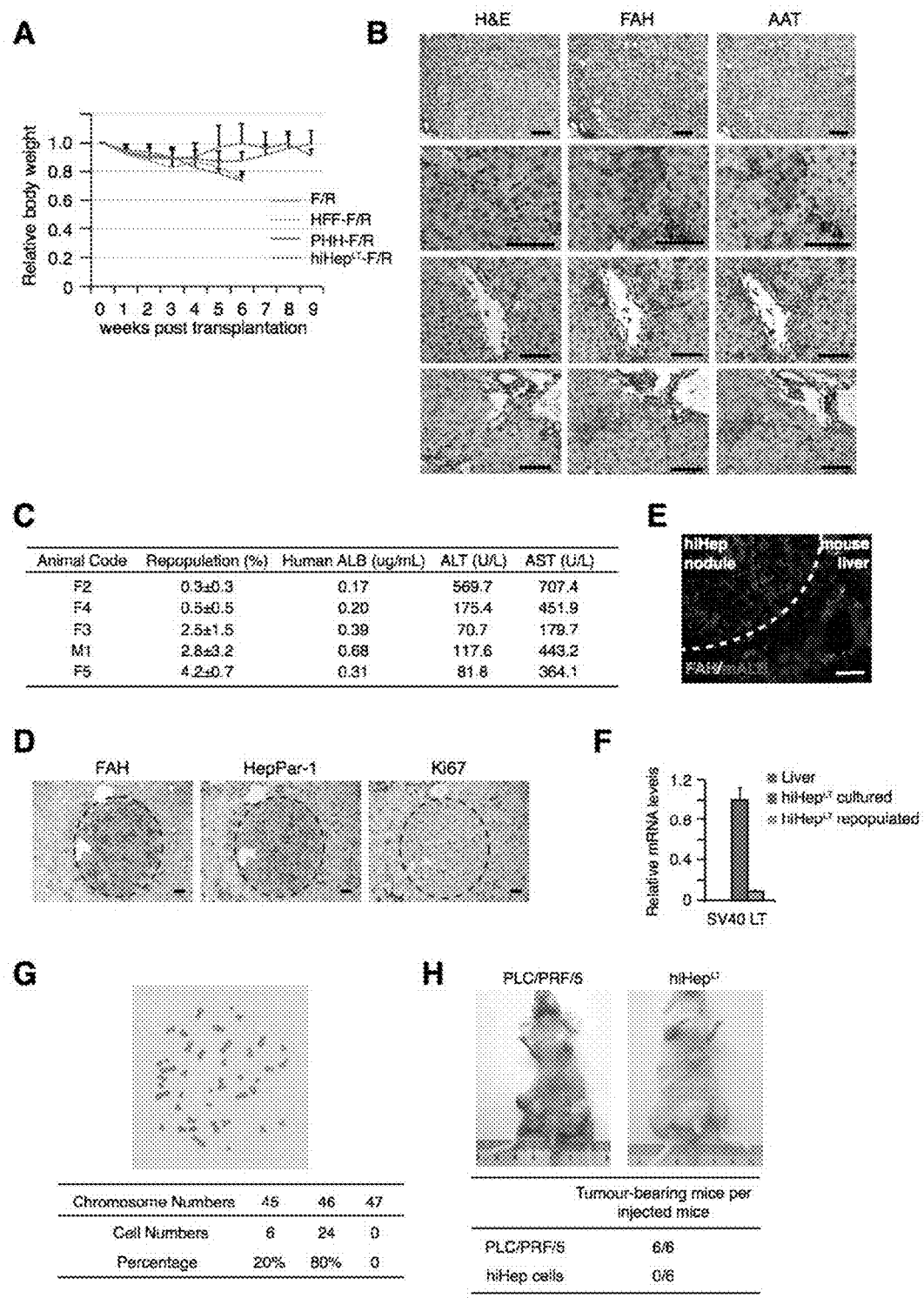
FIG. 12 are a set of diagrams and photographs showing transplantation of hiHep$^{LT}$ cells into Fah$^{-/-}$Rag2$^{-/-}$ mice: (A) Body weight curve. (B) Immunostaining of human Fah and human AAT in serial liver sections from F/R mice that received hiHep$^{LT}$ cells. (C) The improved liver function in F/R mice appeared to be correlated with the percentage of hiHep$^{LT}$ cell integration. (D) Serial sections of F/R livers 9 weeks after hiHep$^{LT}$ cell transplantation were stained by Fah, HepPar-1 and Ki67 antibodies. Fah$^+$ hiHep cells were also positively stained for HepPar-1, but were negatively stained for Ki67. (E) Cell fusion between repopulated hiHep cells and recipient mouse hepatocytes were excluded by co-staining of Fah (Green) and mouse Albumin (Red). Antibody specific for Fah stained hiHep cells, while antibody specific for mouse Albumin stained mouse hepatocytes. (F) Expression of SV40 LT in repopulated hiHep$^{LT}$ cell nodules. (G) The karyotypes of hiHep$^{LT}$ cells at passage 10. (H) hiHep$^{LT}$ cells did not form tumors 2 months after transplantation. Scale bars: 100 µm.

F/R mice that did not receive transplanted cells and those that were transplanted with HFF cells lost their body weights and died approximately 4 weeks after removing the supply of 2-(2-nitro-4-trifluoro-methylbenzyol)-1,3-cyclohexane-dione (NTBC) (FIG. 6B), whereas transplantation with PHH extended the life of F/R mice (FIG. 6B, 3 of 8 mice survived). Notably, 5 of 15 recipient mice survived 9 weeks after transplantation with hiHep$^{LT}$ cells (FIG. 6B). The mice transplanted with PHH and hiHep$^{LT}$ cells lost their body weights during the first 3 weeks, but regained or stabilized their body weights in the rest period of the experiment (FIG. 12A). Serum levels of ALT and AST were significantly reduced in the surviving recipients (FIGS. 6C and 6D), suggesting that the liver functions improved. Human ALB was also detected in the sera of mice transplanted with hiHep$^{LT}$ cells (FIG. 6E).

Immunohistochemical staining of human Fah and AAT showed that hiHep$^{LT}$ cells repopulated 0.3-4.2% of the liver parenchyma in the surviving mice (FIGS. 6F, 12B and 12C). Repopulated Fah-positive cells were positively stained by HepPar-1, an antibody specifically labelling human hepatocytes but not mouse hepatocytes or non-hepatic cells (FIG. 12D). Engraftment of hiHep$^{LT}$ cells in recipient livers was further confirmed by genomic PCR for human-specific Alu DNA sequences (FIG. 6G). Notably, hiHep cells did not fuse with mouse hepatocytes as determined by immunofluorescent staining using antibodies specifically against FAH and mouse Albumin (FIG. 12E). Repopulated hiHep$^{LT}$ cells were micro-dissected for analysis of human hepatic gene expression. Compared with cultured hiHep$^{LT}$ cells, the mRNA levels of human ALB and AAT were attenuated in repopulated hiHep$^{LT}$ cells, whereas the expression of CYP3A4 was increased (FIG. 6H). Remarkably, AFP levels were further reduced in repopulated hiHep$^{LT}$ cells (FIG. 6I), suggesting that the gene expression pattern of hiHep$^{LT}$ is further remodelled by the in vivo microenvironment. Together, our data suggest that hiHep$^{LT}$ cells can repopulate F/R livers and ameliorate impaired liver functions caused by Fah deficiency.

In this experimental setting, SV40 LT was merely employed as a strategy to expand hiHep cells for in vivo functional assays. Nevertheless, the tumorigenicity of hiHep$^{LT}$ cells was characterized. Intriguingly, tumors were not detected in recipient F/R mice (data not shown). Repopulated hiHep nodules were not proliferating as shown by Ki67 staining 9 weeks after transplantation (FIG. 12D), likely due to attenuated SV40 LT expression in vivo (FIG. 12F), which was analyzed by q-PCR and normalized to cultured hiHep$^{LT}$ cells.

Moreover, the karyotypes of hiHep$^{LT}$ cells at passage 10 were analyzed by chromosome analysis during mitosis. It was found that hiHep$^{LT}$ cells maintained normal chromosome numbers at late passages (FIG. 12G). Also, hiHep$^{LT}$ (1×10$^6$) and PLC/PRF/5 (1×10$^6$) cells were subcutaneously transplanted into the flank areas of nude mice to examine tumor formation. It was found that hiHep$^{LT}$ cells did not form tumors after transplantation in immunodeficient mice (FIG. 12H).

EXAMPLE 8 hiHep Cells Improve Con A Induced Fulminant Liver Failure

Figure 7:
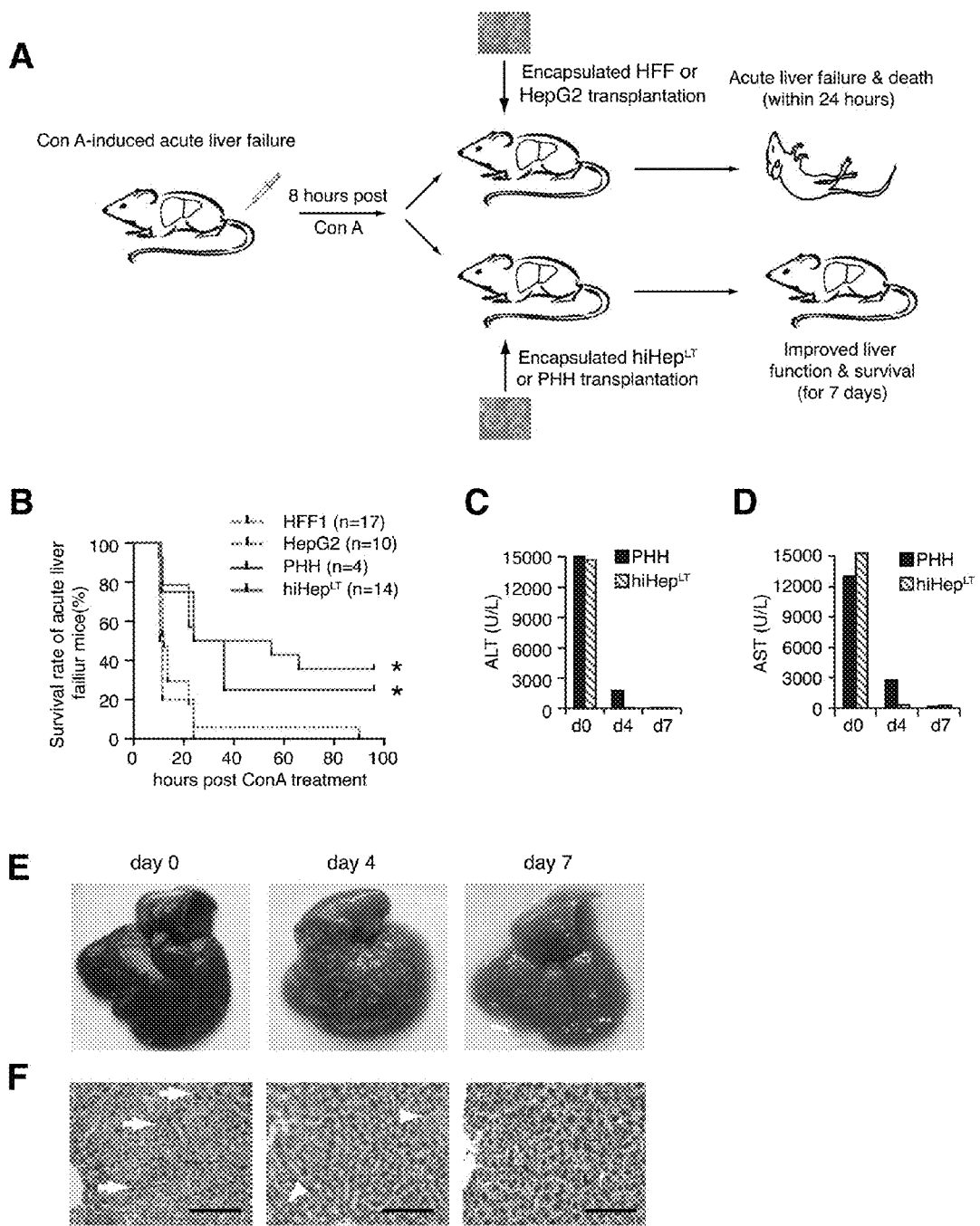
FIGS. 7A-7F are a set of diagrams and photographs showing rescue of acute liver failure by encapsulated hiHep$^{LT}$ cells: (A) Schematic outline of the use of encapsulated hiHep$^{LT}$ cells for treatment of acute liver failure mice. (B) The Kaplan-Meier survival curve. (C, D) Serum levels of ALT (C) and AST (D) in Con A-treated mice before (day 0) and after (day 4 and day 7) transplantation of encapsulated hiHep$^{LT}$ and PHH cells. (E, F) Livers (E, macroscopic images of freshly isolated livers) and liver sections (F, H&E staining) from Con A-treated mice before (day 0) and after hiHep$^{LT}$ cell transplantation (day 4 and 7). *: $P<0.05$, log-rank test for B.
Figure 13:
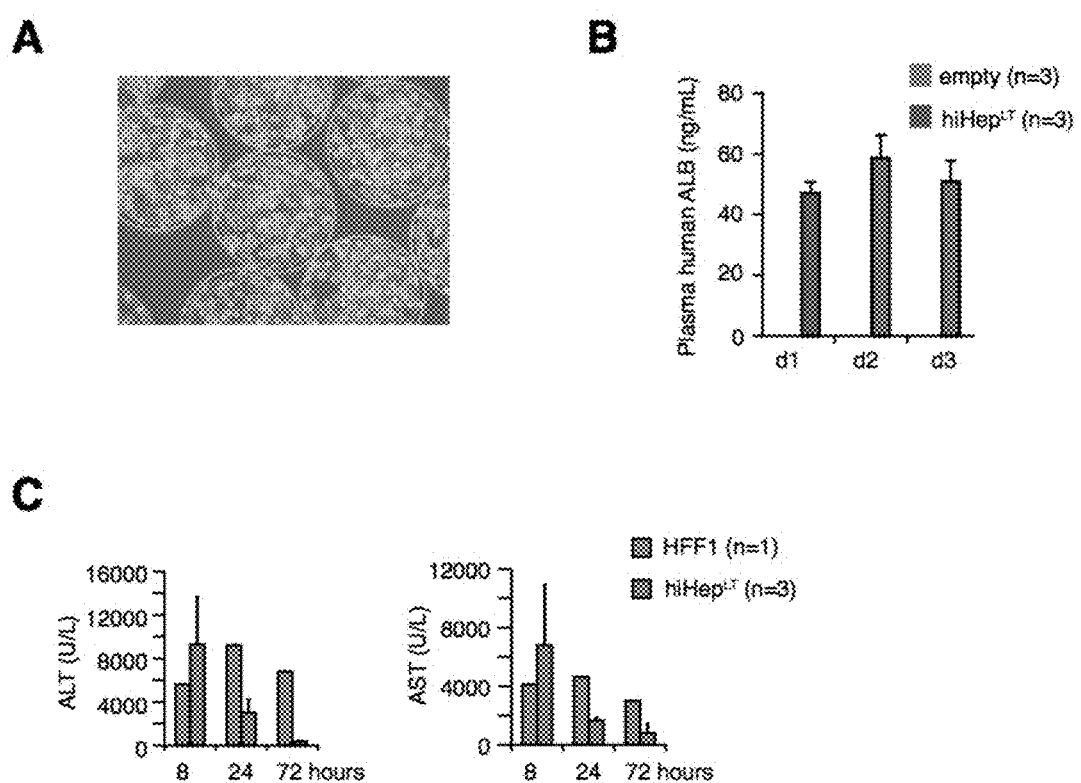
FIGS. 13A-13C are a set of diagrams and a photograph showing rescue of acute liver failure by encapsulated hiHep$^{LT}$ cells: (A) hiHep$^{LT}$ cells were encapsulated into 350 µm APA microcapsules. (B) Serum ALB levels measured daily in recipient mice after transplantation of hiHep$^{LT}$ cells. (C) Serum ALT and AST levels mice with acute liver failure that received encapsulated HFF or hiHep$^{LT}$ and survived for 3 days.

In this example, assays were carried out to determine whether hiHep cells could have sufficient hepatic functions to support liver to recover from fulminant hepatitis. To that end, wild-type mice were injected with Con A) to trigger fulminate hepatitis and animal death within 12-24 hours (FIGS. 7A and 7B). As an experimental model to demonstrate hepatic functions of hiHep cells, hiHep$^{LT}$ cells were encapsulated in APA microcapsules (FIG. 13A) and intraperitoneally injected encapsulated cells into acute liver failure mice (FIG. 7A). Previous studies have showed that transplantation of APA-encapsulated primary hepatocytes improved the survival of animals with acute liver failure (Mei, et al. (2009). Cell Transplant 18, 101-110). Semipermeable APA microcapsules isolate encapsulated cells from the immune cells in the recipient but allow the exchange of molecules smaller than 100 kD (Orive et al., (2004), Trends Biotechnol 22, 87-92; Wang et al. (2006) Hepatol Res 35, 96-103; Xie et al., (2011). J Control Release 152 Suppl 1, e246-248). As a confirmation of the semipermeability, human ALB was readily detected in the serum of recipient mice after intraperitoneal transplantation of APA-encapsulated hiHep$^{LT}$ cells (FIG. 13B).

Encapsulated cells were injected intraperitoneally into wild-type mice 8 hours after Con A treatment (FIG. 7A). More specifically, C57B16/J mice were injected with Con A to trigger fulminant hepatitis, which led to acute liver failure and death within 12-24 hours in all mice. Eight hours after Con A treatment, $5\times10^6$ encapsulated PHH or $1.5\times10^7$ APA-encapsulated HFF, HepG2 or hiHep$^{LT}$ cells were injected intraperitoneally into mice with acute liver failure. In groups transplanted with encapsulated HFF and HepG2, almost all recipients died within 24 hours after Con A treatment (1 mouse in the HFF group died at day 3, FIG. 7B). PHH treatment significantly improved the survival rate and extended the survival time of mice with acute liver failure (FIG. 7B). Markedly, upon treatment with encapsulated hiHep$^{LT}$ cells, 5 of 14 mice completely recovered from Con A-induced acute liver failure (FIG. 7B) and showed normal serum ALT and AST levels 4 days after Con A treatment (FIGS. 7C, D and 13C). It is worth noting that HepG2 cells have been used in previous models of bioartificial liver supporting devices; however, HepG2 cells showed no therapeutic effect on acute liver failure in mice, suggesting that hiHep cells may hold promise for the development of next generation of bioartificial liver supporting devices.

Histological analysis revealed that encapsulated hiHep$^{LT}$ cells significantly improved recovery from Con A-induced liver damage (FIGS. 7E and 7F). Note Con A-induced hepatitis and hemorrhage in the liver at day 0 (FIG. 7E and arrows in FIG. 7F), residual liver damage at day 4 (FIG. 7E and arrowheads in FIG. 7F) and the completely recovered liver at day 7. Together, these results reveal the hepatic functions of hiHep cells in vivo and provide evidence for the therapeutic effect of hiHep cells in the treatment of liver injuries such as metabolic liver disease and acute liver failure.

The above results demonstrate that functionally mature human hepatocyte-like cells can be generated directly from fibroblasts. In addition, the results showed that, unlike mouse cells, human cells are resistant to reprogramming, and multiple optimizations were applied to develop a new strategy for efficient hiHep induction. Listed in Table 4 below is a comparison between the procedure or protocol disclosed in the examples above and that described for mouse cells, such as that in Huang et al., (2011) Nature 475, 386-389.

TABLE 4

Comparison of Protocols for hiHep and Mouse iHep Induction

| | hiHep | mouse iHep |
|---|---|---|
| Induction factors | FOXA3, HNF1A, HNF4A | Foxa3, Hnf1α, Gata4 |
| Fibroblasts | HFF or HAF at early passages (P5-P9) | p19Arf null TTF, passage number has little effect |
| Fibroblast culture medium | DMEM/F12, 10% FBS, 0.1 mM β-ME, 1xNEAA, 4 ng/ml bFGF | DMEM, 10% FBS |
| Seeding density | 1.75-2 × 10$^5$ cells per 6 cm dish | 1 × 10$^5$ cells per 6 cm dish |
| Duration of lentiviral infection | 24 hours | 48 hours |
| Hepatocyte culture medium | DMEM/F12, 10 μM Dex, 40 ng/ml TGFα, 40 ng/ml EGF | DMEM, 0.1 μM Dex, 20 ng/ml TGFα, 10 ng/ml EGF |
| Expansion | Overexpression of SV40 large T antigen | p19Arf inactivation |

Briefly, in the protocol disclosed in the examples, it is important to use human fibroblasts at early passages. Care should be taken and human fibroblast culture medium has been optimized to maintain cells in good condition. Proper cell density is critical for induction of hiHep cells. Prolonged incubation with lentiviruses significantly reduces induction of hiHep cells and therefore should be avoided. Proper concentrations of growth factors and Dex are important to maintain hepatic features of hiHep cells. p53 or p19Arf inactivation alone could not improve the proliferation of hiHep cells. Rather, overexpression of SV40 large T antigen can be used.

Figure 14:
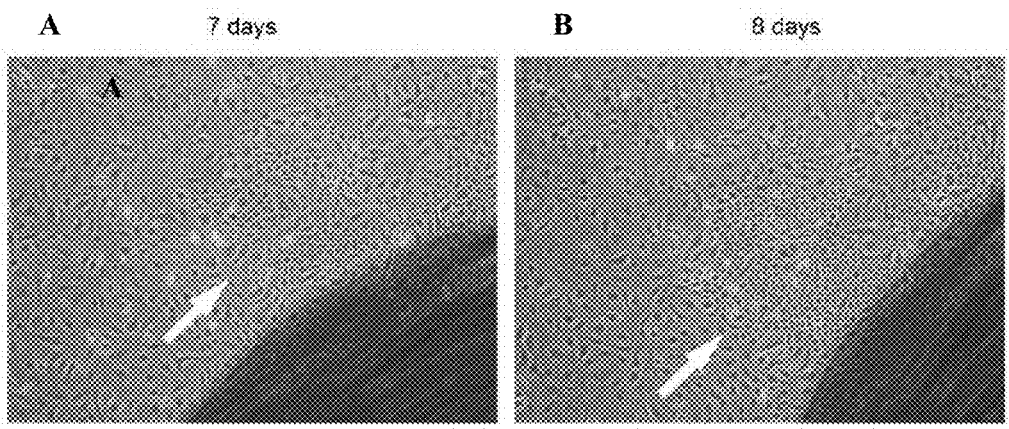
FIGS. 14A-14F are a set of photograph showing that proliferative hiHep cells were obtained by silencing RB family genes (p130, RB1 and p107) by siRNAs.
Figure 14:
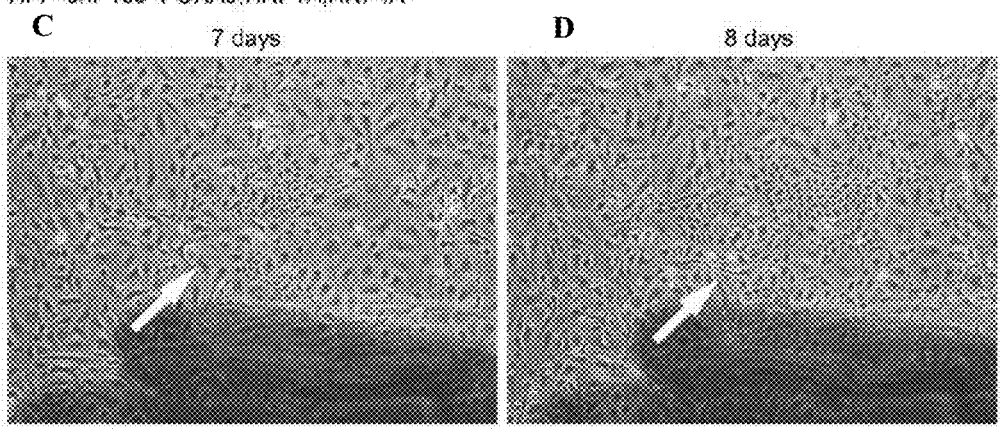
Figure 14:
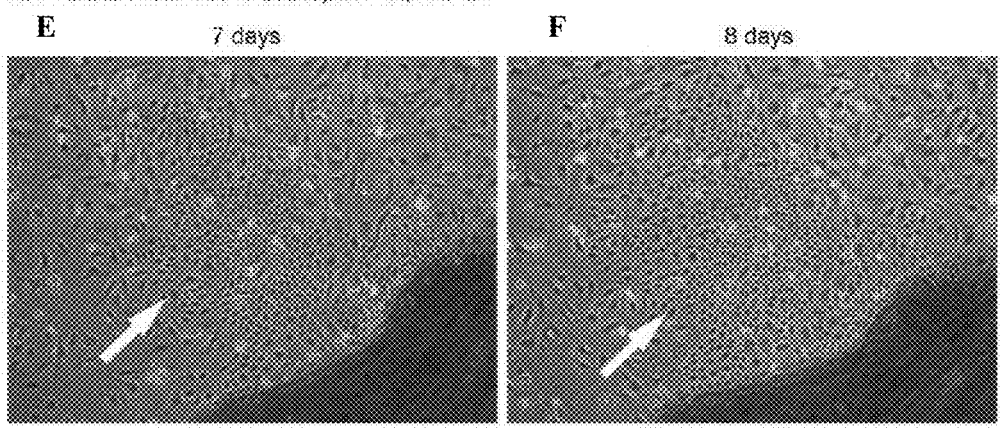
Figure 15:
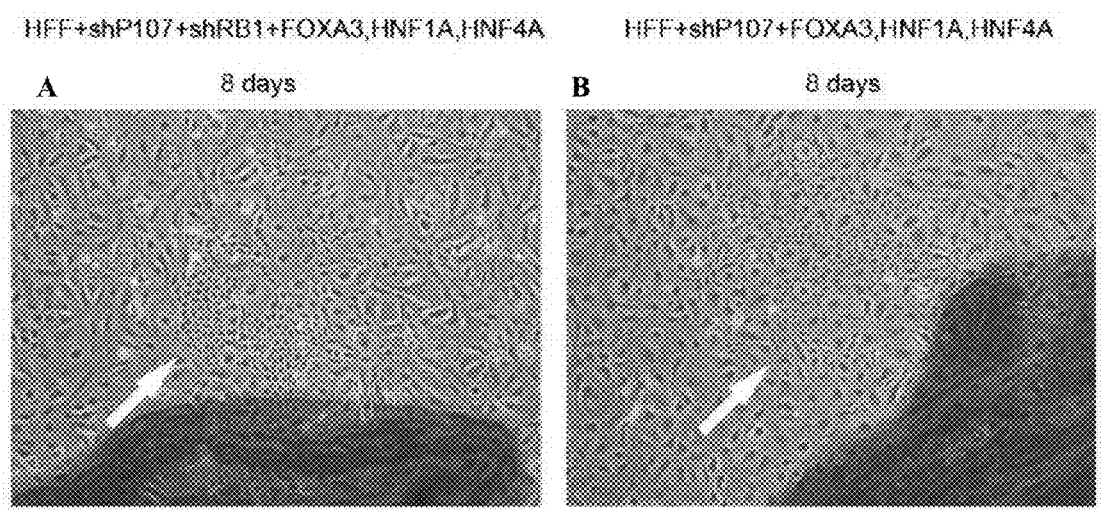
FIGS. 15A-15B are another set of photograph showing that proliferative hiHep cells were obtained by silencing RB family genes (p130, RB1 and p107) by siRNAs.

In addition, it was found that proliferative hiHep cells were also obtained by silencing other RB family genes (p130 and p107) individually or a combination with pi30 and RB1 or p107 and RB1 by siRNAs (FIGS. 14-15).

Figure 16:
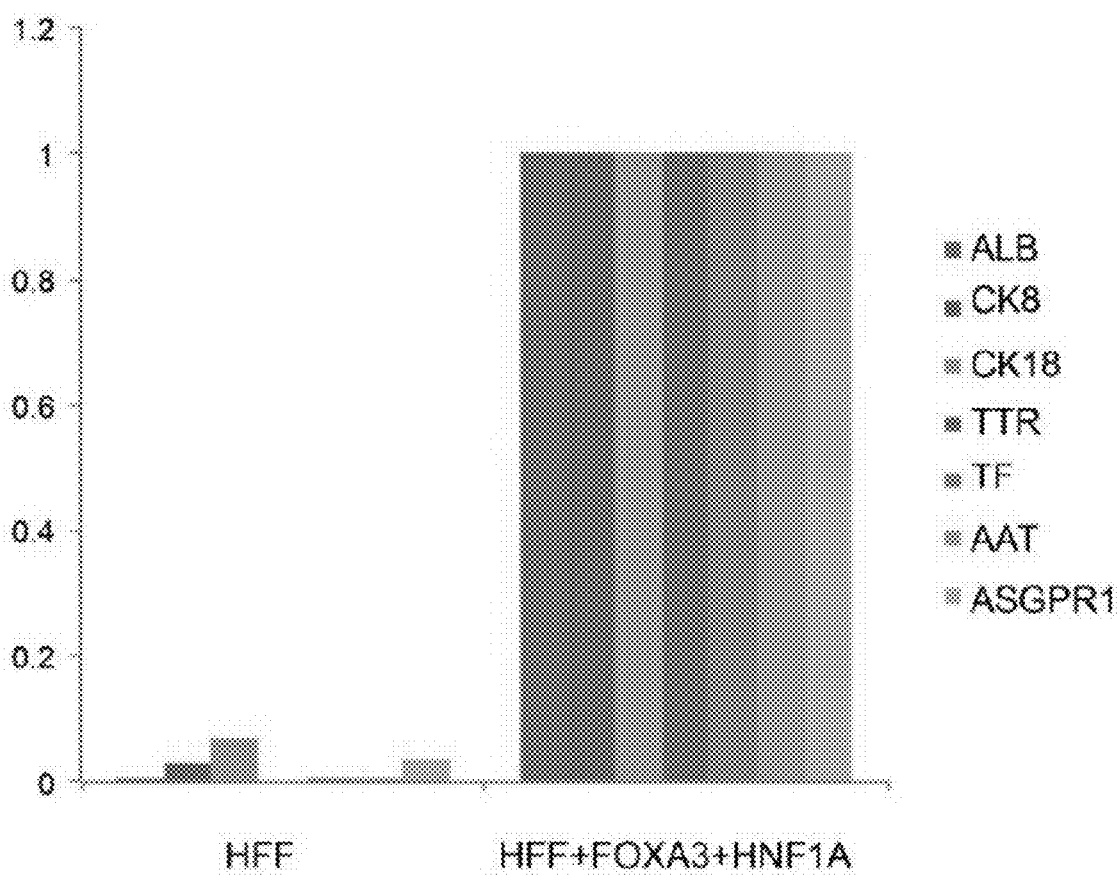
FIG. 16 is a diagram showing that hiHep cells were obtained by forced expression of FOXA3 and HNF1.
Figure 17:
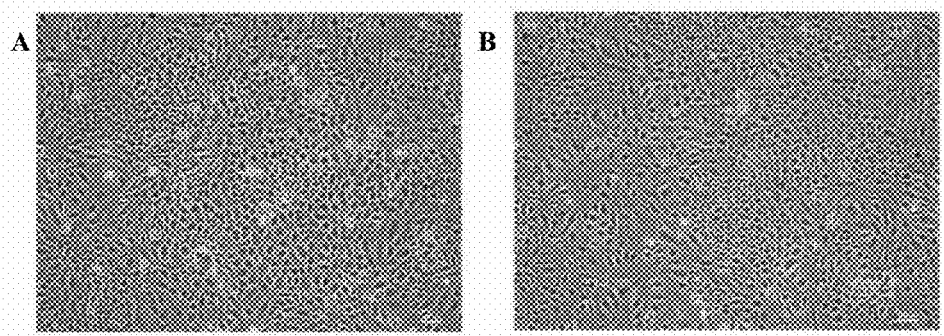
FIGS. 17A-17F are a diagram and a set of photographs showing that hiHep cells were obtained by force expression of FOXA3 and HNF4A: (A) and (B) morphology, (C) expression profile, and (D)-(F) staining of ALB, DAPI, and merge.
Figure 17:
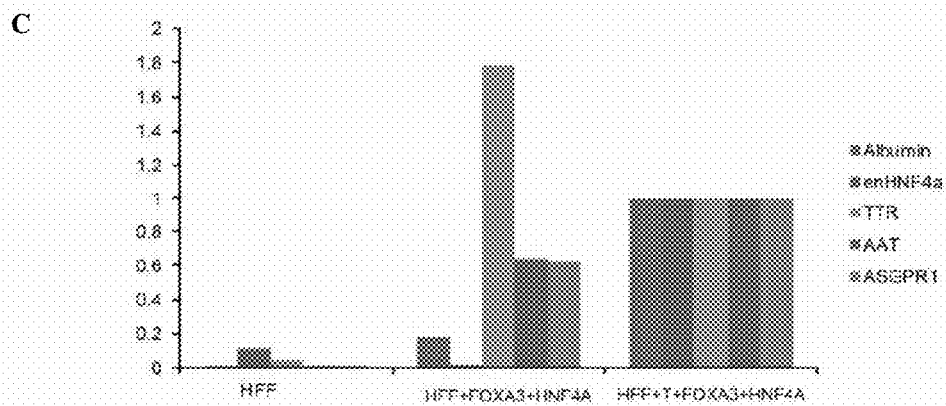
Figure 17:
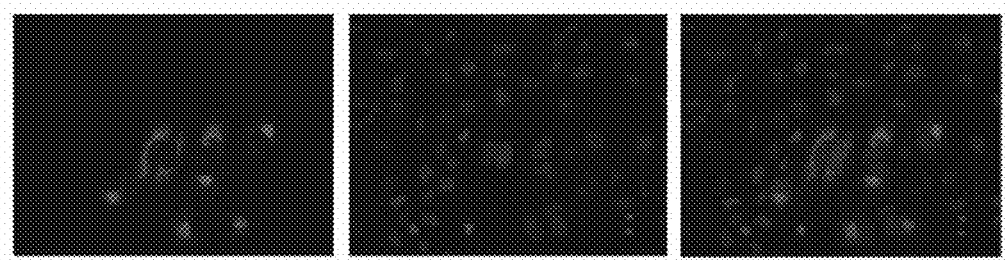

The above described protocol was also used to generate proliferative hiHep cells with even fewer TFs. It was found that hiHep cells were successfully obtained by forced expression of FOXA3 and HNF1 or FOXA3 and HNF4A. hiHep cells induced with 2TF displayed an epithelial morphology after induction (FIGS. 17A and B). The expression of genes specific for mature hepatocytes, e.g., ALB, ASGPR1 and Transferrin, was dramatically induced as measured by q-PCR and immunofluorescent staining (FIGS. 16 and 17). See FIGS. 16-17.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated herein in their entireties.

What is claimed is:

1. A method of generating human hepatocyte-like cells, comprising (i) forcing overexpression in a non-hepatic cell of a FOXA polypeptide and a plurality of HNF polypeptides by nucleic acid transfection, virus infection or protein transduction, and (ii) culturing the non-hepatic human cell in a medium for a period of time to obtain one or more progeny cells thereof, thereby generating human hepatocyte-like cells, wherein the HNF polypeptide comprises HNF4A and HNF1, and the FOXA polypeptide comprises FOXA3, wherein the HNF1 polypeptide comprises HNF1A or HNF1B or both, and wherein the non-hepatic human cell does not express a GATA4 or HHEX polypeptide.

2. The method of claim 1, comprising forcing expression of the FOXA3 polypeptide, the HNF4A polypeptide and the HNF1A polypeptide.

3. The method of claim 1, comprising forcing expression of the FOXA3 polypeptide, the HNF4A polypeptide, and both of the HNF1A polypeptide and HNF1B polypeptide in the non-hepatic human cell.

4. The method of claim 1, wherein the non-hepatic human cell is a somatic cell.

5. The method of claim 1, wherein the non-hepatic human cell is a fibroblast, an epithelium cell, a blood cell, a neuron, an embryonic cell, or a cell derived from a tissue or organ of a subject.

6. The method of claim 1, wherein the method further comprises increasing a number of the human hepatocyte-like cells generated by increasing cell proliferation or by decreasing apoptosis or cell senescence of the non-hepatic human cell or one or more of the progeny cells.

7. The method of claim 6, comprising increasing cell proliferation by forcing expression of a SV40 large T antigen in the non-hepatic human cell or one or more of the progeny cells.

8. The method of claim 6, comprising reducing expression or activity of an Rb family gene in the non-hepatic human cell or one or more of the progeny cells.

9. The method of claim 1, wherein the period of time is about 1-20 days, 2-14 days or 10-14 days.

10. The method of claim 1, wherein the method further comprises forcing expression of one or more additional polypeptides selected from the group consisting of C/EBPβ, KLF4, and PROX1 in the non-hepatic human cell.

11. A cultured hepatocyte-like cell obtained using the method of claim 1.

12. A cultured recombinant cell comprising
 (i) a plurality of heterologous HNF polypeptides comprising HNF4A and HNF1, wherein the HNF1 polypeptide comprises HNF1A or HNF1B or both;
 (ii) a heterologous FOXA polypeptide, wherein FOXA polypeptide comprises FOXA3, wherein the recombinant cell overexpresses the plurality of heterologous HNF polypeptides and the FOXA3 polypeptide and does not express a GATA4 or HHEX polypeptide.

13. The cell of claim 12, wherein the cell does not express C/EBPα.

14. The cell of claim 12, wherein the cell further comprises an additional heterologous polypeptide.

15. The cell of claim 14, wherein the additional heterologous polypeptide is selected from the group consisting of C/EBPP, KLF4, and PROX.

16. The cell of claim 12, wherein the cell further comprises a heterologous SV40 large T antigen.

17. The cell of claim 12, wherein the cell displays one or more mature hepatic functions.

18. The cell of claim 17, wherein the cell displays biliary excretion.

19. The cell of claim 17, wherein the cell is capable of metabolizing one or more compounds selected from the group consisting of 3-methylcholanthrene, phenobarbital, rifampicin, phenacetin, coumarin, dextromethorphan, testosterone, and diclofenac.

20. The cell of claim 17, wherein the cell has a normal karyotype or does not form tumor after transplantation in an immuno-deficient mouse.

21. A pharmaceutical composition comprising the cell of claim 12 and a pharmaceutically acceptable carrier.

22. The pharmaceutical composition of claim 21, wherein the cell is encapsulated in a microcapsule.

23. The pharmaceutical composition of claim 22, wherein the cell is encapsulated in a microcapsule comprising alginate-poly-L-lysine-alginate (APA).

24. A bioartificial liver device comprising
a reservoir chamber configured to house hepatocytes or hepatocyte-like cells;
a plurality of the cells of claim 12 housed in the reservoir chamber;
an inlet in fluid communication with said chamber and cells, and
an outlet in fluid communication with said chamber and cells.

25. A method for improving the liver function of a subject in need thereof, comprising (i) administering to the subject a plurality of the cells of claim 12, or (ii) administering to the subject a pharmaceutical composition comprising the cells and a pharmaceutically acceptable carrier or (iii) connecting a bioartificial liver device to the subject comprising
a reservoir chamber configured to house hepatocytes or hepatocyte-like cells;
the plurality of cells or the pharmaceutical composition housed in the reservoir chamber;
an inlet in fluid communication with said chamber and cells, and
an outlet in fluid communication with said chamber and cells.

26. The method of claim 25, wherein the plurality of cells are prepared from a non-hepatic cell of said subject.

27. A method of evaluating toxicity, carcinogenicity, or biotransformation activity of a test substance, comprising
contacting a test substance with the cell of claim 11, and
examining a level of metabolic activity or viability of the cell, wherein the level indicates the toxicity, carcinogenicity, or biotransformation activity of the test substance.

28. A composition comprising
(i) a plurality of HNF polypeptides comprising HNF4A and HNF1 polypeptides, wherein the HNF1 polypeptide comprises HNF1A or HNF1B or both;
(ii) a FOXA polypeptide,
wherein the FOXA polypeptide comprises FOXA3, and wherein the composition does not include a GATA4 polypeptide or a HHEX polypeptide.

29. The composition of claim 28, wherein the composition further comprises an additional agent selected from a group consisting of an additional polypeptide, wherein the additional polypeptide is selected from the group consisting of SV40 large T antigen, C/EBPβ, KLF4, and PROX1.

* * * * *